(12) United States Patent
Cassayre et al.

(10) Patent No.: US 8,846,907 B2
(45) Date of Patent: *Sep. 30, 2014

(54) SPIRO-CONDENSED INDOLINE DERIVATIVES AS PESTICIDES

(71) Applicant: Syngenta Crop Protection LLC, Greensboro, NC (US)

(72) Inventors: Jerome Yves Cassayre, Stein (CH); Louis-Pierre Molleyres, Basel (CH); Peter Maienfisch, Stein (CH); Fredrik Emil Malcolm Cederbaum, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/658,606

(22) Filed: Oct. 23, 2012

(65) Prior Publication Data

US 2013/0046091 A1    Feb. 21, 2013

Related U.S. Application Data

(62) Division of application No. 10/581,174, filed as application No. PCT/IB2004/004070 on Dec. 9, 2004, now Pat. No. 8,299,058.

(30) Foreign Application Priority Data

Dec. 12, 2003 (GB) .................................... 0328907.1

(51) Int. Cl.
| C07D 487/10 | (2006.01) |
| C07D 471/10 | (2006.01) |
| A01N 47/38 | (2006.01) |
| A01N 43/90 | (2006.01) |

(52) U.S. Cl.
CPC .............. *A01N 43/90* (2013.01); *C07D 487/10* (2013.01); *C07D 471/10* (2013.01); *A01N 47/38* (2013.01)
USPC .................. 540/543; 546/15; 546/17

(58) Field of Classification Search
CPC ..... A01N 43/90; C07D 471/10; C07D 487/10
USPC ............... 540/543, 546; 546/15, 17
See application file for complete search history.

(56) References Cited

U.S. PATENT DOCUMENTS

5,763,471 A * 6/1998 Fourtillan et al. ............. 514/409

FOREIGN PATENT DOCUMENTS

| WO | 9429309 | 12/1994 |
| WO | 9501358 | 1/1995 |
| WO | 9825605 | 6/1998 |
| WO | 9828297 | 7/1998 |
| WO | 9964002 | 12/1999 |
| WO | WO 03106457 A1 * | 12/2003 |

OTHER PUBLICATIONS

Hershenson et al. (Med.Chem., vol. 20, No. 11, 1977, pp. 1448-1451).*
Kawate et al. (Heterocyclyes, vol. 33, No. 2, 1992, pp. 801-811).*
Hershenson et al: "Synthesis of beta-Sprio 'pyrrolidinoindolines!, Their Binding to the Glycine Receptor, and in Vivo Biological Activity"; J.Med.Chem., vol. 20, No. 11, 1977, pp. 1448-1451.
Kawate et al: "New evidence for the presence of a spiroindolenium species in the Pictet-Spengler reaction"; Heterocycles, vol. 33, No. 2, 1992, pp. 801-811.

* cited by examiner

*Primary Examiner* — Janet Epps-Smith
*Assistant Examiner* — Courtney Brown
(74) *Attorney, Agent, or Firm* — Brian D. McAlhaney

(57) ABSTRACT

The use of a compound of formula I

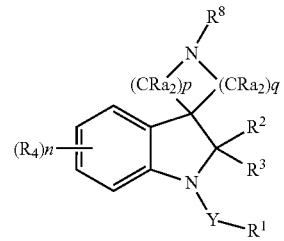

wherein Y is a single bond, C=O, C=S or $S(O)_m$ where m is 0, 1 or 2;
$R^1$, $R^2$, $R^3$, $R^4$, $R^8$ and Ra are specified organic groups and p is 0, 1, 2, 3, 4, 5 or 6;
q is 0, 1, 2, 3, 4, 5 or 6; provided that when p is 2 then q is not 2;
p+q is 1, 2, 3, 4, 5 or 6; or salts or N-oxides thereof or compositions containing them and their using in controlling insects, acarines, nematodes or molluscs. Novel compounds are also provided.

2 Claims, No Drawings

SPIRO-CONDENSED INDOLINE DERIVATIVES AS PESTICIDES

This application is a divisional of U.S. application Ser. No. 10/581,174 filed May 31, 2006, which is a U.S. Nation Stage under 35 USC 371 of International Application No. PCT/IB2004/004070 filed Dec. 9, 2004, which claims priority to GB 0328907.1 filed Dec. 12, 2003, the contents of which are incorporated herein by reference.

The present invention relates to spiroindoline derivatives, to processes for preparing them, to insecticidal, acaricidal, molluscicidal and nematicidal compositions comprising them and to methods of using them to combat and control insect, acarine, mollusc and nematode pests.

Spiroindoline derivatives with pharmaceutical properties are disclosed in for example U.S. Pat. No. 5,763,471, WO9825605, WO9429309, WO9828297 and WO9964002. Synthetic routes to selected compounds with pharmaceutical properties are described in Proc. Natl. Acad. Sci. USA (1995), 92, 7001, Tetrahedron (1997), 53, 10983 and Tetrahedron Letters (1997), 38, 1497. It has now surprisingly been found that certain spiroindolines have insecticidal properties.

The present invention therefore provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I):

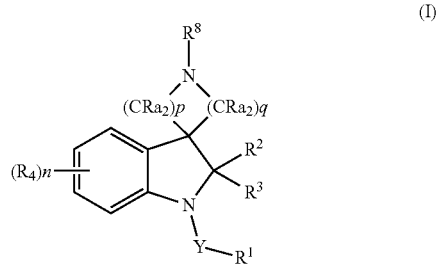

wherein Y is a single bond, C=O, C=S or $S(O)_m$ where m is 0, 1 or 2;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or $NR^{13}R^{14}$ where $R^{13}$ and $R^{14}$ are independently hydrogen, $COR^{15}$, optionally substituted alkyl, optionally substituted aryl, optionally substituted heteroaryl, optionally substituted heterocyclyl or $R^{13}$ and $R^{14}$ together with the N atom to which they are attached form a group —N=C($R^{16}$)—$NR^{17}R^{18}$; $R^{15}$ is H, optionally substituted alkyl, optionally substituted alkoxy, optionally substituted aryl, optionally substituted aryloxy optionally substituted heteroaryl, optionally substituted heteroaryloxy or $NR^{19}R^{20}$; $R^{16}$, $R^{17}$ and $R^{18}$ are each independently H or lower alkyl; $R^{19}$ and $R^{20}$ are independently optionally substituted alkyl, optionally substituted aryl or optionally substituted heteroaryl;

$R^2$ and $R^3$ are independently hydrogen, halogen, cyano, optionally substituted alkyl, optionally substituted alkoxy or optionally substituted aryl;

each $R^4$ is independently halogen, nitro, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or $R^{21}R^{22}N$ where $R^{21}$ and $R^{22}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy($C_{1-6}$)alkyl, $C_{1-6}$ alkoxycarbonyl or $R^{21}$ and $R^{22}$ together with the N atom to which they are attached form a five, six or seven-membered heterocyclic ring which may contain one or two further heteroatoms selected from O, N or S and which may be optionally substituted by one or two $C_{1-6}$ alkyl groups, or 2 adjacent groups $R^4$ together with the carbon atoms to which they are attached form a 4, 5, 6, or 7 membered carbocyclic or heterocyclic ring which may be optionally substituted by halogen; n is 0, 1, 2, 3 or 4;

each Ra is independently hydrogen, halogen, hydroxy, cyano, optionally substituted $C_{1-8}$ alkyl, optionally substituted $C_{2-6}$ alkenyl, optionally substituted $C_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted $C_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or $R^{23}R^{24}N$ where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl ($C_{1-4}$)alkyl, $C_{2-6}$ haloalkyl, $C_{1-6}$ alkoxy($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O or two Ra groups attached to adjacent carbon atoms form a bond, or two Ra groups together with the carbon atom to which they are attached form a three- to seven-membered ring, that may be saturated or unsaturated, and that may contain one or two hetero atoms selected from the group consisting of N, O and S, and which may be optionally substituted by one or two $C_{1-6}$ alkyl groups; or two Ra groups together form a group —$CH_2$—, —CH=CH— or —$CH_2CH_2$—; p is 0, 1, 2, 3, 4, 5 or 6; q is 0, 1, 2, 3, 4, 5 or 6; provided that when p is 2 then q is not 2; p+q is 1, 2, 3, 4, 5 or 6;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl; or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{12}$ alkyl groups, but are preferably $C_1$-$C_{10}$, more preferably $C_1$-$C_8$, even more preferably $C_1$-$C_6$ and most preferably $C_1$-$C_4$ alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl) aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_3CH_2$ or $CHF_2CH_2$.

In the context of the present specification the terms "aryl" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, NCS—, $C_{1-6}$ alkyl, $C_{1-6}$ haloalkyl, $C_{1-6}$ alkoxy-($C_{1-6}$) alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy ($C_{1-10}$)alkoxy, tri($C_{1-4}$)alkyl-silyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio $C_{3-7}$ cycloalkylthio (where the cycloalkyl group is optionally substituted with $C_{1-6}$ alkyl or halogen), tri($C_{1-4}$)-alkylsilyl($C_{1-6}$)alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi ($C_{1-4}$)-alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), ($C_{1-6}$)alkyloxycarbonylamino ($C_{1-6}$)alkyloxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di($C_{1-6}$)alkylaminocarbonyl amino, arylaminocarbonyl amino where the aryl group is substituted by $C_{1-6}$ alkyl or halogen), aryl-N—($C_{1-6}$)alkylaminocarbonylamino where the aryl group is substituted by $C_{1-6}$ alkyl or halogen), $C_{1-6}$ alkylaminocarbonyl-N—($C_{1-6}$)alkyl amino, di($C_{1-6}$)alkylaminocarbonyl-N—($C_{1-6}$)alkyl amino, arylaminocarbonyl-N—($C_{1-6}$)alkyl amino where the aryl group is substituted by $C_{1-6}$ alkyl or halogen) and aryl-N—($C_{1-6}$)alkylaminocarbonyl-N—($C_{1-6}$)alkyl amino where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{25}R^{26}N$ or $R^{27}R^{28}NC(O)$; wherein $R^{25}$, $R^{26}$, $R^{27}$ and $R^{28}$ are, independently, hydrogen or $C_{1-6}$ alkyl. Further preferred substituents are aryl and heteroaryl groups.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl ($C_{1-4}$)alkoxy, $C_{1-10}$ alkylthio, $C_{1-10}$ alkylcarbonyl, $C_{1-10}$ alkoxycarbonyl, $C_{1-6}$ alkylaminocarbonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$)alkylsilyl, tri($C_{1-4}$)alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-6}$ alkyl.

Preferably the optional substituents for cycloalkyl include halogen, cyano and $C_{1-3}$ alkyl.

Preferably the optional substituents for cycloalkenyl include $C_{1-3}$ alkyl, halogen and cyano.

Preferably Y is a single bond, C=O or $S(O)_m$ where m is 0, 1 or 2.

More preferably Y is a single bond, C=O or $SO_2$.

Yet more preferably Y is a single bond or C=O.

Most preferably Y is C=O.

Preferably $R^1$ is hydrogen, $C_{1-6}$ alkyl, $C_{1-6}$ cyanoalkyl, $C_{1-6}$ haloalkyl, $C_{3-7}$ cycloalkyl($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or NR$^{13}$R$^{14}$ where R$^{13}$ and R$^{14}$ are independently hydrogen, C$_{1-6}$ alkyl, C$_{1-6}$ haloalkyl, C$_{1-6}$ alkoxy(C$_{1-6}$)alkyl, phenyl (which may be optionally substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino, dialkylamino or C$_{1-4}$ alkoxycarbonyl), phenyl (C$_{1-6}$)alkyl (wherein the phenyl group may be optionally substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino, dialkylamino, C$_{1-6}$ alkylsulfonyl, C$_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (C$_{1-6}$)alkyl (wherein the heteroaryl group may be optionally substituted by halo, nitro, cyano, C$_{1-6}$ alkyl, C$_{1-6}$ haloalkyl, C$_{1-6}$ alkoxy, C$_{1-6}$ haloalkoxy, C$_{1-6}$ alkylsulfonyl, C$_{1-6}$ alkylsulfinyl, C$_{1-6}$ alkylthio, C$_{1-6}$ alkoxycarbonyl, C$_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, C$_{1-6}$ alkyl, C$_{1-6}$ haloalkyl, C$_{1-6}$ alkoxy or C$_{1-6}$ haloalkoxy, C$_{1-4}$ alkoxycarbonyl C$_{1-6}$ alkylcarbonylamino, phenyloxycarbonylamino (wherein the phenyl group is optionally substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino), amino, C$_{1-6}$ alkylamino or phenylamino (wherein the phenyl group is optionally substituted halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino)).

More preferably R$^1$ is C$_{1-6}$ alkyl, C$_{1-6}$ haloalkyl, C$_{1-6}$ alkoxy(C$_{1-6}$)alkyl, heteroaryl(C$_{1-3}$)alkyl (wherein the heteroaryl group may be optionally substituted by halo, nitro, cyano, C$_{1-6}$ alkyl, C$_{1-6}$ haloalkyl, C$_{1-6}$ alkoxy, C$_{1-6}$ haloalkoxy, C$_{1-6}$ alkylsulfonyl, C$_{1-6}$ alkoxycarbonyl, or two adjacent positions on the heteroaryl system may be cyclised to form a 5, 6 or 7 membered carbocyclic or heterocyclic ring, itself optionally substituted with halogen), phenyl(C$_{1-3}$)alkyl (wherein the phenyl group may be optionally substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino, dialkylamino, C$_{1-6}$ alkylsulfonyl, C$_{1-6}$ alkoxycarbonyl, or two adjacent positions on the phenyl ring may be cyclised to form a 5, 6 or 7 membered carbocyclic or heterocyclic ring, itself optionally substituted with halogen), phenyl (which may be optionally substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino, dialkylamino, C$_{1-6}$ alkylsulfonyl, C$_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, C$_{1-6}$ alkyl, C$_{1-6}$ haloalkyl, C$_{1-6}$ alkoxy, C$_{1-6}$ haloalkoxy, C$_{1-6}$ alkylsulfonyl, C$_{1-6}$ alkoxycarbonyl, or two adjacent positions on the heteroaryl system may be cyclised to form a 5, 6 or 7 membered carbocyclic or heterocyclic ring, itself optionally substituted with halogen), C$_{1-6}$ alkoxy, C$_{1-6}$ haloalkoxy, C$_{2-6}$ alkenyl, heterocyclyl (optionally substituted by halo, cyano, C$_{1-6}$ alkyl, C$_{1-6}$ haloalkyl, C$_{1-6}$ alkoxy or C$_{1-6}$ haloalkoxy), C$_{1-6}$ alkylthio, C$_{1-6}$ haloalkylthio or NR$^{13}$R$^{14}$ where R$^{13}$ and R$^{14}$ are independently hydrogen, C$_{1-6}$ alkyl or C$_{1-6}$ haloalkyl, C$_{1-6}$ alkoxy(C$_{1-6}$)alkyl, C$_{2-6}$ alkylcarbonyl, phenylcarbonyl, (where the phenyl is optionally substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino), phenyl(C$_{1-3}$)alkyl (wherein the phenyl group may be optionally substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino, dialkylamino, C$_{1-6}$ alkylsulfonyl, C$_{1-6}$ alkoxycarbonyl, or two adjacent positions on the phenyl ring may be cyclised to form a 5, 6 or 7 membered carbocyclic or heterocyclic ring, itself optionally substituted with halogen) or heteroaryl(C$_{1-3}$)alkyl (wherein the heteroaryl group may be optionally substituted by halo, nitro, cyano, C$_{1-6}$ alkyl, C$_{1-6}$ haloalkyl, C$_{1-6}$ alkoxy, C$_{1-6}$ haloalkoxy, C$_{1-6}$ alkylsulfonyl, C$_{1-6}$ alkylsulfinyl, C$_{1-6}$ alkylthio, C$_{1-6}$ alkoxycarbonyl, C$_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen).

Even more preferably R$^1$ is C$_{1-6}$ alkyl, C$_{1-6}$ haloalkyl, heteroaryl(C$_{1-3}$)alkyl (wherein the heteroaryl group may be optionally substituted by halo, cyano, C$_{1-6}$ alkyl, C$_{1-6}$ haloalkyl and where the heteroaryl group is a thiazole, pyridine, pyrimidine, pyrazine or pyridazine ring), heteroaryl (optionally substituted by halo, cyano, C$_{1-6}$ alkyl, C$_{1-6}$ haloalkyl and where the heteroaryl group is a pyridine, pyrimidine, 2,1,3-benzoxadiazole, pyrazine or pyridazine ring), C$_{1-6}$ alkoxy, C$_{1-6}$ alkoxy(C$_{1-6}$)alkyl, C$_{1-6}$ alkylamino, C$_{1-6}$ alkoxy(C$_{1-6}$)alkylamino or heteroaryl(C$_{1-3}$)alkylamino (wherein the heteroaryl group may be optionally substituted by halo, cyano, C$_{1-6}$ alkyl, C$_{1-6}$ haloalkyl and where the heteroaryl group is a thiazole, pyridine, pyrimidine, pyrazine or pyridazine ring).

Most preferably R$^1$ is pyridyl (optionally substituted by halo, C$_{1-3}$ alkyl or C$_{1-3}$ haloalkyl) especially halo-substituted pyridyl.

It is preferred that R$^2$ and R$^3$ are independently hydrogen, C$_{1-6}$ alkyl, C$_{1-6}$ haloalkyl, C$_{1-6}$ alkoxy or cyano.

More preferably R$^2$ and R$^3$ are independently hydrogen, halogen, C$_{1-2}$ alkyl, C$_{1-2}$ haloalkyl, C$_{1-2}$ alkoxy, cyano.

Even more preferably R$^2$ and R$^3$ are independently hydrogen or C$_{1-4}$ alkyl.

Yet more preferably R$^2$ and R$^3$ are independently hydrogen or methyl.

Most preferably R$^2$ and R$^3$ are both hydrogen.

Preferably each R$^4$ is independently halogen, cyano, C$_{1-8}$ alkyl, C$_{1-8}$ haloalkyl, C$_{1-6}$ cyanoalkyl, C$_{1-6}$ alkoxy(C$_{1-6}$) alkyl, C$_{3-7}$ cycloalkyl(C$_{1-6}$)alkyl, C$_{5-6}$ cycloalkenyl(C$_{1-6}$) alkyl, C$_{3-6}$ alkenyloxy(C$_{1-6}$)alkyl, C$_{3-6}$ alkynyloxy(C$_{1-6}$) alkyl, aryloxy(C$_{1-6}$)alkyl, C$_{1-6}$ carboxyalkyl, C$_{1-6}$ alkylcarbonyl(C$_{1-6}$)alkyl, C$_{2-6}$ alkenylcarbonyl(C$_{1-6}$)alkyl, C$_{2-6}$ alkynyl carbonyl(C$_{1-6}$)-alkyl, C$_{1-6}$ alkoxycarbonyl(C$_{1-6}$) alkyl, C$_{3-6}$ alkenyloxycarbonyl(C$_{1-6}$)alkyl, C$_{3-6}$ alkynyloxycarbonyl(C$_{1-6}$)alkyl, aryloxycarbonyl(C$_{1-6}$)alkyl, C$_{1-6}$ alkylthio(C$_{1-6}$)alkyl, C$_{1-6}$ alkylsulfinyl(C$_{1-6}$)alkyl, C$_{1-6}$ alkylsulfonyl(C$_{1-6}$)alkyl, aminocarbonyl(C$_{1-6}$)alkyl, C$_{1-6}$ alkylaminocarbonyl(C$_{1-6}$)alkyl, di(C$_{1-6}$)alkylaminocarbonyl(C$_{1-6}$)alkyl, phenyl(C$_{1-4}$)alkyl (wherein the phenyl group is optionally substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino), heteroaryl(C$_{1-4}$)alkyl (wherein the heteroaryl group is optionally substituted by halo, nitro, cyano, C$_{1-6}$ alkyl, C$_{1-6}$ haloalkyl, C$_{1-6}$ alkoxy or C$_{1-6}$ haloalkoxy), heterocyclyl(C$_{1-4}$)alkyl (wherein the heterocyclyl group is optionally substituted by halo, nitro, cyano, C$_{1-6}$ alkyl, C$_{1-6}$ haloalkyl, C$_{1-6}$ alkoxy or C$_{1-6}$ haloalkoxy), C$_{2-6}$ alkenyl, aminocarbonyl(C$_{2-6}$)alkenyl, C$_{1-6}$ alkylaminocarbonyl(C$_{2-6}$)alkenyl, di(C$_{1-6}$)alkylaminocarbonyl(C$_{2-6}$)alkenyl, phenyl(C$_{2-4}$)-alkenyl, (wherein the phenyl group is optionally substituted by halogen, C$_{1-4}$ alkyl, C$_{1-4}$ alkoxy, C$_{1-4}$ haloalkyl, C$_{1-4}$ haloalkoxy, CN, NO$_2$, aryl, heteroaryl, amino or dialkylamino), C$_{2-6}$ alkynyl, trimethylsilyl(C$_{2-6}$)alkynyl, aminocarbonyl(C$_{2-6}$)alkynyl, C$_{1-6}$ alkylaminocarbonyl(C$_{2-6}$) alkynyl, di(C$_{1-6}$)alkylaminocarbonyl(C$_{2-6}$)alkynyl, C$_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl ($C_{3-7}$)halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups $R^4$ together with the carbon atoms to which they are attached form a 4, 5, 6 or 7 membered carbocyclic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups; n is 0, 1, 2 or 3.

More preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, trimethylsilyl($C_{2-6}$)alkynyl, $C_{1-6}$ alkoxycarbonyl, $C_{3-7}$ cycloalkyl, $C_{1-3}$ alkyl ($C_{3-7}$) cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-3}$ alkyl, $C_{1-3}$ haloalkyl, $C_{1-3}$ alkoxy or $C_{1-3}$ haloalkoxy), di($C_{1-8}$)alkylamino, or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Even more preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), di($C_{1-8}$)alkylamino or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Yet more preferably each $R^4$ is independently fluoro, chloro, bromo, cyano, $C_{1-4}$ alkyl, $C_{1-4}$ haloalkyl, $C_{1-4}$ cyanoalkyl or $C_{1-3}$ alkoxy($C_{1-3}$)alkyl; n is 0, 1 or 2.

Most preferably each $R^4$ is independently fluoro, chloro, bromo, $C_{1-4}$ alkyl or $C_{1-4}$ haloalkyl; n is 1 or 2.

Preferably $R^8$ is $C_{1-10}$ alkyl, $C_{1-10}$ haloalkyl, aryl($C_{1-6}$) alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or $—C(R^{51})(R^{52})—[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

More preferably $R^8$ is phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl ($C_{2-6}$)alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{2-6}$)alkenyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, or $—C(R^{51})(R^{52})—[CR^{53}=CR^{54}]_z—R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

Most preferably $R^8$ is $—C(R^{51})(R^{52})—[CR^{53}=CR^{54}]_z—R^{55}$ where z is 1 or 2, preferably 1, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

$R^{51}$ and $R^{52}$ are preferably hydrogen.

$R^{53}$ and $R^{54}$ are preferably hydrogen or halogen, especially hydrogen. $R^{55}$ is preferably phenyl substituted with one to three substituents selected from halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

Preferably each Ra is independently hydrogen, halo, cyano, $C_{1-3}$ alkyl, hydroxy or two Ra groups together with the carbon atom to which they are attached form a carbonyl group More preferably each Ra is independently hydrogen, fluoro, methyl, hydroxy or two Ra groups together with the carbon atom to which they are attached form a carbonyl group Most preferably each Ra is hydrogen.

Preferably p is 1 or 2 and q is 2 or 3 and p+q is 3, 4 or 5.
More preferably p is 1 or 2 and q is 2 or 3.
Most preferably p is 1 and q is 2 or 3.

One group of preferred compounds of formula (I) are those where Y is C(O) and $R^1$ is $NR^{13}R^{14}$ where $R^{13}$ and $R^{14}$ are as defined above Certain compounds of formula (I) are novel and as such form a further aspect of the invention. One group of novel compounds are compounds of formula I'

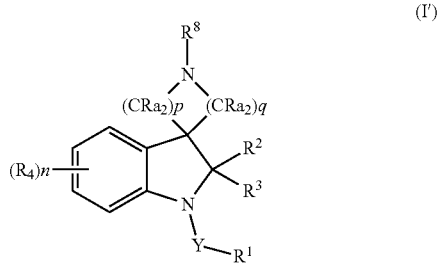

(I')

wherein Y is CO, $R^2$ and $R^3$ are both hydrogen and $R^1$, $R^4$, $R^8$, $R^a$, n, p and q are as defined in relation to formula I provided that when n is 0, p is 1, q is 2, R1 is $CH_3$ and all groups Ra are H then $R^8$ is not H, methyl, benzyl or $CH_2$—CH=$CH_2$ and when n is 0, $(CRa_2)_p$ is CH-phenyl, $(CRa_2)q$ is $(CH_2)_2$ and $R^1$ is methyl then $R^8$ is not $COOCH_3$.

The compounds in Tables I to CCIV below illustrate the compounds of the invention.

Table I provides 782 compounds of formula Ia

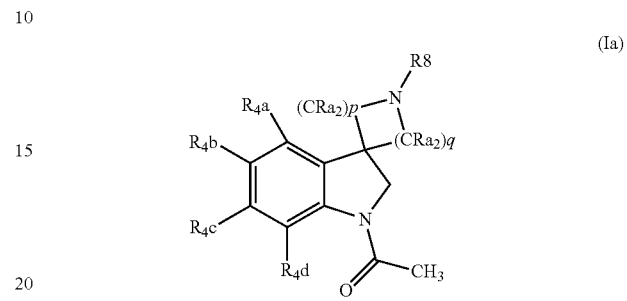

(Ia)

wherein each Ra is H, p is 1, q is 2 and the values of $R^8$, $R^{4a}$, $R^{4b}$, $R^{4c}$ and $R^{4d}$ are given in Table 1

TABLE 1

| Compound No | $R^8$ | $R^{4a}$ | $R^{4b}$ | $R^{4c}$ | $R^{4d}$ |
|---|---|---|---|---|---|
| I-1 | 4-chlorobenzyl | H | H | H | H |
| I-2 | Cinnamyl | H | H | H | H |
| I-3 | 4-chlorocinnamyl | H | H | H | H |
| I-4 | 4-fluorocinnamyl | H | H | H | H |
| I-5 | 4-bromocinnamyl | H | H | H | H |
| I-6 | 4-trifluoromethylcinnamyl | H | H | H | H |
| I-7 | 4-trifluoromethoxycinnamyl | H | H | H | H |
| I-8 | 4-pentafluoroethoxycinnamyl | H | H | H | H |
| I-9 | 4-methoxycinnamyl | H | H | H | H |
| I-10 | 4-ethoxycinnamyl | H | H | H | H |
| I-11 | 4-cyanocinnamyl | H | H | H | H |
| I-12 | 3-(6-chloro-pyridin-3-yl)-allyl | H | H | H | H |
| I-13 | 3-(4-chlorophenyl)-but-2-enyl | H | H | H | H |
| I-14 | 3-(4-chlorophenyl)-3-fluoro-allyl | H | H | H | H |
| I-15 | 3-chloro-4-fluoro-cinnamyl | H | H | H | H |
| I-16 | 3,5-dichloro-cinnamyl | H | H | H | H |
| I-17 | 5-phenyl-penta-2,4-dienyl | H | H | H | H |
| I-18 | 4-isopropyloxycarbonylamino-cinnamyl | H | H | H | H |
| I-19 | 3-naphthalen-2-yl-allyl | H | H | H | H |
| I-20 | 3-(5-trifluoromethyl-pyridin-2-yl)-allyl | H | H | H | H |
| I-21 | 3-(5-chloro-pyridin-2-yl)-allyl | H | H | H | H |
| I-22 | 3-pyridin-4-yl-allyl | H | H | H | H |
| I-23 | 3-(2-Chloro-pyridin-4-yl)-allyl | H | H | H | H |
| I-24 | 4-chlorobenzyl | H | F | H | H |
| I-25 | Cinnamyl | H | F | H | H |
| I-26 | 4-chlorocinnamyl | H | F | H | H |
| I-27 | 4-fluorocinnamyl | H | F | H | H |
| I-28 | 4-bromocinnamyl | H | F | H | H |
| I-29 | 4-trifluoromethylcinnamyl | H | F | H | H |
| I-30 | 4-trifluoromethoxycinnamyl | H | F | H | H |
| I-31 | 4-pentafluoroethoxycinnamyl | H | F | H | H |
| I-32 | 4-methoxycinnamyl | H | F | H | H |
| I-33 | 4-ethoxycinnamyl | H | F | H | H |
| I-34 | 4-cyanocinnamyl | H | F | H | H |
| I-35 | 3-(6-chloro-pyridin-3-yl)-allyl | H | F | H | H |
| I-36 | 3-(4-chlorophenyl)-but-2-enyl | H | F | H | H |
| I-37 | 3-(4-chlorophenyl)-3-fluoro-allyl | H | F | H | H |
| I-38 | 3-chloro-4-fluoro-cinnamyl | H | F | H | H |
| I-39 | 3,5-dichloro-cinnamyl | H | F | H | H |
| I-40 | 5-phenyl-penta-2,4-dienyl | H | F | H | H |
| I-41 | 4-isopropyloxycarbonylamino-cinnamyl | H | F | H | H |
| I-42 | 3-naphthalen-2-yl-allyl | H | F | H | H |
| I-43 | 3-(5-trifluoromethyl-pyridin-2-yl)-allyl | H | F | H | H |
| I-44 | 3-(5-chloro-pyridin-2-yl)-allyl | H | F | H | H |
| I-45 | 3-pyridin-4-yl-allyl | H | F | H | H |
| I-46 | 3-(2-Chloro-pyridin-4-yl)-allyl | H | F | H | H |

TABLE 1-continued

| Compound No | R⁸ | R⁴ᵃ | R⁴ᵇ | R⁴ᶜ | R⁴ᵈ |
|---|---|---|---|---|---|
| I-47 | 4-chlorobenzyl | H | Cl | H | H |
| I-48 | Cinnamyl | H | Cl | H | H |
| I-49 | 4-chlorocinnamyl | H | Cl | H | H |
| I-50 | 4-fluorocinnamyl | H | Cl | H | H |
| I-51 | 4-bromocinnamyl | H | Cl | H | H |
| I-52 | 4-trifluoromethylcinnamyl | H | Cl | H | H |
| I-53 | 4-trifluoromethoxycinnamyl | H | Cl | H | H |
| I-54 | 4-pentafluoroethoxycinnamyl | H | Cl | H | H |
| I-55 | 4-methoxycinnamyl | H | Cl | H | H |
| I-56 | 4-ethoxycinnamyl | H | Cl | H | H |
| I-57 | 4-cyanocinnamyl | H | Cl | H | H |
| I-58 | 3-(6-chloro-pyridin-3-yl)-allyl | H | Cl | H | H |
| I-59 | 3-(4-chlorophenyl)-but-2-enyl | H | Cl | H | H |
| I-60 | 3-(4-chlorophenyl)-3-fluoro-allyl | H | Cl | H | H |
| I-61 | 3-chloro-4-fluoro-cinnamyl | H | Cl | H | H |
| I-62 | 3,5-dichloro-cinnamyl | H | Cl | H | H |
| I-63 | 5-phenyl-penta-2,4-dienyl | H | Cl | H | H |
| I-64 | 4-isopropyloxycarbonylamino-cinnamyl | H | Cl | H | H |
| I-65 | 3-naphthalen-2-yl-allyl | H | Cl | H | H |
| I-66 | 3-(5-trifluoromethyl-pyridin-2-yl)-allyl | H | Cl | H | H |
| I-67 | 3-(5-chloro-pyridin-2-yl)-allyl | H | Cl | H | H |
| I-68 | 3-pyridin-4-yl-allyl | H | Cl | H | H |
| I-69 | 3-(2-Chloro-pyridin-4-yl)-allyl | H | Cl | H | H |
| I-70 | 4-chlorobenzyl | H | Br | H | H |
| I-71 | Cinnamyl | H | Br | H | H |
| I-72 | 4-chlorocinnamyl | H | Br | H | H |
| I-73 | 4-fluorocinnamyl | H | Br | H | H |
| I-74 | 4-bromocinnamyl | H | Br | H | H |
| I-75 | 4-trifluoromethylcinnamyl | H | Br | H | H |
| I-76 | 4-trifluoromethoxycinnamyl | H | Br | H | H |
| I-77 | 4-pentafluoroethoxycinnamyl | H | Br | H | H |
| I-78 | 4-methoxycinnamyl | H | Br | H | H |
| I-79 | 4-ethoxycinnamyl | H | Br | H | H |
| I-80 | 4-cyanocinnamyl | H | Br | H | H |
| I-81 | 3-(6-chloro-pyridin-3-yl)-allyl | H | Br | H | H |
| I-82 | 3-(4-chlorophenyl)-but-2-enyl | H | Br | H | H |
| I-83 | 3-(4-chlorophenyl)-3-fluoro-allyl | H | Br | H | H |
| I-84 | 3-chloro-4-fluoro-cinnamyl | H | Br | H | H |
| I-85 | 3,5-dichloro-cinnamyl | H | Br | H | H |
| I-86 | 5-phenyl-penta-2,4-dienyl | H | Br | H | H |
| I-87 | 4-isopropyloxycarbonylamino-cinnamyl | H | Br | H | H |
| I-88 | 3-naphthalen-2-yl-allyl | H | Br | H | H |
| I-89 | 3-(5-trifluoromethyl-pyridin-2-yl)-allyl | H | Br | H | H |
| I-90 | 3-(5-chloro-pyridin-2-yl)-allyl | H | Br | H | H |
| I-91 | 3-pyridin-4-yl-allyl | H | Br | H | H |
| I-92 | 3-(2-Chloro-pyridin-4-yl)-allyl | H | Br | H | H |
| I-93 | 4-chlorobenzyl | H | CN | H | H |
| I-94 | Cinnamyl | H | CN | H | H |
| I-95 | 4-chlorocinnamyl | H | CN | H | H |
| I-96 | 4-fluorocinnamyl | H | CN | H | H |
| I-97 | 4-bromocinnamyl | H | CN | H | H |
| I-98 | 4-trifluoromethylcinnamyl | H | CN | H | H |
| I-99 | 4-trifluoromethoxycinnamyl | H | CN | H | H |
| I-100 | 4-pentafluoroethoxycinnamyl | H | CN | H | H |
| I-101 | 4-methoxycinnamyl | H | CN | H | H |
| I-102 | 4-ethoxycinnamyl | H | CN | H | H |
| I-103 | 4-cyanocinnamyl | H | CN | H | H |
| I-104 | 3-(6-chloro-pyridin-3-yl)-allyl | H | CN | H | H |
| I-105 | 3-(4-chlorophenyl)-but-2-enyl | H | CN | H | H |
| I-106 | 3-(4-chlorophenyl)-3-fluoro-allyl | H | CN | H | H |
| I-107 | 3-chloro-4-fluoro-cinnamyl | H | CN | H | H |
| I-108 | 3,5-dichloro-cinnamyl | H | CN | H | H |
| I-109 | 5-phenyl-penta-2,4-dienyl | H | CN | H | H |
| I-110 | 4-isopropyloxycarbonylamino-cinnamyl | H | CN | H | H |
| I-111 | 3-naphthalen-2-yl-allyl | H | CN | H | H |
| I-112 | 3-(5-trifluoromethyl-pyridin-2-yl)-allyl | H | CN | H | H |
| I-113 | 3-(5-chloro-pyridin-2-yl)-allyl | H | CN | H | H |
| I-114 | 3-pyridin-4-yl-allyl | H | CN | H | H |
| I-115 | 3-(2-Chloro-pyridin-4-yl)-allyl | H | CN | H | H |
| I-116 | 4-chlorobenzyl | H | OMe | H | H |
| I-117 | Cinnamyl | H | OMe | H | H |
| I-118 | 4-chlorocinnamyl | H | OMe | H | H |
| I-119 | 4-fluorocinnamyl | H | OMe | H | H |
| I-120 | 4-bromocinnamyl | H | OMe | H | H |
| I-121 | 4-trifluoromethylcinnamyl | H | OMe | H | H |
| I-122 | 4-trifluoromethoxycinnamyl | H | OMe | H | H |
| I-123 | 4-pentafluoroethoxycinnamyl | H | OMe | H | H |

TABLE 1-continued

| Compound No | R8 | R4a | R4b | R4c | R4d |
|---|---|---|---|---|---|
| I-124 | 4-methoxycinnamyl | H | OMe | H | H |
| I-125 | 4-ethoxycinnamyl | H | OMe | H | H |
| I-126 | 4-cyanocinnamyl | H | OMe | H | H |
| I-127 | 3-(6-chloro-pyridin-3-yl)-allyl | H | OMe | H | H |
| I-128 | 3-(4-chlorophenyl)-but-2-enyl | H | OMe | H | H |
| I-129 | 3-(4-chlorophenyl)-3-fluoro-allyl | H | OMe | H | H |
| I-130 | 3-chloro-4-fluoro-cinnamyl | H | OMe | H | H |
| I-131 | 3,5-dichloro-cinnamyl | H | OMe | H | H |
| I-132 | 5-phenyl-penta-2,4-dienyl | H | OMe | H | H |
| I-133 | 4-isopropyloxycarbonylamino-cinnamyl | H | OMe | H | H |
| I-134 | 3-naphthalen-2-yl-allyl | H | OMe | H | H |
| I-135 | 3-(5-trifluoromethyl-pyridin-2-yl)-allyl | H | OMe | H | H |
| I-136 | 3-(5-chloro-pyridin-2-yl)-allyl | H | OMe | H | H |
| I-137 | 3-pyridin-4-yl-allyl | H | OMe | H | H |
| I-138 | 3-(2-Chloro-pyridin-4-yl)-allyl | H | OMe | H | H |
| I-139 | 4-chlorobenzyl | H | OCF$_3$ | H | H |
| I-140 | Cinnamyl | H | OCF$_3$ | H | H |
| I-141 | 4-chlorocinnamyl | H | OCF$_3$ | H | H |
| I-142 | 4-fluorocinnamyl | H | OCF$_3$ | H | H |
| I-143 | 4-bromocinnamyl | H | OCF$_3$ | H | H |
| I-144 | 4-trifluoromethylcinnamyl | H | OCF$_3$ | H | H |
| I-145 | 4-trifluoromethoxycinnamyl | H | OCF$_3$ | H | H |
| I-146 | 4-pentafluoroethoxycinnamyl | H | OCF$_3$ | H | H |
| I-147 | 4-methoxycinnamyl | H | OCF$_3$ | H | H |
| I-148 | 4-ethoxycinnamyl | H | OCF$_3$ | H | H |
| I-149 | 4-cyanocinnamyl | H | OCF$_3$ | H | H |
| I-150 | 3-(6-chloro-pyridin-3-yl)-allyl | H | OCF$_3$ | H | H |
| I-151 | 3-(4-chlorophenyl)-but-2-enyl | H | OCF$_3$ | H | H |
| I-152 | 3-(4-chlorophenyl)-3-fluoro-allyl | H | OCF$_3$ | H | H |
| I-153 | 3-chloro-4-fluoro-cinnamyl | H | OCF$_3$ | H | H |
| I-154 | 3,5-dichloro-cinnamyl | H | OCF$_3$ | H | H |
| I-155 | 5-phenyl-penta-2,4-dienyl | H | OCF$_3$ | H | H |
| I-156 | 4-isopropyloxycarbonylamino-cinnamyl | H | OCF$_3$ | H | H |
| I-157 | 3-naphthalen-2-yl-allyl | H | OCF$_3$ | H | H |
| I-158 | 3-(5-trifluoromethyl-pyridin-2-yl)-allyl | H | OCF$_3$ | H | H |
| I-159 | 3-(5-chloro-pyridin-2-yl)-allyl | H | OCF$_3$ | H | H |
| I-160 | 3-pyridin-4-yl-allyl | H | OCF$_3$ | H | H |
| I-161 | 3-(2-Chloro-pyridin-4-yl)-allyl | H | OCF$_3$ | H | H |
| I-162 | 4-chlorobenzyl | H | CH$_3$ | H | H |
| I-163 | Cinnamyl | H | CH$_3$ | H | H |
| I-164 | 4-chlorocinnamyl | H | CH$_3$ | H | H |
| I-165 | 4-fluorocinnamyl | H | CH$_3$ | H | H |
| I-166 | 4-bromocinnamyl | H | CH$_3$ | H | H |
| I-167 | 4-trifluoromethylcinnamyl | H | CH$_3$ | H | H |
| I-168 | 4-trifluoromethoxycinnamyl | H | CH$_3$ | H | H |
| I-169 | 4-pentafluoroethoxycinnamyl | H | CH$_3$ | H | H |
| I-170 | 4-methoxycinnamyl | H | CH$_3$ | H | H |
| I-171 | 4-ethoxycinnamyl | H | CH$_3$ | H | H |
| I-172 | 4-cyanocinnamyl | H | CH$_3$ | H | H |
| I-173 | 3-(6-chloro-pyridin-3-yl)-allyl | H | CH$_3$ | H | H |
| I-174 | 3-(4-chlorophenyl)-but-2-enyl | H | CH$_3$ | H | H |
| I-175 | 3-(4-chlorophenyl)-3-fluoro-allyl | H | CH$_3$ | H | H |
| I-176 | 3-chloro-4-fluoro-cinnamyl | H | CH$_3$ | H | H |
| I-177 | 3,5-dichloro-cinnamyl | H | CH$_3$ | H | H |
| I-178 | 5-phenyl-penta-2,4-dienyl | H | CH$_3$ | H | H |
| I-179 | 4-isopropyloxycarbonylamino-cinnamyl | H | CH$_3$ | H | H |
| I-180 | 3-naphthalen-2-yl-allyl | H | CH$_3$ | H | H |
| I-181 | 3-(5-trifluoromethyl-pyridin-2-yl)-allyl | H | CH$_3$ | H | H |
| I-182 | 3-(5-chloro-pyridin-2-yl)-allyl | H | CH$_3$ | H | H |
| I-183 | 3-pyridin-4-yl-allyl | H | CH$_3$ | H | H |
| I-184 | 3-(2-Chloro-pyridin-4-yl)-allyl | H | CH$_3$ | H | H |
| I-185 | 4-chlorobenzyl | H | CF$_3$ | H | H |
| I-186 | Cinnamyl | H | CF$_3$ | H | H |
| I-187 | 4-chlorocinnamyl | H | CF$_3$ | H | H |
| I-188 | 4-fluorocinnamyl | H | CF$_3$ | H | H |
| I-189 | 4-bromocinnamyl | H | CF$_3$ | H | H |
| I-190 | 4-trifluoromethylcinnamyl | H | CF$_3$ | H | H |
| I-191 | 4-trifluoromethoxycinnamyl | H | CF$_3$ | H | H |
| I-192 | 4-pentafluoroethoxycinnamyl | H | CF$_3$ | H | H |
| I-193 | 4-methoxycinnamyl | H | CF$_3$ | H | H |
| I-194 | 4-ethoxycinnamyl | H | CF$_3$ | H | H |
| I-195 | 4-cyanocinnamyl | H | CF$_3$ | H | H |
| I-196 | 3-(6-chloro-pyridin-3-yl)-allyl | H | CF$_3$ | H | H |
| I-197 | 3-(4-chlorophenyl)-but-2-enyl | H | CF$_3$ | H | H |
| I-198 | 3-(4-chlorophenyl)-3-fluoro-allyl | H | CF$_3$ | H | H |
| I-199 | 3-chloro-4-fluoro-cinnamyl | H | CF$_3$ | H | H |
| I-200 | 3,5-dichloro-cinnamyl | H | CF$_3$ | H | H |

TABLE 1-continued

| Compound No | R⁸ | R⁴ᵃ | R⁴ᵇ | R⁴ᶜ | R⁴ᵈ |
|---|---|---|---|---|---|
| I-201 | 5-phenyl-penta-2,4-dienyl | H | CF₃ | H | H |
| I-202 | 4-isopropyloxycarbonylamino-cinnamyl | H | CF₃ | H | H |
| I-203 | 3-naphthalen-2-yl-allyl | H | CF₃ | H | H |
| I-204 | 3-(5-trifluoromethyl-pyridin-2-yl)-allyl | H | CF₃ | H | H |
| I-205 | 3-(5-chloro-pyridin-2-yl)-allyl | H | CF₃ | H | H |
| I-206 | 3-pyridin-4-yl-allyl | H | CF₃ | H | H |
| I-207 | 3-(2-Chloro-pyridin-4-yl)-allyl | H | CF₃ | H | H |
| I-208 | 4-chlorobenzyl | H | H | Cl | H |
| I-209 | Cinnamyl | H | H | Cl | H |
| I-210 | 4-chlorocinnamyl | H | H | Cl | H |
| I-211 | 4-fluorocinnamyl | H | H | Cl | H |
| I-212 | 4-bromocinnamyl | H | H | Cl | H |
| I-213 | 4-trifluoromethylcinnamyl | H | H | Cl | H |
| I-214 | 4-trifluoromethoxycinnamyl | H | H | Cl | H |
| I-215 | 4-pentafluoroethoxycinnamyl | H | H | Cl | H |
| I-216 | 4-methoxycinnamyl | H | H | Cl | H |
| I-217 | 4-ethoxycinnamyl | H | H | Cl | H |
| I-218 | 4-cyanocinnamyl | H | H | Cl | H |
| I-219 | 3-(6-chloro-pyridin-3-yl)-allyl | H | H | Cl | H |
| I-220 | 3-(4-chlorophenyl)-but-2-enyl | H | H | Cl | H |
| I-221 | 3-(4-chlorophenyl)-3-fluoro-allyl | H | H | Cl | H |
| I-222 | 3-chloro-4-fluoro-cinnamyl | H | H | Cl | H |
| I-223 | 3,5-dichloro-cinnamyl | H | H | Cl | H |
| I-224 | 5-phenyl-penta-2,4-dienyl | H | H | Cl | H |
| I-225 | 4-isopropyloxycarbonylamino-cinnamyl | H | H | Cl | H |
| I-226 | 3-naphthalen-2-yl-allyl | H | H | Cl | H |
| I-227 | 3-(5-trifluoromethyl-pyridin-2-yl)-allyl | H | H | Cl | H |
| I-228 | 3-(5-chloro-pyridin-2-yl)-allyl | H | H | Cl | H |
| I-229 | 3-pyridin-4-yl-allyl | H | H | Cl | H |
| I-230 | 3-(2-Chloro-pyridin-4-yl)-allyl | H | H | Cl | H |
| I-231 | 4-chlorobenzyl | H | H | F | H |
| I-232 | Cinnamyl | H | H | F | H |
| I-233 | 4-chlorocinnamyl | H | H | F | H |
| I-234 | 4-fluorocinnamyl | H | H | F | H |
| I-235 | 4-bromocinnamyl | H | H | F | H |
| I-236 | 4-trifluoromethylcinnamyl | H | H | F | H |
| I-237 | 4-trifluoromethoxycinnamyl | H | H | F | H |
| I-238 | 4-pentafluoroethoxycinnamyl | H | H | F | H |
| I-239 | 4-methoxycinnamyl | H | H | F | H |
| I-240 | 4-ethoxycinnamyl | H | H | F | H |
| I-241 | 4-cyanocinnamyl | H | H | F | H |
| I-242 | 3-(6-chloro-pyridin-3-yl)-allyl | H | H | F | H |
| I-243 | 3-(4-chlorophenyl)-but-2-enyl | H | H | F | H |
| I-244 | 3-(4-chlorophenyl)-3-fluoro-allyl | H | H | F | H |
| I-245 | 3-chloro-4-fluoro-cinnamyl | H | H | F | H |
| I-246 | 3,5-dichloro-cinnamyl | H | H | F | H |
| I-247 | 5-phenyl-penta-2,4-dienyl | H | H | F | H |
| I-248 | 4-isopropyloxycarbonylamino-cinnamyl | H | H | F | H |
| I-249 | 3-naphthalen-2-yl-allyl | H | H | F | H |
| I-250 | 3-(5-trifluoromethyl-pyridin-2-yl)-allyl | H | H | F | H |
| I-251 | 3-(5-chloro-pyridin-2-yl)-allyl | H | H | F | H |
| I-252 | 3-pyridin-4-yl-allyl | H | H | F | H |
| I-253 | 3-(2-Chloro-pyridin-4-yl)-allyl | H | H | F | H |
| I-254 | 4-chlorobenzyl | H | H | Br | H |
| I-255 | Cinnamyl | H | H | Br | H |
| I-256 | 4-chlorocinnamyl | H | H | Br | H |
| I-257 | 4-fluorocinnamyl | H | H | Br | H |
| I-258 | 4-bromocinnamyl | H | H | Br | H |
| I-259 | 4-trifluoromethylcinnamyl | H | H | Br | H |
| I-260 | 4-trifluoromethoxycinnamyl | H | H | Br | H |
| I-261 | 4-pentafluoroethoxycinnamyl | H | H | Br | H |
| I-262 | 4-methoxycinnamyl | H | H | Br | H |
| I-263 | 4-ethoxycinnamyl | H | H | Br | H |
| I-264 | 4-cyanocinnamyl | H | H | Br | H |
| I-265 | 3-(6-chloro-pyridin-3-yl)-allyl | H | H | Br | H |
| I-266 | 3-(4-chlorophenyl)-but-2-enyl | H | H | Br | H |
| I-267 | 3-(4-chlorophenyl)-3-fluoro-allyl | H | H | Br | H |
| I-268 | 3-chloro-4-fluoro-cinnamyl | H | H | Br | H |
| I-269 | 3,5-dichloro-cinnamyl | H | H | Br | H |
| I-270 | 5-phenyl-penta-2,4-dienyl | H | H | Br | H |
| I-271 | 4-isopropyloxycarbonylamino-cinnamyl | H | H | Br | H |
| I-272 | 3-naphthalen-2-yl-allyl | H | H | Br | H |
| I-273 | 3-(5-trifluoromethyl-pyridin-2-yl)-allyl | H | H | Br | H |
| I-274 | 3-(5-chloro-pyridin-2-yl)-allyl | H | H | Br | H |
| I-275 | 3-pyridin-4-yl-allyl | H | H | Br | H |
| I-276 | 3-(2-Chloro-pyridin-4-yl)-allyl | H | H | Br | H |
| I-277 | 4-chlorobenzyl | H | H | OCF₃ | H |

TABLE 1-continued

| Compound No | R⁸ | R⁴ᵃ | R⁴ᵇ | R⁴ᶜ | R⁴ᵈ |
|---|---|---|---|---|---|
| I-278 | Cinnamyl | H | H | OCF₃ | H |
| I-279 | 4-chlorocinnamyl | H | H | OCF₃ | H |
| I-280 | 4-fluorocinnamyl | H | H | OCF₃ | H |
| I-281 | 4-bromocinnamyl | H | H | OCF₃ | H |
| I-282 | 4-trifluoromethylcinnamyl | H | H | OCF₃ | H |
| I-283 | 4-trifluoromethoxycinnamyl | H | H | OCF₃ | H |
| I-284 | 4-pentafluoroethoxycinnamyl | H | H | OCF₃ | H |
| I-285 | 4-methoxycinnamyl | H | H | OCF₃ | H |
| I-286 | 4-ethoxycinnamyl | H | H | OCF₃ | H |
| I-287 | 4-cyanocinnamyl | H | H | OCF₃ | H |
| I-288 | 3-(6-chloro-pyridin-3-yl)-allyl | H | H | OCF₃ | H |
| I-289 | 3-(4-chlorophenyl)-but-2-enyl | H | H | OCF₃ | H |
| I-290 | 3-(4-chlorophenyl)-3-fluoro-allyl | H | H | OCF₃ | H |
| I-291 | 3-chloro-4-fluoro-cinnamyl | H | H | OCF₃ | H |
| I-292 | 3,5-dichloro-cinnamyl | H | H | OCF₃ | H |
| I-293 | 5-phenyl-penta-2,4-dienyl | H | H | OCF₃ | H |
| I-294 | 4-isopropyloxycarbonylamino-cinnamyl | H | H | OCF₃ | H |
| I-295 | 3-naphthalen-2-yl-allyl | H | H | OCF₃ | H |
| I-296 | 3-(5-trifluoromethyl-pyridin-2-yl)-allyl | H | H | OCF₃ | H |
| I-297 | 3-(5-chloro-pyridin-2-yl)-allyl | H | H | OCF₃ | H |
| I-298 | 3-pyridin-4-yl-allyl | H | H | OCF₃ | H |
| I-299 | 3-(2-Chloro-pyridin-4-yl)-allyl | H | H | OCF₃ | H |
| I-300 | 4-chlorobenzyl | H | H | CH₃ | H |
| I-301 | Cinnamyl | H | H | CH₃ | H |
| I-302 | 4-chlorocinnamyl | H | H | CH₃ | H |
| I-303 | 4-fluorocinnamyl | H | H | CH₃ | H |
| I-304 | 4-bromocinnamyl | H | H | CH₃ | H |
| I-305 | 4-trifluoromethylcinnamyl | H | H | CH₃ | H |
| I-306 | 4-trifluoromethoxycinnamyl | H | H | CH₃ | H |
| I-307 | 4-pentafluoroethoxycinnamyl | H | H | CH₃ | H |
| I-308 | 4-methoxycinnamyl | H | H | CH₃ | H |
| I-309 | 4-ethoxycinnamyl | H | H | CH₃ | H |
| I-310 | 4-cyanocinnamyl | H | H | CH₃ | H |
| I-311 | 3-(6-chloro-pyridin-3-yl)-allyl | H | H | CH₃ | H |
| I-312 | 3-(4-chlorophenyl)-but-2-enyl | H | H | CH₃ | H |
| I-313 | 3-(4-chlorophenyl)-3-fluoro-allyl | H | H | CH₃ | H |
| I-314 | 3-chloro-4-fluoro-cinnamyl | H | H | CH₃ | H |
| I-315 | 3,5-dichloro-cinnamyl | H | H | CH₃ | H |
| I-316 | 5-phenyl-penta-2,4-dienyl | H | H | CH₃ | H |
| I-317 | 4-isopropyloxycarbonylamino-cinnamyl | H | H | CH₃ | H |
| I-318 | 3-naphthalen-2-yl-allyl | H | H | CH₃ | H |
| I-319 | 3-(5-trifluoromethyl-pyridin-2-yl)-allyl | H | H | CH₃ | H |
| I-320 | 3-(5-chloro-pyridin-2-yl)-allyl | H | H | CH₃ | H |
| I-321 | 3-pyridin-4-yl-allyl | H | H | CH₃ | H |
| I-322 | 3-(2-Chloro-pyridin-4-yl)-allyl | H | H | CH₃ | H |
| I-323 | 4-chlorobenzyl | H | H | CF₃ | H |
| I-324 | Cinnamyl | H | H | CF₃ | H |
| I-325 | 4-chlorocinnamyl | H | H | CF₃ | H |
| I-326 | 4-fluorocinnamyl | H | H | CF₃ | H |
| I-327 | 4-bromocinnamyl | H | H | CF₃ | H |
| I-328 | 4-trifluoromethylcinnamyl | H | H | CF₃ | H |
| I-329 | 4-trifluoromethoxycinnamyl | H | H | CF₃ | H |
| I-330 | 4-pentafluoroethoxycinnamyl | H | H | CF₃ | H |
| I-331 | 4-methoxycinnamyl | H | H | CF₃ | H |
| I-332 | 4-ethoxycinnamyl | H | H | CF₃ | H |
| I-333 | 4-cyanocinnamyl | H | H | CF₃ | H |
| I-334 | 3-(6-chloro-pyridin-3-yl)-allyl | H | H | CF₃ | H |
| I-335 | 3-(4-chlorophenyl)-but-2-enyl | H | H | CF₃ | H |
| I-336 | 3-(4-chlorophenyl)-3-fluoro-allyl | H | H | CF₃ | H |
| I-337 | 3-chloro-4-fluoro-cinnamyl | H | H | CF₃ | H |
| I-338 | 3,5-dichloro-cinnamyl | H | H | CF₃ | H |
| I-339 | 5-phenyl-penta-2,4-dienyl | H | H | CF₃ | H |
| I-340 | 4-isopropyloxycarbonylamino-cinnamyl | H | H | CF₃ | H |
| I-341 | 3-naphthalen-2-yl-allyl | H | H | CF₃ | H |
| I-342 | 3-(5-trifluoromethyl-pyridin-2-yl)-allyl | H | H | CF₃ | H |
| I-343 | 3-(5-chloro-pyridin-2-yl)-allyl | H | H | CF₃ | H |
| I-344 | 3-pyridin-4-yl-allyl | H | H | CF₃ | H |
| I-345 | 3-(2-Chloro-pyridin-4-yl)-allyl | H | H | CF₃ | H |
| I-346 | 4-chlorobenzyl | F | H | H | H |
| I-347 | Cinnamyl | F | H | H | H |
| I-348 | 4-chlorocinnamyl | F | H | H | H |
| I-349 | 4-fluorocinnamyl | F | H | H | H |
| I-350 | 4-bromocinnamyl | F | H | H | H |
| I-351 | 4-trifluoromethylcinnamyl | F | H | H | H |
| I-352 | 4-trifluoromethoxycinnamyl | F | H | H | H |
| I-353 | 4-pentafluoroethoxycinnamyl | F | H | H | H |
| I-354 | 4-methoxycinnamyl | F | H | H | H |

TABLE 1-continued

| Compound No | R⁸ | R⁴ᵃ | R⁴ᵇ | R⁴ᶜ | R⁴ᵈ |
|---|---|---|---|---|---|
| I-355 | 4-ethoxycinnamyl | F | H | H | H |
| I-356 | 4-cyanocinnamyl | F | H | H | H |
| I-357 | 3-(6-chloro-pyridin-3-yl)-allyl | F | H | H | H |
| I-358 | 3-(4-chlorophenyl)-but-2-enyl | F | H | H | H |
| I-359 | 3-(4-chlorophenyl)-3-fluoro-allyl | F | H | H | H |
| I-360 | 3-chloro-4-fluoro-cinnamyl | F | H | H | H |
| I-361 | 3,5-dichloro-cinnamyl | F | H | H | H |
| I-362 | 5-phenyl-penta-2,4-dienyl | F | H | H | H |
| I-363 | 4-isopropyloxycarbonylamino-cinnamyl | F | H | H | H |
| I-364 | 3-naphthalen-2-yl-allyl | F | H | H | H |
| I-365 | 3-(5-trifluoromethyl-pyridin-2-yl)-allyl | F | H | H | H |
| I-366 | 3-(5-chloro-pyridin-2-yl)-allyl | F | H | H | H |
| I-367 | 3-pyridin-4-yl-allyl | F | H | H | H |
| I-368 | 3-(2-Chloro-pyridin-4-yl)-allyl | F | H | H | H |
| I-369 | 4-chlorobenzyl | Cl | H | H | H |
| I-370 | Cinnamyl | Cl | H | H | H |
| I-371 | 4-chlorocinnamyl | Cl | H | H | H |
| I-372 | 4-fluorocinnamyl | Cl | H | H | H |
| I-373 | 4-bromocinnamyl | Cl | H | H | H |
| I-374 | 4-trifluoromethylcinnamyl | Cl | H | H | H |
| I-375 | 4-trifluoromethoxycinnamyl | Cl | H | H | H |
| I-376 | 4-pentafluoroethoxycinnamyl | Cl | H | H | H |
| I-377 | 4-methoxycinnamyl | Cl | H | H | H |
| I-378 | 4-ethoxycinnamyl | Cl | H | H | H |
| I-379 | 4-cyanocinnamyl | Cl | H | H | H |
| I-380 | 3-(6-chloro-pyridin-3-yl)-allyl | Cl | H | H | H |
| I-381 | 3-(4-chlorophenyl)-but-2-enyl | Cl | H | H | H |
| I-382 | 3-(4-chlorophenyl)-3-fluoro-allyl | Cl | H | H | H |
| I-383 | 3-chloro-4-fluoro-cinnamyl | Cl | H | H | H |
| I-384 | 3,5-dichloro-cinnamyl | Cl | H | H | H |
| I-385 | 5-phenyl-penta-2,4-dienyl | Cl | H | H | H |
| I-386 | 4-isopropyloxycarbonylamino-cinnamyl | Cl | H | H | H |
| I-387 | 3-naphthalen-2-yl-allyl | Cl | H | H | H |
| I-388 | 3-(5-trifluoromethyl-pyridin-2-yl)-allyl | Cl | H | H | H |
| I-389 | 3-(5-chloro-pyridin-2-yl)-allyl | Cl | H | H | H |
| I-390 | 3-pyridin-4-yl-allyl | Cl | H | H | H |
| I-391 | 3-(2-Chloro-pyridin-4-yl)-allyl | Cl | H | H | H |
| I-392 | 4-chlorobenzyl | Br | H | H | H |
| I-393 | Cinnamyl | Br | H | H | H |
| I-394 | 4-chlorocinnamyl | Br | H | H | H |
| I-395 | 4-fluorocinnamyl | Br | H | H | H |
| I-396 | 4-bromocinnamyl | Br | H | H | H |
| I-397 | 4-trifluoromethylcinnamyl | Br | H | H | H |
| I-398 | 4-trifluoromethoxycinnamyl | Br | H | H | H |
| I-399 | 4-pentafluoroethoxycinnamyl | Br | H | H | H |
| I-400 | 4-methoxycinnamyl | Br | H | H | H |
| I-401 | 4-ethoxycinnamyl | Br | H | H | H |
| I-402 | 4-cyanocinnamyl | Br | H | H | H |
| I-403 | 3-(6-chloro-pyridin-3-yl)-allyl | Br | H | H | H |
| I-404 | 3-(4-chlorophenyl)-but-2-enyl | Br | H | H | H |
| I-405 | 3-(4-chlorophenyl)-3-fluoro-allyl | Br | H | H | H |
| I-406 | 3-chloro-4-fluoro-cinnamyl | Br | H | H | H |
| I-407 | 3,5-dichloro-cinnamyl | Br | H | H | H |
| I-408 | 5-phenyl-penta-2,4-dienyl | Br | H | H | H |
| I-409 | 4-isopropyloxycarbonylamino-cinnamyl | Br | H | H | H |
| I-410 | 3-naphthalen-2-yl-allyl | Br | H | H | H |
| I-411 | 3-(5-trifluoromethyl-pyridin-2-yl)-allyl | Br | H | H | H |
| I-412 | 3-(5-chloro-pyridin-2-yl)-allyl | Br | H | H | H |
| I-413 | 3-pyridin-4-yl-allyl | Br | H | H | H |
| I-414 | 3-(2-Chloro-pyridin-4-yl)-allyl | Br | H | H | H |
| I-415 | 4-chlorobenzyl | $CF_3$ | H | H | H |
| I-416 | Cinnamyl | $CF_3$ | H | H | H |
| I-417 | 4-chlorocinnamyl | $CF_3$ | H | H | H |
| I-418 | 4-fluorocinnamyl | $CF_3$ | H | H | H |
| I-419 | 4-bromocinnamyl | $CF_3$ | H | H | H |
| I-420 | 4-trifluoromethylcinnamyl | $CF_3$ | H | H | H |
| I-421 | 4-trifluoromethoxycinnamyl | $CF_3$ | H | H | H |
| I-422 | 4-pentafluoroethoxycinnamyl | $CF_3$ | H | H | H |
| I-423 | 4-methoxycinnamyl | $CF_3$ | H | H | H |
| I-424 | 4-ethoxycinnamyl | $CF_3$ | H | H | H |
| I-425 | 4-cyanocinnamyl | $CF_3$ | H | H | H |
| I-426 | 3-(6-chloro-pyridin-3-yl)-allyl | $CF_3$ | H | H | H |
| I-427 | 3-(4-chlorophenyl)-but-2-enyl | $CF_3$ | H | H | H |
| I-428 | 3-(4-chlorophenyl)-3-fluoro-allyl | $CF_3$ | H | H | H |
| I-429 | 3-chloro-4-fluoro-cinnamyl | $CF_3$ | H | H | H |
| I-430 | 3,5-dichloro-cinnamyl | $CF_3$ | H | H | H |
| I-431 | 5-phenyl-penta-2,4-dienyl | $CF_3$ | H | H | H |

TABLE 1-continued

| Compound No | R⁸ | R⁴ᵃ | R⁴ᵇ | R⁴ᶜ | R⁴ᵈ |
|---|---|---|---|---|---|
| I-432 | 4-isopropyloxycarbonylamino-cinnamyl | CF₃ | H | H | H |
| I-433 | 3-naphthalen-2-yl-allyl | CF₃ | H | H | H |
| I-434 | 3-(5-trifluoromethyl-pyridin-2-yl)-allyl | CF₃ | H | H | H |
| I-435 | 3-(5-chloro-pyridin-2-yl)-allyl | CF₃ | H | H | H |
| I-436 | 3-pyridin-4-yl-allyl | CF₃ | H | H | H |
| I-437 | 3-(2-Chloro-pyridin-4-yl)-allyl | CF₃ | H | H | H |
| I-438 | 4-chlorobenzyl | H | H | H | F |
| I-439 | Cinnamyl | H | H | H | F |
| I-440 | 4-chlorocinnamyl | H | H | H | F |
| I-441 | 4-fluorocinnamyl | H | H | H | F |
| I-442 | 4-bromocinnamyl | H | H | H | F |
| I-443 | 4-trifluoromethylcinnamyl | H | H | H | F |
| I-444 | 4-trifluoromethoxycinnamyl | H | H | H | F |
| I-445 | 4-pentafluoroethoxycinnamyl | H | H | H | F |
| I-446 | 4-methoxycinnamyl | H | H | H | F |
| I-447 | 4-ethoxycinnamyl | H | H | H | F |
| I-448 | 4-cyanocinnamyl | H | H | H | F |
| I-449 | 3-(6-chloro-pyridin-3-yl)-allyl | H | H | H | F |
| I-450 | 3-(4-chlorophenyl)-but-2-enyl | H | H | H | F |
| I-451 | 3-(4-chlorophenyl)-3-fluoro-allyl | H | H | H | F |
| I-452 | 3-chloro-4-fluoro-cinnamyl | H | H | H | F |
| I-453 | 3,5-dichloro-cinnamyl | H | H | H | F |
| I-454 | 5-phenyl-penta-2,4-dienyl | H | H | H | F |
| I-455 | 4-isopropyloxycarbonylamino-cinnamyl | H | H | H | F |
| I-456 | 3-naphthalen-2-yl-allyl | H | H | H | F |
| I-457 | 3-(5-trifluoromethyl-pyridin-2-yl)-allyl | H | H | H | F |
| I-458 | 3-(5-chloro-pyridin-2-yl)-allyl | H | H | H | F |
| I-459 | 3-pyridin-4-yl-allyl | H | H | H | F |
| I-460 | 3-(2-Chloro-pyridin-4-yl)-allyl | H | H | H | F |
| I-461 | 4-chlorobenzyl | H | H | H | Cl |
| I-462 | Cinnamyl | H | H | H | Cl |
| I-463 | 4-chlorocinnamyl | H | H | H | Cl |
| I-464 | 4-fluorocinnamyl | H | H | H | Cl |
| I-465 | 4-bromocinnamyl | H | H | H | Cl |
| I-466 | 4-trifluoromethylcinnamyl | H | H | H | Cl |
| I-467 | 4-trifluoromethoxycinnamyl | H | H | H | Cl |
| I-468 | 4-pentafluoroethoxycinnamyl | H | H | H | Cl |
| I-469 | 4-methoxycinnamyl | H | H | H | Cl |
| I-470 | 4-ethoxycinnamyl | H | H | H | Cl |
| I-471 | 4-cyanocinnamyl | H | H | H | Cl |
| I-472 | 3-(6-chloro-pyridin-3-yl)-allyl | H | H | H | Cl |
| I-473 | 3-(4-chlorophenyl)-but-2-enyl | H | H | H | Cl |
| I-474 | 3-(4-chlorophenyl)-3-fluoro-allyl | H | H | H | Cl |
| I-475 | 3-chloro-4-fluoro-cinnamyl | H | H | H | Cl |
| I-476 | 3,5-dichloro-cinnamyl | H | H | H | Cl |
| I-477 | 5-phenyl-penta-2,4-dienyl | H | H | H | Cl |
| I-478 | 4-isopropyloxycarbonylamino-cinnamyl | H | H | H | Cl |
| I-479 | 3-naphthalen-2-yl-allyl | H | H | H | Cl |
| I-480 | 3-(5-trifluoromethyl-pyridin-2-yl)-allyl | H | H | H | Cl |
| I-481 | 3-(5-chloro-pyridin-2-yl)-allyl | H | H | H | Cl |
| I-482 | 3-pyridin-4-yl-allyl | H | H | H | Cl |
| I-483 | 3-(2-Chloro-pyridin-4-yl)-allyl | H | H | H | Cl |
| I-484 | 4-chlorobenzyl | H | F | F | H |
| I-485 | Cinnamyl | H | F | F | H |
| I-486 | 4-chlorocinnamyl | H | F | F | H |
| I-487 | 4-fluorocinnamyl | H | F | F | H |
| I-488 | 4-bromocinnamyl | H | F | F | H |
| I-489 | 4-trifluoromethylcinnamyl | H | F | F | H |
| I-490 | 4-trifluoromethoxycinnamyl | H | F | F | H |
| I-491 | 4-pentafluoroethoxycinnamyl | H | F | F | H |
| I-492 | 4-methoxycinnamyl | H | F | F | H |
| I-493 | 4-ethoxycinnamyl | H | F | F | H |
| I-494 | 4-cyanocinnamyl | H | F | F | H |
| I-495 | 3-(6-chloro-pyridin-3-yl)-allyl | H | F | F | H |
| I-496 | 3-(4-chlorophenyl)-but-2-enyl | H | F | F | H |
| I-497 | 3-(4-chlorophenyl)-3-fluoro-allyl | H | F | F | H |
| I-498 | 3-chloro-4-fluoro-cinnamyl | H | F | F | H |
| I-499 | 3,5-dichloro-cinnamyl | H | F | F | H |
| I-500 | 5-phenyl-penta-2,4-dienyl | H | F | F | H |
| I-501 | 4-isopropyloxycarbonylamino-cinnamyl | H | F | F | H |
| I-502 | 3-naphthalen-2-yl-allyl | H | F | F | H |
| I-503 | 3-(5-trifluoromethyl-pyridin-2-yl)-allyl | H | F | F | H |
| I-504 | 3-(5-chloro-pyridin-2-yl)-allyl | H | F | F | H |
| I-505 | 3-pyridin-4-yl-allyl | H | F | F | H |
| I-506 | 3-(2-Chloro-pyridin-4-yl)-allyl | H | F | F | H |
| I-507 | 4-chlorobenzyl | H | F | Cl | H |
| I-508 | Cinnamyl | H | F | Cl | H |

TABLE 1-continued

| Compound No | R⁸ | R⁴ᵃ | R⁴ᵇ | R⁴ᶜ | R⁴ᵈ |
|---|---|---|---|---|---|
| I-509 | 4-chlorocinnamyl | H | F | Cl | H |
| I-510 | 4-fluorocinnamyl | H | F | Cl | H |
| I-511 | 4-bromocinnamyl | H | F | Cl | H |
| I-512 | 4-trifluoromethylcinnamyl | H | F | Cl | H |
| I-513 | 4-trifluoromethoxycinnamyl | H | F | Cl | H |
| I-514 | 4-pentafluoroethoxycinnamyl | H | F | Cl | H |
| I-515 | 4-methoxycinnamyl | H | F | Cl | H |
| I-516 | 4-ethoxycinnamyl | H | F | Cl | H |
| I-517 | 4-cyanocinnamyl | H | F | Cl | H |
| I-518 | 3-(6-chloro-pyridin-3-yl)-allyl | H | F | Cl | H |
| I-519 | 3-(4-chlorophenyl)-but-2-enyl | H | F | Cl | H |
| I-520 | 3-(4-chlorophenyl)-3-fluoro-allyl | H | F | Cl | H |
| I-521 | 3-chloro-4-fluoro-cinnamyl | H | F | Cl | H |
| I-522 | 3,5-dichloro-cinnamyl | H | F | Cl | H |
| I-523 | 5-phenyl-penta-2,4-dienyl | H | F | Cl | H |
| I-524 | 4-isopropyloxycarbonylamino-cinnamyl | H | F | Cl | H |
| I-525 | 3-naphthalen-2-yl-allyl | H | F | Cl | H |
| I-526 | 3-(5-trifluoromethyl-pyridin-2-yl)-allyl | H | F | Cl | H |
| I-527 | 3-(5-chloro-pyridin-2-yl)-allyl | H | F | Cl | H |
| I-528 | 3-pyridin-4-yl-allyl | H | F | Cl | H |
| I-529 | 3-(2-Chloro-pyridin-4-yl)-allyl | H | F | Cl | H |
| I-530 | 4-chlorobenzyl | H | Cl | F | H |
| I-531 | Cinnamyl | H | Cl | F | H |
| I-532 | 4-chlorocinnamyl | H | Cl | F | H |
| I-533 | 4-fluorocinnamyl | H | Cl | F | H |
| I-534 | 4-bromocinnamyl | H | Cl | F | H |
| I-535 | 4-trifluoromethylcinnamyl | H | Cl | F | H |
| I-536 | 4-trifluoromethoxycinnamyl | H | Cl | F | H |
| I-537 | 4-pentafluoroethoxycinnamyl | H | Cl | F | H |
| I-538 | 4-methoxycinnamyl | H | Cl | F | H |
| I-539 | 4-ethoxycinnamyl | H | Cl | F | H |
| I-540 | 4-cyanocinnamyl | H | Cl | F | H |
| I-541 | 3-(6-chloro-pyridin-3-yl)-allyl | H | Cl | F | H |
| I-542 | 3-(4-chlorophenyl)-but-2-enyl | H | Cl | F | H |
| I-543 | 3-(4-chlorophenyl)-3-fluoro-allyl | H | Cl | F | H |
| I-544 | 3-chloro-4-fluoro-cinnamyl | H | Cl | F | H |
| I-545 | 3,5-dichloro-cinnamyl | H | Cl | F | H |
| I-546 | 5-phenyl-penta-2,4-dienyl | H | Cl | F | H |
| I-547 | 4-isopropyloxycarbonylamino-cinnamyl | H | Cl | F | H |
| I-548 | 3-naphthalen-2-yl-allyl | H | Cl | F | H |
| I-549 | 3-(5-trifluoromethyl-pyridin-2-yl)-allyl | H | Cl | F | H |
| I-550 | 3-(5-chloro-pyridin-2-yl)-allyl | H | Cl | F | H |
| I-551 | 3-pyridin-4-yl-allyl | H | Cl | F | H |
| I-552 | 3-(2-Chloro-pyridin-4-yl)-allyl | H | Cl | F | H |
| I-553 | 4-chlorobenzyl | H | Cl | Cl | H |
| I-554 | Cinnamyl | H | Cl | Cl | H |
| I-555 | 4-chlorocinnamyl | H | Cl | Cl | H |
| I-556 | 4-fluorocinnamyl | H | Cl | Cl | H |
| I-557 | 4-bromocinnamyl | H | Cl | Cl | H |
| I-558 | 4-trifluoromethylcinnamyl | H | Cl | Cl | H |
| I-559 | 4-trifluoromethoxycinnamyl | H | Cl | Cl | H |
| I-560 | 4-pentafluoroethoxycinnamyl | H | Cl | Cl | H |
| I-561 | 4-methoxycinnamyl | H | Cl | Cl | H |
| I-562 | 4-ethoxycinnamyl | H | Cl | Cl | H |
| I-563 | 4-cyanocinnamyl | H | Cl | Cl | H |
| I-564 | 3-(6-chloro-pyridin-3-yl)-allyl | H | Cl | Cl | H |
| I-565 | 3-(4-chlorophenyl)-but-2-enyl | H | Cl | Cl | H |
| I-566 | 3-(4-chlorophenyl)-3-fluoro-allyl | H | Cl | Cl | H |
| I-567 | 3-chloro-4-fluoro-cinnamyl | H | Cl | Cl | H |
| I-568 | 3,5-dichloro-cinnamyl | H | Cl | Cl | H |
| I-569 | 5-phenyl-penta-2,4-dienyl | H | Cl | Cl | H |
| I-570 | 4-isopropyloxycarbonylamino-cinnamyl | H | Cl | Cl | H |
| I-571 | 3-naphthalen-2-yl-allyl | H | Cl | Cl | H |
| I-572 | 3-(5-trifluoromethyl-pyridin-2-yl)-allyl | H | Cl | Cl | H |
| I-573 | 3-(5-chloro-pyridin-2-yl)-allyl | H | Cl | Cl | H |
| I-574 | 3-pyridin-4-yl-allyl | H | Cl | Cl | H |
| I-575 | 3-(2-Chloro-pyridin-4-yl)-allyl | H | Cl | Cl | H |
| I-576 | 4-chlorobenzyl | H | —OCF₂O— | | H |
| I-577 | Cinnamyl | H | —OCF₂O— | | H |
| I-578 | 4-chlorocinnamyl | H | —OCF₂O— | | H |
| I-579 | 4-fluorocinnamyl | H | —OCF₂O— | | H |
| I-580 | 4-bromocinnamyl | H | —OCF₂O— | | H |
| I-581 | 4-trifluoromethylcinnamyl | H | —OCF₂O— | | H |
| I-582 | 4-trifluoromethoxycinnamyl | H | —OCF₂O— | | H |
| I-583 | 4-pentafluoroethoxycinnamyl | H | —OCF₂O— | | H |
| I-584 | 4-methoxycinnamyl | H | —OCF₂O— | | H |
| I-585 | 4-ethoxycinnamyl | H | —OCF₂O— | | H |

TABLE 1-continued

| Compound No | R⁸ | R⁴ᵃ | R⁴ᵇ | R⁴ᶜ | R⁴ᵈ |
|---|---|---|---|---|---|
| I-586 | 4-cyanocinnamyl | H | —OCF₂O— | | H |
| I-587 | 3-(6-chloro-pyridin-3-yl)-allyl | H | —OCF₂O— | | H |
| I-588 | 3-(4-chlorophenyl)-but-2-enyl | H | —OCF₂O— | | H |
| I-589 | 3-(4-chlorophenyl)-3-fluoro-allyl | H | —OCF₂O— | | H |
| I-590 | 3-chloro-4-fluoro-cinnamyl | H | —OCF₂O— | | H |
| I-591 | 3,5-dichloro-cinnamyl | H | —OCF₂O— | | H |
| I-592 | 5-phenyl-penta-2,4-dienyl | H | —OCF₂O— | | H |
| I-593 | 4-isopropyloxycarbonylamino-cinnamyl | H | —OCF₂O— | | H |
| I-594 | 3-naphthalen-2-yl-allyl | H | —OCF₂O— | | H |
| I-595 | 3-(5-trifluoromethyl-pyridin-2-yl)-allyl | H | —OCF₂O— | | H |
| I-596 | 3-(5-chloro-pyridin-2-yl)-allyl | H | —OCF₂O— | | H |
| I-597 | 3-pyridin-4-yl-allyl | H | —OCF₂O— | | H |
| I-598 | 3-(2-Chloro-pyridin-4-yl)-allyl | H | —OCF₂O— | | H |
| I-599 | 4-chlorobenzyl | H | —C₄H₄— | | H |
| I-600 | Cinnamyl | H | —C₄H₄— | | H |
| I-601 | 4-chlorocinnamyl | H | —C₄H₄— | | H |
| I-602 | 4-fluorocinnamyl | H | —C₄H₄— | | H |
| I-603 | 4-bromocinnamyl | H | —C₄H₄— | | H |
| I-604 | 4-trifluoromethylcinnamyl | H | —C₄H₄— | | H |
| I-605 | 4-trifluoromethoxycinnamyl | H | —C₄H₄— | | H |
| I-606 | 4-pentafluoroethoxycinnamyl | H | —C₄H₄— | | H |
| I-607 | 4-methoxycinnamyl | H | —C₄H₄— | | H |
| I-608 | 4-ethoxycinnamyl | H | —C₄H₄— | | H |
| I-609 | 4-cyanocinnamyl | H | —C₄H₄— | | H |
| I-610 | 3-(6-chloro-pyridin-3-yl)-allyl | H | —C₄H₄— | | H |
| I-611 | 3-(4-chlorophenyl)-but-2-enyl | H | —C₄H₄— | | H |
| I-612 | 3-(4-chlorophenyl)-3-fluoro-allyl | H | —C₄H₄— | | H |
| I-613 | 3-chloro-4-fluoro-cinnamyl | H | —C₄H₄— | | H |
| I-614 | 3,5-dichloro-cinnamyl | H | —C₄H₄— | | H |
| I-615 | 5-phenyl-penta-2,4-dienyl | H | —C₄H₄— | | H |
| I-616 | 4-isopropyloxycarbonylamino-cinnamyl | H | —C₄H₄— | | H |
| I-617 | 3-naphthalen-2-yl-allyl | H | —C₄H₄— | | H |
| I-618 | 3-(5-trifluoromethyl-pyridin-2-yl)-allyl | H | —C₄H₄— | | H |
| I-619 | 3-(5-chloro-pyridin-2-yl)-allyl | H | —C₄H₄— | | H |
| I-620 | 3-pyridin-4-yl-allyl | H | —C₄H₄— | | H |
| I-621 | 3-(2-Chloro-pyridin-4-yl)-allyl | H | —C₄H₄— | | H |
| I-622 | 4-chlorobenzyl | Cl | H | Cl | H |
| I-623 | Cinnamyl | Cl | H | Cl | H |
| I-624 | 4-chlorocinnamyl | Cl | H | Cl | H |
| I-625 | 4-fluorocinnamyl | Cl | H | Cl | H |
| I-626 | 4-bromocinnamyl | Cl | H | Cl | H |
| I-627 | 4-trifluoromethylcinnamyl | Cl | H | Cl | H |
| I-628 | 4-trifluoromethoxycinnamyl | Cl | H | Cl | H |
| I-629 | 4-pentafluoroethoxycinnamyl | Cl | H | Cl | H |
| I-630 | 4-methoxycinnamyl | Cl | H | Cl | H |
| I-631 | 4-ethoxycinnamyl | Cl | H | Cl | H |
| I-632 | 4-cyanocinnamyl | Cl | H | Cl | H |
| I-633 | 3-(6-chloro-pyridin-3-yl)-allyl | Cl | H | Cl | H |
| I-634 | 3-(4-chlorophenyl)-but-2-enyl | Cl | H | Cl | H |
| I-635 | 3-(4-chlorophenyl)-3-fluoro-allyl | Cl | H | Cl | H |
| I-636 | 3-chloro-4-fluoro-cinnamyl | Cl | H | Cl | H |
| I-637 | 3,5-dichloro-cinnamyl | Cl | H | Cl | H |
| I-638 | 5-phenyl-penta-2,4-dienyl | Cl | H | Cl | H |
| I-639 | 4-isopropyloxycarbonylamino-cinnamyl | Cl | H | Cl | H |
| I-640 | 3-naphthalen-2-yl-allyl | Cl | H | Cl | H |
| I-641 | 3-(5-trifluoromethyl-pyridin-2-yl)-allyl | Cl | H | Cl | H |
| I-642 | 3-(5-chloro-pyridin-2-yl)-allyl | Cl | H | Cl | H |
| I-643 | 3-pyridin-4-yl-allyl | Cl | H | Cl | H |
| I-644 | 3-(2-Chloro-pyridin-4-yl)-allyl | Cl | H | Cl | H |
| I-645 | 4-chlorobenzyl | Cl | Cl | H | H |
| I-646 | Cinnamyl | Cl | Cl | H | H |
| I-647 | 4-chlorocinnamyl | Cl | Cl | H | H |
| I-648 | 4-fluorocinnamyl | Cl | Cl | H | H |
| I-649 | 4-bromocinnamyl | Cl | Cl | H | H |
| I-650 | 4-trifluoromethylcinnamyl | Cl | Cl | H | H |
| I-651 | 4-trifluoromethoxycinnamyl | Cl | Cl | H | H |
| I-652 | 4-pentafluoroethoxycinnamyl | Cl | Cl | H | H |
| I-653 | 4-methoxycinnamyl | Cl | Cl | H | H |
| I-654 | 4-ethoxycinnamyl | Cl | Cl | H | H |
| I-655 | 4-cyanocinnamyl | Cl | Cl | H | H |
| I-656 | 3-(6-chloro-pyridin-3-yl)-allyl | Cl | Cl | H | H |
| I-657 | 3-(4-chlorophenyl)-but-2-enyl | Cl | Cl | H | H |
| I-658 | 3-(4-chlorophenyl)-3-fluoro-allyl | Cl | Cl | H | H |
| I-659 | 3-chloro-4-fluoro-cinnamyl | Cl | Cl | H | H |
| I-660 | 3,5-dichloro-cinnamyl | Cl | Cl | H | H |
| I-661 | 5-phenyl-penta-2,4-dienyl | Cl | Cl | H | H |
| I-662 | 4-isopropyloxycarbonylamino-cinnamyl | Cl | Cl | H | H |

TABLE 1-continued

| Compound No | R⁸ | R⁴ᵃ | R⁴ᵇ | R⁴ᶜ | R⁴ᵈ |
|---|---|---|---|---|---|
| I-663 | 3-naphthalen-2-yl-allyl | Cl | Cl | H | H |
| I-664 | 3-(5-trifluoromethyl-pyridin-2-yl)-allyl | Cl | Cl | H | H |
| I-665 | 3-(5-chloro-pyridin-2-yl)-allyl | Cl | Cl | H | H |
| I-666 | 3-pyridin-4-yl-allyl | Cl | Cl | H | H |
| I-667 | 3-(2-Chloro-pyridin-4-yl)-allyl | Cl | Cl | H | H |
| I-668 | 4-chlorobenzyl | H | Cl | H | Cl |
| I-669 | Cinnamyl | H | Cl | H | Cl |
| I-670 | 4-chlorocinnamyl | H | Cl | H | Cl |
| I-671 | 4-fluorocinnamyl | H | Cl | H | Cl |
| I-672 | 4-bromocinnamyl | H | Cl | H | Cl |
| I-673 | 4-trifluoromethylcinnamyl | H | Cl | H | Cl |
| I-674 | 4-trifluoromethoxycinnamyl | H | Cl | H | Cl |
| I-675 | 4-pentafluoroethoxycinnamyl | H | Cl | H | Cl |
| I-676 | 4-methoxycinnamyl | H | Cl | H | Cl |
| I-677 | 4-ethoxycinnamyl | H | Cl | H | Cl |
| I-678 | 4-cyanocinnamyl | H | Cl | H | Cl |
| I-679 | 3-(6-chloro-pyridin-3-yl)-allyl | H | Cl | H | Cl |
| I-680 | 3-(4-chlorophenyl)-but-2-enyl | H | Cl | H | Cl |
| I-681 | 3-(4-chlorophenyl)-3-fluoro-allyl | H | Cl | H | Cl |
| I-682 | 3-chloro-4-fluoro-cinnamyl | H | Cl | H | Cl |
| I-683 | 3,5-dichloro-cinnamyl | H | Cl | H | Cl |
| I-684 | 5-phenyl-penta-2,4-dienyl | H | Cl | H | Cl |
| I-685 | 4-isopropyloxycarbonylamino-cinnamyl | H | Cl | H | Cl |
| I-686 | 3-naphthalen-2-yl-allyl | H | Cl | H | Cl |
| I-687 | 3-(5-trifluoromethyl-pyridin-2-yl)-allyl | H | Cl | H | Cl |
| I-688 | 3-(5-chloro-pyridin-2-yl)-allyl | H | Cl | H | Cl |
| I-689 | 3-pyridin-4-yl-allyl | H | Cl | H | Cl |
| I-690 | 3-(2-Chloro-pyridin-4-yl)-allyl | H | Cl | H | Cl |
| I-691 | 4-chlorobenzyl | H | F | H | F |
| I-692 | Cinnamyl | H | F | H | F |
| I-693 | 4-chlorocinnamyl | H | F | H | F |
| I-694 | 4-fluorocinnamyl | H | F | H | F |
| I-695 | 4-bromocinnamyl | H | F | H | F |
| I-696 | 4-trifluoromethylcinnamyl | H | F | H | F |
| I-697 | 4-trifluoromethoxycinnamyl | H | F | H | F |
| I-698 | 4-pentafluoroethoxycinnamyl | H | F | H | F |
| I-699 | 4-methoxycinnamyl | H | F | H | F |
| I-700 | 4-ethoxycinnamyl | H | F | H | F |
| I-701 | 4-cyanocinnamyl | H | F | H | F |
| I-702 | 3-(6-chloro-pyridin-3-yl)-allyl | H | F | H | F |
| I-703 | 3-(4-chlorophenyl)-but-2-enyl | H | F | H | F |
| I-704 | 3-(4-chlorophenyl)-3-fluoro-allyl | H | F | H | F |
| I-705 | 3-chloro-4-fluoro-cinnamyl | H | F | H | F |
| I-706 | 3,5-dichloro-cinnamyl | H | F | H | F |
| I-707 | 5-phenyl-penta-2,4-dienyl | H | F | H | F |
| I-708 | 4-isopropyloxycarbonylamino-cinnamyl | H | F | H | F |
| I-709 | 3-naphthalen-2-yl-allyl | H | F | H | F |
| I-710 | 3-(5-trifluoromethyl-pyridin-2-yl)-allyl | H | F | H | F |
| I-711 | 3-(5-chloro-pyridin-2-yl)-allyl | H | F | H | F |
| I-712 | 3-pyridin-4-yl-allyl | H | F | H | F |
| I-713 | 3-(2-Chloro-pyridin-4-yl)-allyl | H | F | H | F |
| I-714 | 4-chlorobenzyl | F | H | F | H |
| I-715 | Cinnamyl | F | H | F | H |
| I-716 | 4-chlorocinnamyl | F | H | F | H |
| I-717 | 4-fluorocinnamyl | F | H | F | H |
| I-718 | 4-bromocinnamyl | F | H | F | H |
| I-719 | 4-trifluoromethylcinnamyl | F | H | F | H |
| I-720 | 4-trifluoromethoxycinnamyl | F | H | F | H |
| I-721 | 4-pentafluoroethoxycinnamyl | F | H | F | H |
| I-722 | 4-methoxycinnamyl | F | H | F | H |
| I-723 | 4-ethoxycinnamyl | F | H | F | H |
| I-724 | 4-cyanocinnamyl | F | H | F | H |
| I-725 | 3-(6-chloro-pyridin-3-yl)-allyl | F | H | F | H |
| I-726 | 3-(4-chlorophenyl)-but-2-enyl | F | H | F | H |
| I-727 | 3-(4-chlorophenyl)-3-fluoro-allyl | F | H | F | H |
| I-728 | 3-chloro-4-fluoro-cinnamyl | F | H | F | H |
| I-729 | 3,5-dichloro-cinnamyl | F | H | F | H |
| I-730 | 5-phenyl-penta-2,4-dienyl | F | H | F | H |
| I-731 | 4-isopropyloxycarbonylamino-cinnamyl | F | H | F | H |
| I-732 | 3-naphthalen-2-yl-allyl | F | H | F | H |
| I-733 | 3-(5-trifluoromethyl-pyridin-2-yl)-allyl | F | H | F | H |
| I-734 | 3-(5-chloro-pyridin-2-yl)-allyl | F | H | F | H |
| I-735 | 3-pyridin-4-yl-allyl | F | H | F | H |
| I-736 | 3-(2-Chloro-pyridin-4-yl)-allyl | F | H | F | H |
| I-737 | 4-chlorobenzyl | F | F | H | H |
| I-738 | Cinnamyl | F | F | H | H |
| I-739 | 4-chlorocinnamyl | F | F | H | H |

TABLE 1-continued

| Compound No | R⁸ | R⁴ᵃ | R⁴ᵇ | R⁴ᶜ | R⁴ᵈ |
|---|---|---|---|---|---|
| I-740 | 4-fluorocinnamyl | F | F | H | H |
| I-741 | 4-bromocinnamyl | F | F | H | H |
| I-742 | 4-trifluoromethylcinnamyl | F | F | H | H |
| I-743 | 4-trifluoromethoxycinnamyl | F | F | H | H |
| I-744 | 4-pentafluoroethoxycinnamyl | F | F | H | H |
| I-745 | 4-methoxycinnamyl | F | F | H | H |
| I-746 | 4-ethoxycinnamyl | F | F | H | H |
| I-747 | 4-cyanocinnamyl | F | F | H | H |
| I-748 | 3-(6-chloro-pyridin-3-yl)-allyl | F | F | H | H |
| I-749 | 3-(4-chlorophenyl)-but-2-enyl | F | F | H | H |
| I-750 | 3-(4-chlorophenyl)-3-fluoro-allyl | F | F | H | H |
| I-751 | 3-chloro-4-fluoro-cinnamyl | F | F | H | H |
| I-752 | 3,5-dichloro-cinnamyl | F | F | H | H |
| I-753 | 5-phenyl-penta-2,4-dienyl | F | F | H | H |
| I-754 | 4-isopropyloxycarbonylamino-cinnamyl | F | F | H | H |
| I-755 | 3-naphthalen-2-yl-allyl | F | F | H | H |
| I-756 | 3-(5-trifluoromethyl-pyridin-2-yl)-allyl | F | F | H | H |
| I-757 | 3-(5-chloro-pyridin-2-yl)-allyl | F | F | H | H |
| I-758 | 3-pyridin-4-yl-allyl | F | F | H | H |
| I-759 | 3-(2-Chloro-pyridin-4-yl)-allyl | F | F | H | H |
| I-760 | 4-chlorobenzyl | Cl | F | H | H |
| I-761 | Cinnamyl | Cl | F | H | H |
| I-762 | 4-chlorocinnamyl | Cl | F | H | H |
| I-763 | 4-fluorocinnamyl | Cl | F | H | H |
| I-764 | 4-bromocinnamyl | Cl | F | H | H |
| I-765 | 4-trifluoromethylcinnamyl | Cl | F | H | H |
| I-766 | 4-trifluoromethoxycinnamyl | Cl | F | H | H |
| I-767 | 4-pentafluoroethoxycinnamyl | Cl | F | H | H |
| I-768 | 4-methoxycinnamyl | Cl | F | H | H |
| I-769 | 4-ethoxycinnamyl | Cl | F | H | H |
| I-770 | 4-cyanocinnamyl | Cl | F | H | H |
| I-771 | 3-(6-chloro-pyridin-3-yl)-allyl | Cl | F | H | H |
| I-772 | 3-(4-chlorophenyl)-but-2-enyl | Cl | F | H | H |
| I-773 | 3-(4-chlorophenyl)-3-fluoro-allyl | Cl | F | H | H |
| I-774 | 3-chloro-4-fluoro-cinnamyl | Cl | F | H | H |
| I-775 | 3,5-dichloro-cinnamyl | Cl | F | H | H |
| I-776 | 5-phenyl-penta-2,4-dienyl | Cl | F | H | H |
| I-777 | 4-isopropyloxycarbonylamino-cinnamyl | Cl | F | H | H |
| I-778 | 3-naphthalen-2-yl-allyl | Cl | F | H | H |
| I-779 | 3-(5-trifluoromethyl-pyridin-2-yl)-allyl | Cl | F | H | H |
| I-780 | 3-(5-chloro-pyridin-2-yl)-allyl | Cl | F | H | H |
| I-781 | 3-pyridin-4-yl-allyl | Cl | F | H | H |
| I-782 | 3-(2-Chloro-pyridin-4-yl)-allyl | Cl | F | H | H |

Table II provides 782 compounds of formula Ib

Table III provides 782 compounds of formula Ic

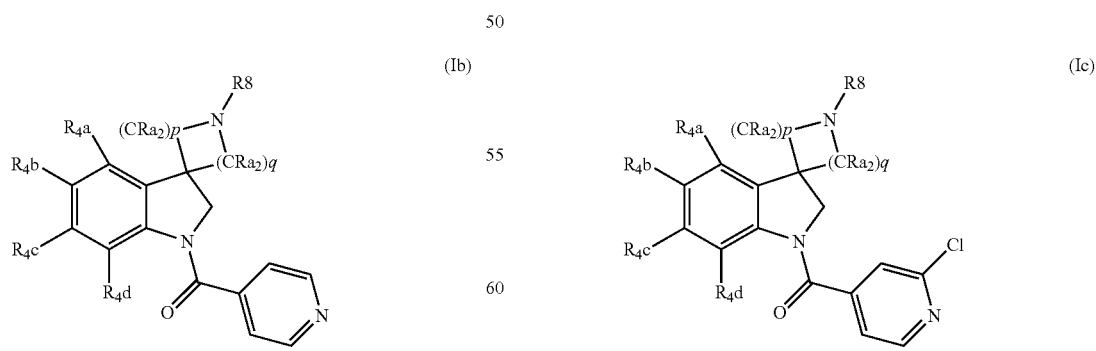

wherein each Ra is H, p is 1, q is 2 and the values of $R^8$, $R^{4a}$, $R^{4b}$, $R^{4c}$ and $R^{4d}$ are given in Table 1.

wherein each Ra is H, p is 1, q is 2 and the values of $R^8$, $R^{4a}$, $R^{4b}$, $R^{4c}$ and $R^{4d}$ are given in Table 1

Table IV provides 782 compounds of formula Id

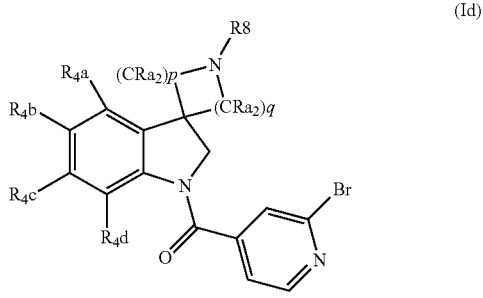
(Id)

wherein each Ra is H, p is 1, q is 2 and the values of $R^8$, $R^{4a}$, $R^{4b}$, $R^{4c}$ and $R^{4d}$ are given in Table 1

Table V provides 782 compounds of formula Ie

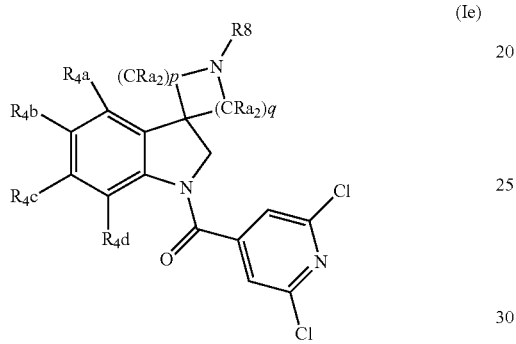
(Ie)

wherein each Ra is H, p is 1, q is 2 and the values of $R^8$, $R^{4a}$, $R^{4b}$, $R^{4c}$ and $R^{4d}$ are given in Table 1

Table VI provides 782 compounds of formula If

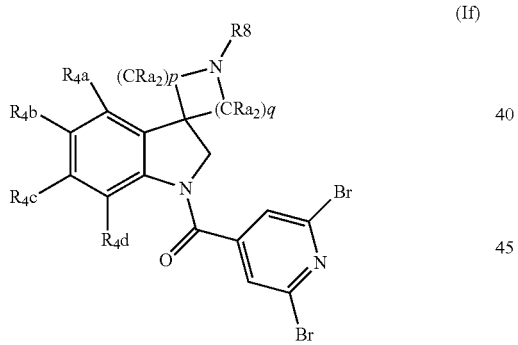
(If)

wherein each Ra is H, p is 1, q is 2 and the values of $R^8$, $R^{4a}$, $R^{4b}$, $R^{4c}$ and $R^{4d}$ are given in Table 1

Table VII provides 782 compounds of formula Ig

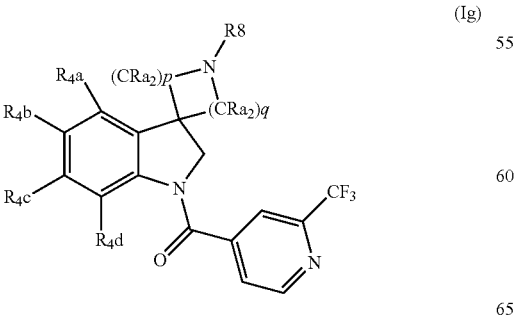
(Ig)

wherein each Ra is H, p is 1, q is 2 and the values of $R^8$, $R^{4a}$, $R^{4b}$, $R^{4c}$ and $R^{4d}$ are given in Table 1.

Table VIII provides 782 compounds of formula Ih

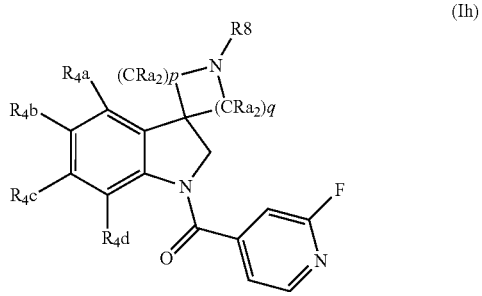
(Ih)

wherein each Ra is H, p is 1, q is 2 and the values of $R^8$, $R^{4a}$, $R^{4b}$, $R^{4c}$ and $R^{4d}$ are given in Table 1

Table IX provides 782 compounds of formula Ii

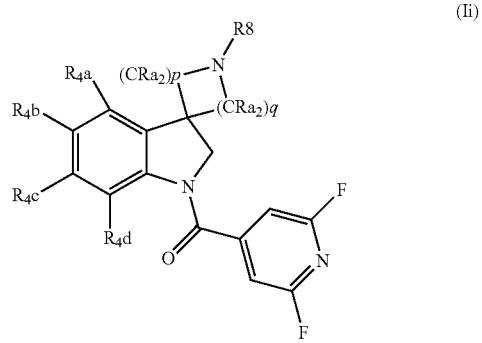
(Ii)

wherein each Ra is H, p is 1, q is 2 and the values of $R^8$, $R^{4a}$, $R^{4b}$, $R^{4c}$ and $R^{4d}$ are given in Table 1.

Table X provides 782 compounds of formula Ij

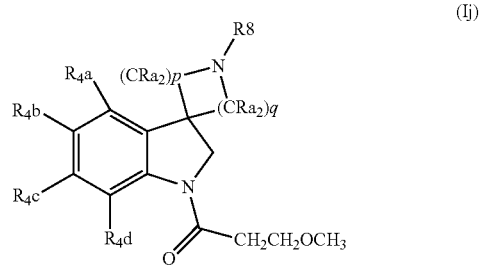
(Ij)

wherein each Ra is H, p is 1, q is 2 and the values of $R^8$, $R^{4a}$, $R^{4b}$, $R^{4c}$ and $R^{4d}$ are given in Table 1.

Table XI provides 782 compounds of formula Ik

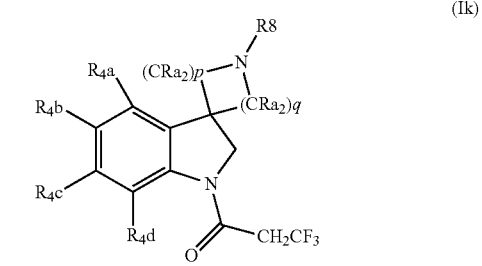
(Ik)

wherein each Ra is H, p is 1, q is 2 and the values of $R^8$, $R^{4a}$, $R^{4b}$, $R^{4c}$ and $R^{4d}$ are given in Table 1.

Table XII provides 782 compounds of formula Il

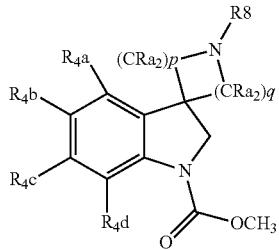

(Il)

wherein each Ra is H, p is 1, q is 2 and the values of $R^8$, $R^{4a}$, $R^{4b}$, $R^{4c}$ and $R^{4d}$ are given in Table 1.

Table XIII provides 782 compounds of formula Im

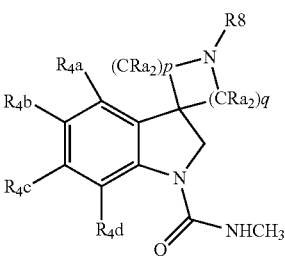

(Im)

wherein each Ra is H, p is 1, q is 2 and the values of $R^8$, $R^{4a}$, $R^{4b}$, $R^{4c}$ and $R^{4d}$ are given in Table 1.

Table XIV provides 782 compounds of formula In

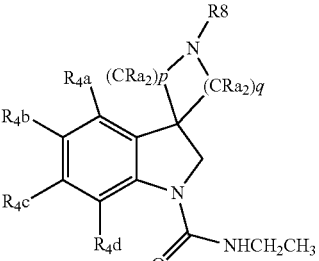

(In)

wherein each Ra is H, p is 1, q is 2 and the values of $R^8$, $R^{4a}$, $R^{4b}$, $R^{4c}$ and $R^{4d}$ are given in Table 1.

Table XV provides 782 compounds of formula Io

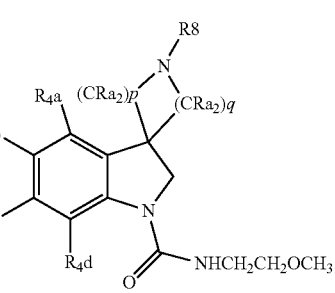

(Io)

wherein each Ra is H, p is 1, q is 2 and the values of $R^8$, $R^{4a}$, $R^{4b}$, $R^{4c}$ and $R^{4d}$ are given in Table 1.

Table XVI provides 782 compounds of formula Ip

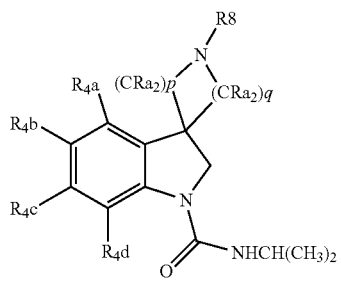

(Ip)

wherein each Ra is H, p is 1, q is 2 and the values of $R^8$, $R^{4a}$, $R^{4b}$, $R^{4c}$ and $R^{4d}$ are given in Table 1.

Table XVII provides 782 compounds of formula Iq

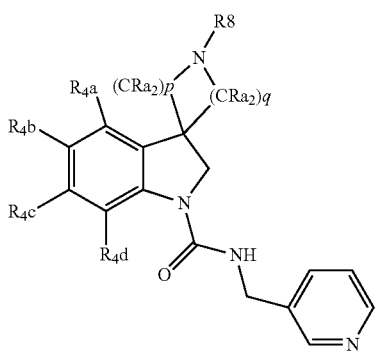

(Iq)

wherein each Ra is H, p is 1, q is 2 and the values of $R^8$, $R^{4a}$, $R^{4b}$, $R^{4c}$ and $R^{4d}$ are given in Table 1.

Table XVIII provides 782 compounds of formula Ir

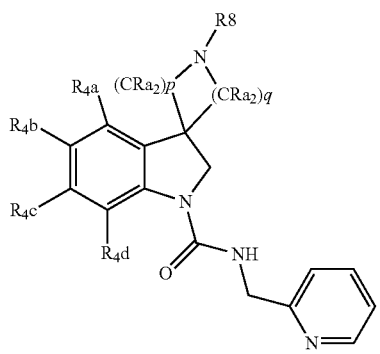

(Ir)

wherein each Ra is H, p is 1, q is 2 and the values of $R^8$, $R^{4a}$, $R^{4b}$, $R^{4c}$ and $R^{4d}$ are given in Table 1.

Table XIX provides 782 compounds of formula Is

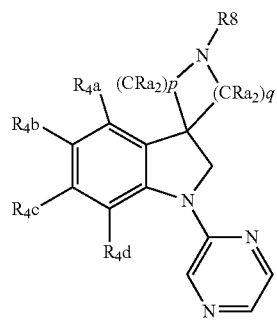

(Is)

Table XX provides 782 compounds of formula It

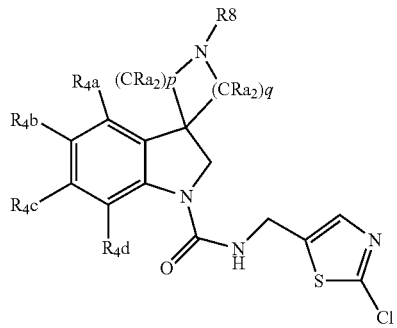
(It)

wherein each Ra is H, p is 1, q is 2 and the values of $R^8$, $R^{4a}$, $R^{4b}$, $R^{4c}$ and $R^{4d}$ are given in Table 1.

Table XXI provides 782 compounds of formula Iu

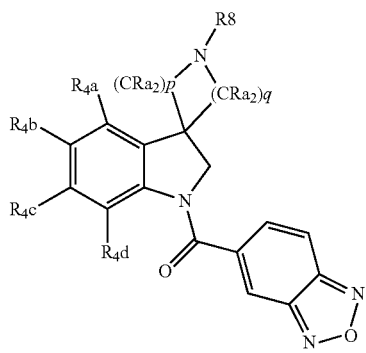
(Iu)

wherein each Ra is H, p is 1, q is 2 and the values of $R^8$, $R^{4a}$, $R^{4b}$, $R^{4c}$ and $R^{4d}$ are given in Table 1.

Table XXII provides 782 compounds of formula Iv

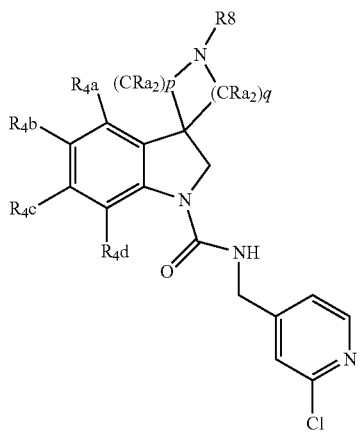
(Iv)

wherein each Ra is H, p is 1, q is 2 and the values of $R^8$, $R^{4a}$, $R^{4b}$, $R^{4c}$ and $R^{4d}$ are given in Table 1.

Table XXIII provides 782 compounds of formula Iw

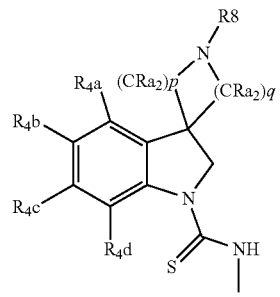
(Iw)

wherein each Ra is H, p is 1, q is 2 and the values of $R^8$, $R^{4a}$, $R^{4b}$, $R^{4c}$ and $R^{4d}$ are given in Table 1.

Table XXIV provides 782 compounds of formula Ix

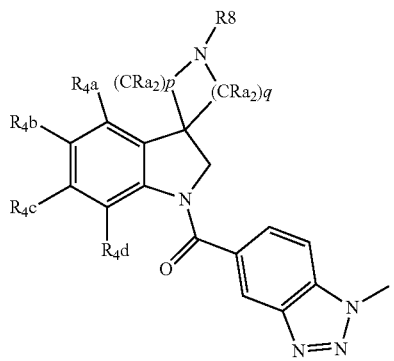
(Ix)

wherein each Ra is H, p is 1, q is 2 and the values of $R^8$, $R^{4a}$, $R^{4b}$, $R^{4c}$ and $R^{4d}$ are given in Table 1.

Table XXV provides 782 compounds of formula Iy

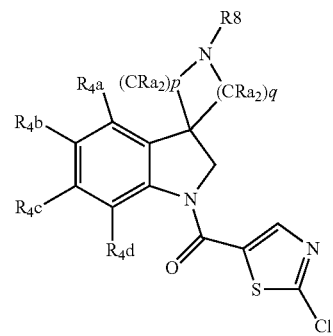
(Iy)

wherein each Ra is H, p is 1, q is 2 and the values of $R^8$, $R^{4a}$, $R^{4b}$, $R^{4c}$ and $R^{4d}$ are given in Table 1.

Table XXVI provides 782 compounds of formula Iz

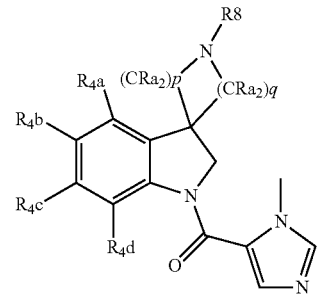
(Iz)

wherein each Ra is H, p is 1, q is 2 and the values of $R^8$, $R^{4a}$, $R^{4b}$, $R^{4c}$ and $R^{4d}$ are given in Table 1.

Table XXVII provides 782 compounds of formula Iaa

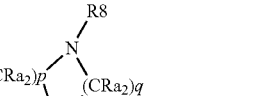
(Iaa)

wherein each Ra is H, p is 1, q is 2 and the values of $R^8$, $R^{4a}$, $R^{4b}$, $R^{4c}$ and $R^{4d}$ are given in Table 1.

Table XXVIII provides 782 compounds of formula Iab

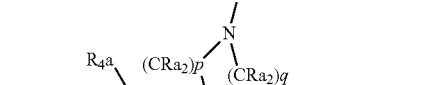
(Iab)

wherein each Ra is H, p is 1, q is 2 and the values of $R^8$, $R^{4a}$, $R^{4b}$, $R^{4c}$ and $R^{4d}$ are given in Table 1.

Table XXIX provides 782 compounds of formula Iac

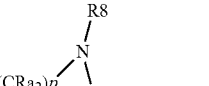
(Iac)

wherein each Ra is H, p is 1, q is 2 and the values of $R^8$, $R^{4a}$, $R^{4b}$, $R^{4c}$ and $R^{4d}$ are given in Table 1.

Table XXX provides 782 compounds of formula Iad

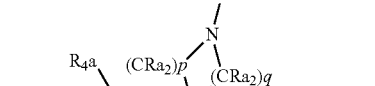
(Iad)

wherein each Ra is H, p is 1, q is 2 and the values of $R^8$, $R^{4a}$, $R^{4b}$, $R^{4c}$ and $R^{4d}$ are given in Table 1.

Table XXXI provides 782 compounds of formula Iae

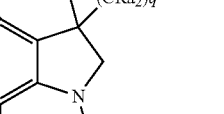
(Iae)

wherein each Ra is H, p is 1, q is 2 and the values of $R^8$, $R^{4a}$, $R^{4b}$, $R^{4c}$ and $R^{4d}$ are given in Table 1.

Table XXXII provides 782 compounds of formula Iaf

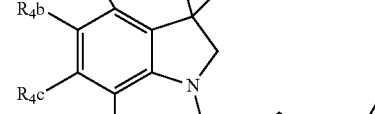
(Iaf)

wherein each Ra is H, p is 1, q is 2 and the values of $R^8$, $R^{4a}$, $R^{4b}$, $R^{4c}$ and $R^{4d}$ are given in Table 1.

Table XXXIII provides 782 compounds of formula Iag

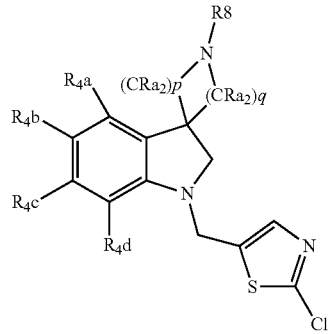

(Iag)

wherein each Ra is H, p is 1, q is 2 and the values of $R^8$, $R^{4a}$, $R^{4b}$, $R^{4c}$ and $R^{4d}$ are given in Table 1.

Table XXXIV provides 782 compounds of formula Iah

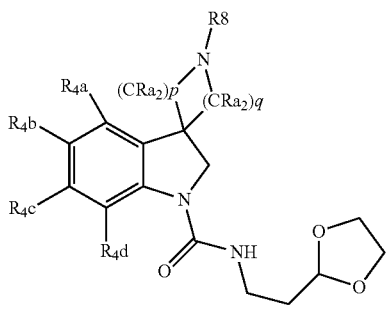

(Iah)

wherein each Ra is H, p is 1, q is 2 and the values of $R^8$, $R^{4a}$, $R^{4b}$, $R^{4c}$ and $R^{4d}$ are given in Table 1.

Table XXXV provides 782 compounds of formula Iai

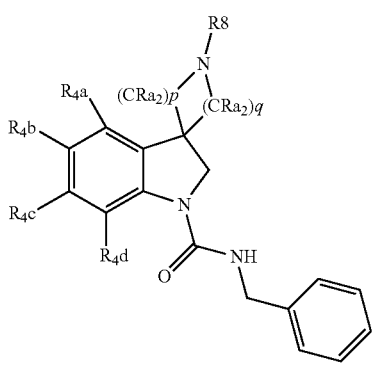

(Iai)

wherein each Ra is H, p is 1, q is 2 and the values of $R^8$, $R^{4a}$, $R^{4b}$, $R^{4c}$ and $R^{4d}$ are given in Table 1.

Table XXXVI provides 782 compounds of formula Iaj

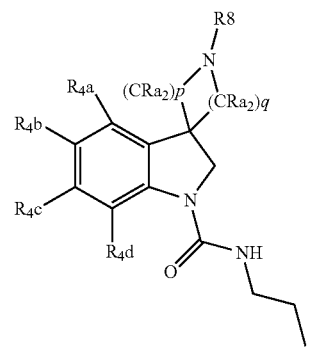

(Iaj)

wherein each Ra is H, p is 1, q is 2 and the values of $R^8$, $R^{4a}$, $R^{4b}$, $R^{4c}$ and $R^{4d}$ are given in Table 1.

Table XXXVII provides 782 compounds of formula Iak

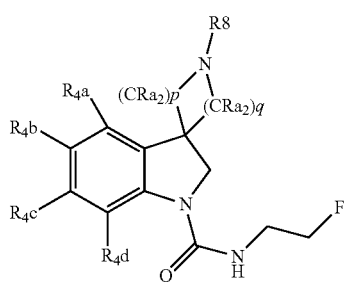

(Iak)

wherein each Ra is H, p is 1, q is 2 and the values of $R^8$, $R^{4a}$, $R^{4b}$, $R^{4c}$ and $R^{4d}$ are given in Table 1.

Table XXXVIII provides 782 compounds of formula Ial

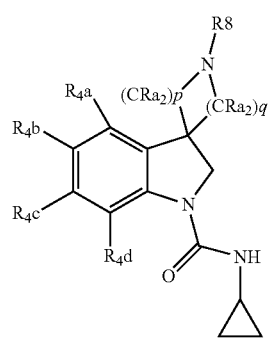

(Ial)

wherein each Ra is H, p is 1, q is 2 and the values of $R^8$, $R^{4a}$, $R^{4b}$, $R^{4c}$ and $R^{4d}$ are given in Table 1.

Table XXXIX provides 782 compounds of formula Iam

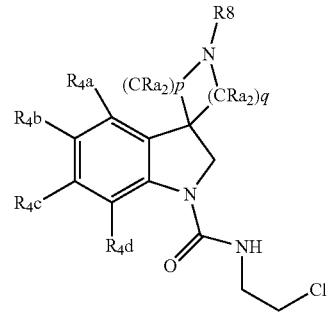

(Iam)

wherein each Ra is H, p is 1, q is 2 and the values of $R^8$, $R^{4a}$, $R^{4b}$, $R^{4c}$ and $R^{4d}$ are given in Table 1.

Table XL provides 782 compounds of formula Ian

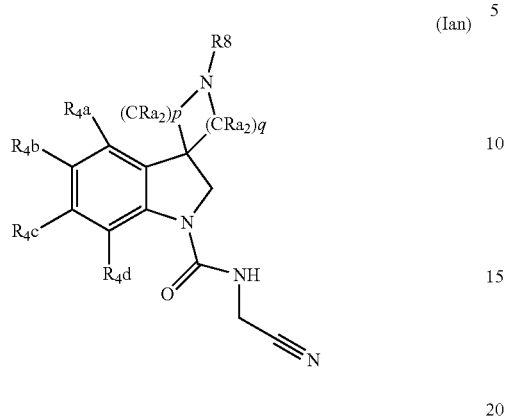
(Ian)

wherein each Ra is H, p is 1, q is 2 and the values of $R^8$, $R^{4a}$, $R^{4b}$, $R^{4c}$ and $R^{4d}$ are given in Table 1.

Table XLI provides 782 compounds of formula Iao

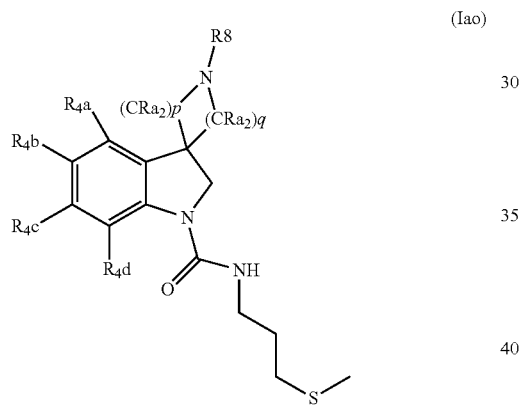
(Iao)

wherein each Ra is H, p is 1, q is 2 and the values of $R^8$, $R^{4a}$, $R^{4b}$, $R^{4c}$ and $R^{4d}$ are given in Table 1.

Table XLII provides 782 compounds of formula Iap

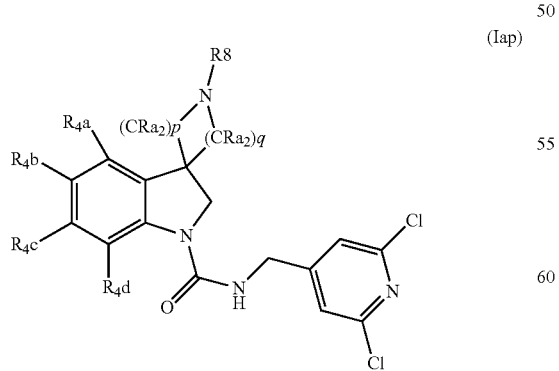
(Iap)

wherein each Ra is H, p is 1, q is 2 and the values of $R^8$, $R^{4a}$, $R^{4b}$, $R^{4c}$ and $R^{4d}$ are given in Table 1.

Table XLIII provides 782 compounds of formula Iaq

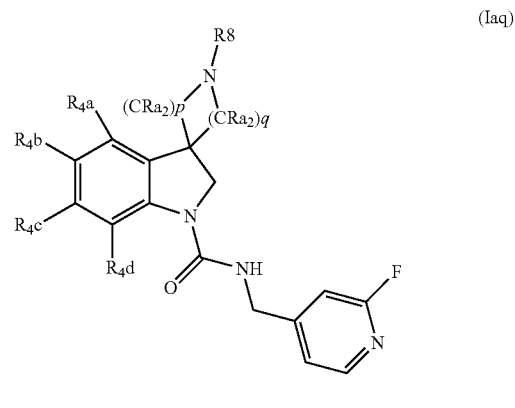
(Iaq)

wherein each Ra is H, p is 1, q is 2 and the values of $R^8$, $R^{4a}$, $R^{4b}$, $R^{4c}$ and $R^{4d}$ are given in Table 1.

Table XLIV provides 782 compounds of formula Iar

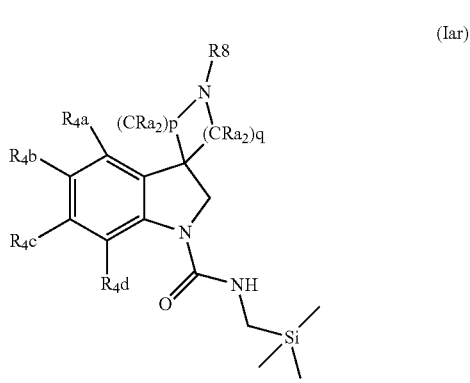
(Iar)

wherein each Ra is H, p is 1, q is 2 and the values of $R^8$, $R^{4a}$, $R^{4b}$, $R^{4c}$ and $R^{4d}$ are given in Table 1.

Table XLV provides 782 compounds of formula Ias

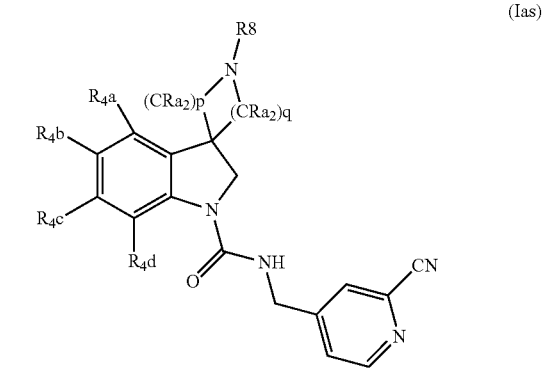
(Ias)

wherein each Ra is H, p is 1, q is 2 and the values of $R^8$, $R^{4a}$, $R^{4b}$, $R^{4c}$ and $R^{4d}$ are given in Table 1.

Table XLVI provides 782 compounds of formula Iat

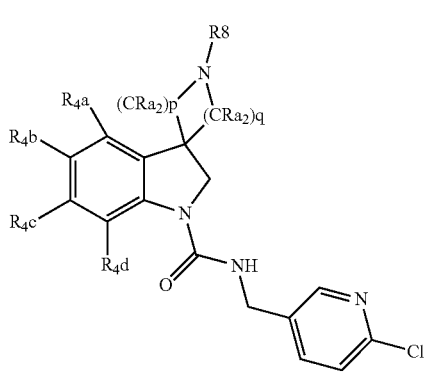
(Iat)

wherein each Ra is H, p is 1, q is 2 and the values of $R^8$, $R^{4a}$, $R^{4b}$, $R^{4c}$ and $R^{4d}$ are given in Table 1.

Table XLVII provides 782 compounds of formula Iau

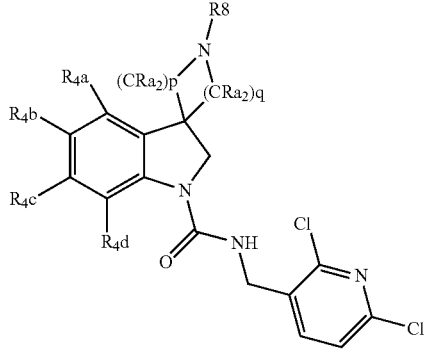
(Iau)

wherein each Ra is H, p is 1, q is 2 and the values of $R^8$, $R^{4a}$, $R^{4b}$, $R^{4c}$ and $R^{4d}$ are given in Table 1.

Table XLVIII provides 782 compounds of formula Iav

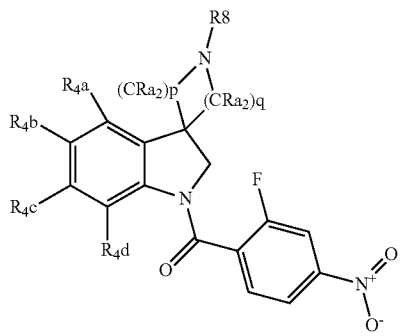
(Iav)

wherein each Ra is H, p is 1, q is 2 and the values of $R^8$, $R^{4a}$, $R^{4b}$, $R^{4c}$ and $R^{4d}$ are given in Table 1.

Table XLIX provides 782 compounds of formula Iaw

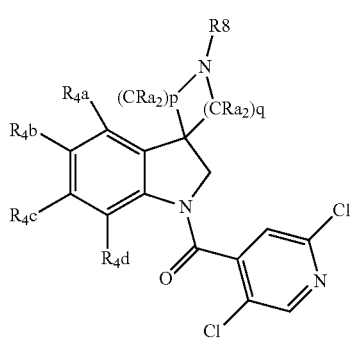
(Iaw)

wherein each Ra is H, p is 1, q is 2 and the values of $R^8$, $R^{4a}$, $R^{4b}$, $R^{4c}$ and $R^{4d}$ are given in Table 1.

Table L provides 782 compounds of formula Iax

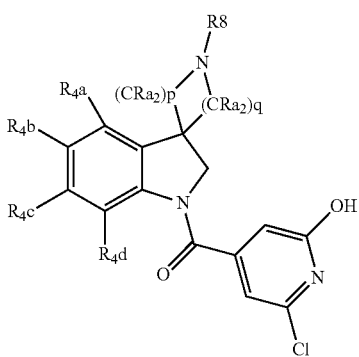
(Iax)

wherein each Ra is H, p is 1, q is 2 and the values of $R^8$, $R^{4a}$, $R^{4b}$, $R^{4c}$ and $R^{4d}$ are given in Table 1.

Table LI provides 782 compounds of formula Iay

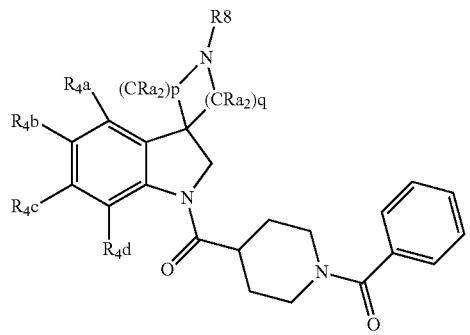
(Iay)

wherein each Ra is H, p is 1, q is 2 and the values of $R^8$, $R^{4a}$, $R^{4b}$, $R^{4c}$ and $R^{4d}$ are given in Table 1.

Table LII provides 782 compounds of formula Iaz

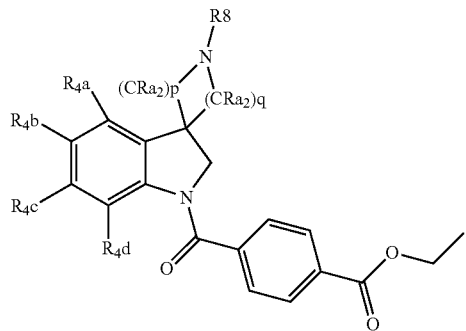

wherein each Ra is H, p is 1, q is 2 and the values of $R^8$, $R^{4a}$, $R^{4b}$, $R^{4c}$ and $R^{4d}$ are given in Table 1.

Table LIII provides 782 compounds of formula Iba

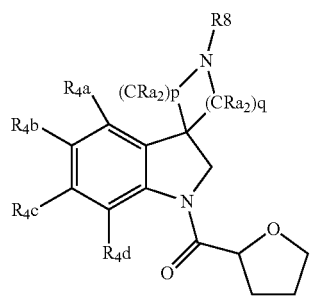

wherein each Ra is H, p is 1, q is 2 and the values of $R^8$, $R^{4a}$, $R^{4b}$, $R^{4c}$ and $R^{4d}$ are given in Table 1.

Table LIV provides 782 compounds of formula Ibb

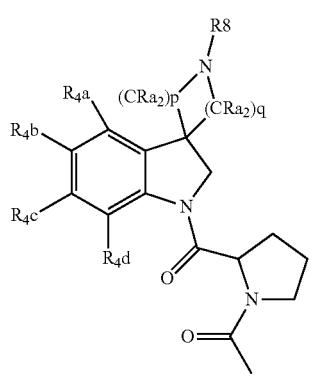

wherein each Ra is H, p is 1, q is 2 and the values of $R^8$, $R^{4a}$, $R^{4b}$, $R^{4c}$ and $R^{4d}$ are given in Table 1.

Table LV provides 782 compounds of formula Ibc

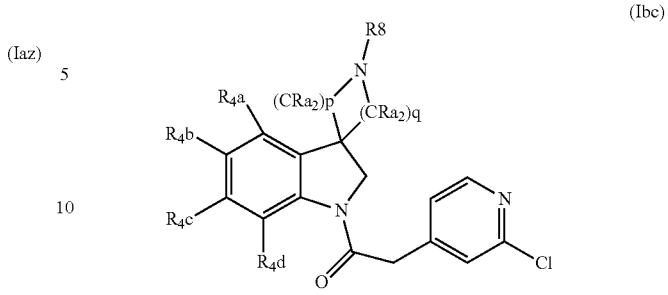

wherein each Ra is H, p is 1, q is 2 and the values of $R^8$, $R^{4a}$, $R^{4b}$, $R^{4c}$ and $R^{4d}$ are given in Table 1.

Table LVI provides 782 compounds of formula Ibd

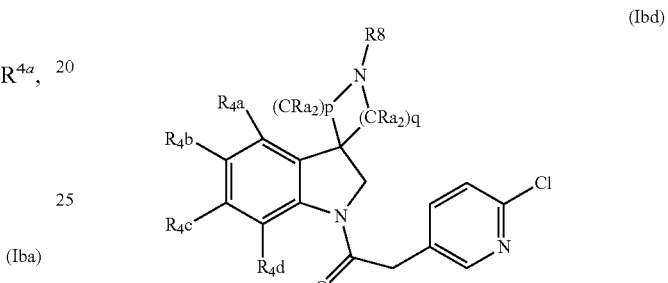

wherein each Ra is H, p is 1, q is 2 and the values of $R^8$, $R^{4a}$, $R^{4b}$, $R^{4c}$ and $R^{4d}$ are given in Table 1.

Table LVII provides 782 compounds of formula Ibe

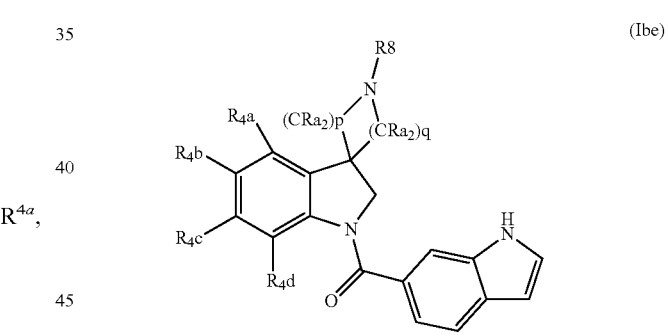

wherein each Ra is H, p is 1, q is 2 and the values of $R^8$, $R^{4a}$, $R^{4b}$, $R^{4c}$ and $R^{4d}$ are given in Table 1.

Table LVIII provides 782 compounds of formula Ibf

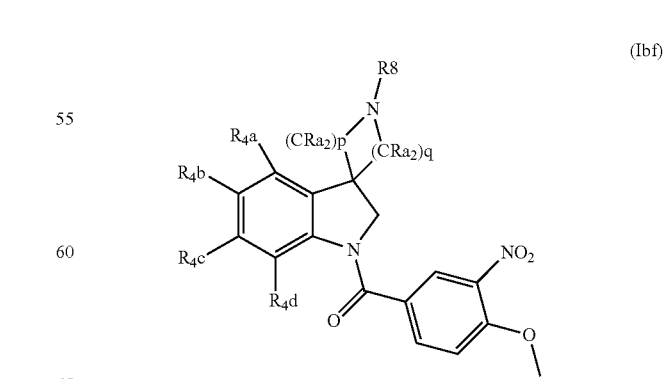

wherein each Ra is H, p is 1, q is 2 and the values of $R^8$, $R^{4a}$, $R^{4b}$, $R^{4c}$ and $R^{4d}$ are given in Table 1.

Table LIX provides 782 compounds of formula Ibg

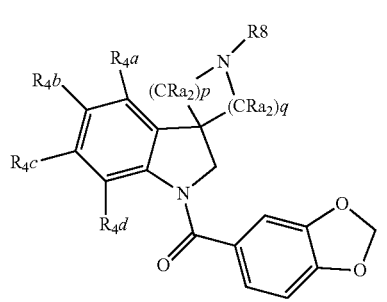
(Ibg)

wherein each Ra is H, p is 1, q is 2 and the values of $R^8$, $R^{4a}$, $R^{4b}$, $R^{4c}$ and $R^{4d}$ are given in Table 1.

Table LX provides 782 compounds of formula Ibh

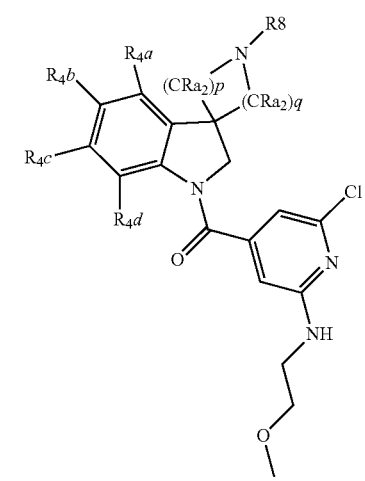
(Ibh)

wherein each Ra is H, p is 1, q is 2 and the values of $R^8$, $R^{4a}$, $R^{4b}$, $R^{4c}$ and $R^{4d}$ are given in Table 1.

Table LXI provides 782 compounds of formula Ibi

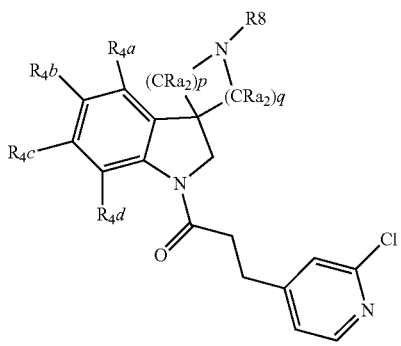
(Ibi)

wherein each Ra is H, p is 1, q is 2 and the values of $R^8$, $R^{4a}$, $R^{4b}$, $R^{4c}$ and $R^{4d}$ are given in Table 1.

Table LXII provides 782 compounds of formula Ibj

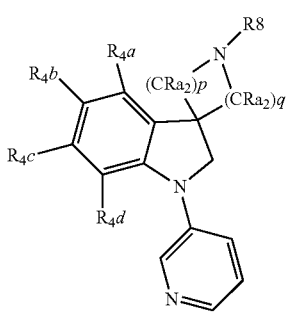
(Ibj)

wherein each Ra is H, p is 1, q is 2 and the values of $R^8$, $R^{4a}$, $R^{4b}$, $R^{4c}$ and $R^{4d}$ are given in Table 1.

Table LXIII provides 782 compounds of formula Ibk

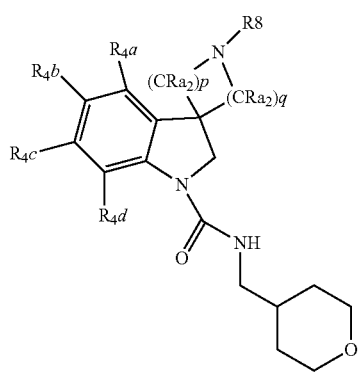
(Ibk)

wherein each Ra is H, p is 1, q is 2 and the values of $R^8$, $R^{4a}$, $R^{4b}$, $R^{4c}$ and $R^{4d}$ are given in Table 1.

Table LXIV provides 782 compounds of formula Ibl

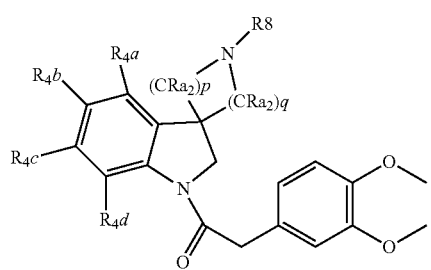
(Ibl)

wherein each Ra is H, p is 1, q is 2 and the values of $R^8$, $R^{4a}$, $R^{4b}$, $R^{4c}$ and $R^{4d}$ are given in Table 1.

Table LXV provides 782 compounds of formula Ibm (Ibm)

wherein each Ra is H, p is 1, q is 2 and the values of $R^8$, $R^{4a}$, $R^{4b}$, $R^{4c}$ and $R^{4d}$ are given in Table 1.

Table LXVI provides 782 compounds of formula Ibn (Ibn)

wherein each Ra is H, p is 1, q is 2 and the values of $R^8$, $R^{4a}$, $R^{4b}$, $R^{4c}$ and $R^{4d}$ are given in Table 1.

Table LXVII provides 782 compounds of formula Ibo (Ibo)

wherein each Ra is H, p is 1, q is 2 and the values of $R^8$, $R^{4a}$, $R^{4b}$, $R^{4c}$ and $R^{4d}$ are given in Table 1.

Table LXVIII provides 782 compounds of formula Ibp (Ibp)

wherein each Ra is H, p is 1, q is 2 and the values of $R^8$, $R^{4a}$, $R^{4b}$, $R^{4c}$ and $R^{4d}$ are given in Table 1.

Table LXIX provides 782 compounds of formula Ia wherein each Ra is H, p is 1, q is 3 and the values of $R^8$, $R^{4a}$, $R^{4b}$, $R^{4c}$ and $R^{4d}$ are given in Table 1.

Table LXX provides 782 compounds of formula Ib wherein each Ra is H, p is 1, q is 3 and the values of $R^8$, $R^{4a}$, $R^{4b}$, $R^{4c}$ and $R^{4d}$ are given in Table 1.

Table LXXI provides 782 compounds of formula Ic wherein each Ra is H, p is 1, q is 3 and the values of $R^8$, $R^{4a}$, $R^{4b}$, $R^{4c}$ and $R^{4d}$ are given in Table 1.

Table LXXII provides 782 compounds of formula Id wherein each Ra is H, p is 1, q is 3 and the values of $R^8$, $R^{4a}$, $R^{4b}$, $R^{4c}$ and $R^{4d}$ are given in Table 1.

Table LXXIII provides 782 compounds of formula Ie wherein each Ra is H, p is 1, q is 3 and the values of $R^8$, $R^{4a}$, $R^{4b}$, $R^{4c}$ and $R^{4d}$ are given in Table 1.

Table LXXIV provides 782 compounds of formula If wherein each Ra is H, p is 1, q is 3 and the values of $R^8$, $R^{4a}$, $R^{4b}$, $R^{4c}$ and $R^{4d}$ are given in Table 1.

Table LXXV provides 782 compounds of formula Ig wherein each Ra is H, p is 1, q is 3 and the values of $R^8$, $R^{4a}$, $R^{4b}$, $R^{4c}$ and $R^{4d}$ are given in Table 1.

Table LXXVI provides 782 compounds of formula Ih wherein each Ra is H, p is 1, q is 3 and the values of $R^8$, $R^{4a}$, $R^{4b}$, $R^{4c}$ and $R^{4d}$ are given in Table 1.

Table LXXVII provides 782 compounds of formula Ii wherein each Ra is H, p is 1, q is 3 and the values of $R^8$, $R^{4a}$, $R^{4b}$, $R^{4c}$ and $R^{4d}$ are given in Table 1.

Table LXXVIII provides 782 compounds of formula Ij wherein each Ra is H, p is 1, q is 3 and the values of $R^8$, $R^{4a}$, $R^{4b}$, $R^{4c}$ and $R^{4d}$ are given in Table 1.

Table LXXXIX provides 782 compounds of formula Ik wherein each Ra is H, p is 1, q is 3 and the values of $R^8$, $R^{4a}$, $R^{4b}$, $R^{4c}$ and $R^{4d}$ are given in Table 1.

Table LXXX provides 782 compounds of formula Il wherein each Ra is H, p is 1, q is 3 and the values of $R^8$, $R^{4a}$, $R^{4b}$, $R^{4c}$ and $R^{4d}$ are given in Table 1.

Table LXXXI provides 782 compounds of formula Im wherein each Ra is H, p is 1, q is 3 and the values of $R^8$, $R^{4a}$, $R^{4b}$, $R^{4c}$ and $R^{4d}$ are given in Table 1.

Table LXXXII provides 782 compounds of formula In wherein each Ra is H, p is 1, q is 3 and the values of $R^8$, $R^{4a}$, $R^{4b}$, $R^{4c}$ and $R^{4d}$ are given in Table 1.

Table LXXXIII provides 782 compounds of formula Io wherein each Ra is H, p is 1, q is 3 and the values of $R^8$, $R^{4a}$, $R^{4b}$, $R^{4c}$ and $R^{4d}$ are given in Table 1.

Table LXXXIV provides 782 compounds of formula Ip wherein each Ra is H, p is 1, q is 3 and the values of $R^8$, $R^{4a}$, $R^{4b}$, $R^{4c}$ and $R^{4d}$ are given in Table 1.

Table LXXXV provides 782 compounds of formula Iq wherein each Ra is H, p is 1, q is 3 and the values of $R^8$, $R^{4a}$, $R^{4b}$, $R^{4c}$ and $R^{4d}$ are given in Table 1.

Table LXXXVI provides 782 compounds of formula Ir wherein each Ra is H, p is 1, q is 3 and the values of $R^8$, $R^{4a}$, $R^{4b}$, $R^{4c}$ and $R^{4d}$ are given in Table 1.

Table LXXXVII provides 782 compounds of formula Is wherein each Ra is H, p is 1, q is 3 and the values of $R^8$, $R^{4a}$, $R^{4b}$, $R^{4c}$ and $R^{4d}$ are given in Table 1.

Table LXXXVIII provides 782 compounds of formula It wherein each Ra is H, p is 1, q is 3 and the values of $R^8$, $R^{4a}$, $R^{4b}$, $R^{4c}$ and $R^{4d}$ are given in Table 1.

Table LXXXIX provides 782 compounds of formula Iu wherein each Ra is H, p is 1, q is 3 and the values of $R^8$, $R^{4a}$, $R^{4b}$, $R^{4c}$ and $R^{4d}$ are given in Table 1.

Table XC provides 782 compounds of formula Iv wherein each Ra is H, p is 1, q is 3 and the values of $R^8$, $R^{4a}$, $R^{4b}$, $R^{4c}$ and $R^{4d}$ are given in Table 1.

Table XCI provides 782 compounds of formula Iw wherein each Ra is H, p is 1, q is 3 and the values of $R^8$, $R^{4a}$, $R^{4b}$, $R^{4c}$ and $R^{4d}$ are given in Table 1.

Table XCII provides 782 compounds of formula Ix wherein each Ra is H, p is 1, q is 3 and the values of $R^8$, $R^{4a}$, $R^{4b}$, $R^{4c}$ and $R^{4d}$ are given in Table 1.

Table XCIII provides 782 compounds of formula Iy wherein each Ra is H, p is 1, q is 3 and the values of $R^8$, $R^{4a}$, $R^{4b}$, $R^{4c}$ and $R^{4d}$ are given in Table 1.

Table XCIV provides 782 compounds of formula Iz wherein each Ra is H, p is 1, q is 3 and the values of $R^8$, $R^{4a}$, $R^{4b}$, $R^{4c}$ and $R^{4d}$ are given in Table 1.

Table XCV provides 782 compounds of formula Iaa wherein each Ra is H, p is 1, q is 3 and the values of $R^8$, $R^{4a}$, $R^{4b}$, $R^{4c}$ and $R^{4d}$ are given in Table 1.

Table XCVI provides 782 compounds of formula Iab wherein each Ra is H, p is 1, q is 3 and the values of $R^8$, $R^{4a}$, $R^{4b}$, $R^{4c}$ and $R^{4d}$ are given in Table 1.

Table XCVII provides 782 compounds of formula Iac wherein each Ra is H, p is 1, q is 3 and the values of $R^8$, $R^{4a}$, $R^{4b}$, $R^{4c}$ and $R^{4d}$ are given in Table 1.

Table XCVIII provides 782 compounds of formula Iad wherein each Ra is H, p is 1, q is 3 and the values of $R^8$, $R^{4a}$, $R^{4b}$, $R^{4c}$ and $R^{4d}$ are given in Table 1.

Table XCIX provides 782 compounds of formula Iae wherein each Ra is H, p is 1, q is 3 and the values of $R^8$, $R^{4a}$, $R^{4b}$, $R^{4c}$ and $R^{4d}$ are given in Table 1.

Table C provides 782 compounds of formula Iaf wherein each Ra is H, p is 1, q is 3 and the values of $R^8$, $R^{4a}$, $R^{4b}$, $R^{4c}$ and $R^{4d}$ are given in Table 1.

Table CI provides 782 compounds of formula Iag wherein each Ra is H, p is 1, q is 3 and the values of $R^8$, $R^{4a}$, $R^{4b}$, $R^{4c}$ and $R^{4d}$ are given in Table 1.

Table CII provides 782 compounds of formula Iah wherein each Ra is H, p is 1, q is 3 and the values of $R^8$, $R^{4a}$, $R^{4b}$, $R^{4c}$ and $R^{4d}$ are given in Table 1.

Table CIII provides 782 compounds of formula Iai wherein each Ra is H, p is 1, q is 3 and the values of $R^8$, $R^{4a}$, $R^{4b}$, $R^{4c}$ and $R^{4d}$ are given in Table 1.

Table CIV provides 782 compounds of formula Iaj wherein each Ra is H, p is 1, q is 3 and the values of $R^8$, $R^{4a}$, $R^{4b}$, $R^{4c}$ and $R^{4d}$ are given in Table 1.

Table CV provides 782 compounds of formula Iak wherein each Ra is H, p is 1, q is 3 and the values of $R^8$, $R^{4a}$, $R^{4b}$, $R^{4c}$ and $R^{4d}$ are given in Table 1.

Table CVI provides 782 compounds of formula Ial wherein each Ra is H, p is 1, q is 3 and the values of $R^8$, $R^{4a}$, $R^{4b}$, $R^{4c}$ and $R^{4d}$ are given in Table 1.

Table CVII provides 782 compounds of formula Iam wherein each Ra is H, p is 1, q is 3 and the values of $R^8$, $R^{4a}$, $R^{4b}$, $R^{4c}$ and $R^{4d}$ are given in Table 1.

Table CVIII provides 782 compounds of formula Ian wherein each Ra is H, p is 1, q is 3 and the values of $R^8$, $R^{4a}$, $R^{4b}$, $R^{4c}$ and $R^{4d}$ are given in Table 1.

Table CIX provides 782 compounds of formula Iao wherein each Ra is H, p is 1, q is 3 and the values of $R^8$, $R^{4a}$, $R^{4b}$, $R^{4c}$ and $R^{4d}$ are given in Table 1.

Table CX provides 782 compounds of formula Iap wherein each Ra is H, p is 1, q is 3 and the values of $R^8$, $R^{4a}$, $R^{4b}$, $R^{4c}$ and $R^{4d}$ are given in Table 1.

Table CXI provides 782 compounds of formula Iaq wherein each Ra is H, p is 1, q is 3 and the values of $R^8$, $R^{4a}$, $R^{4b}$, $R^{4c}$ and $R^{4d}$ are given in Table 1.

Table CXII provides 782 compounds of formula Iar wherein each Ra is H, p is 1, q is 3 and the values of $R^8$, $R^{4a}$, $R^{4b}$, $R^{4c}$ and $R^{4d}$ are given in Table 1.

Table CXIII provides 782 compounds of formula Ias wherein each Ra is H, p is 1, q is 3 and the values of $R^8$, $R^{4a}$, $R^{4b}$, $R^{4c}$ and $R^{4d}$ are given in Table 1.

Table CXIV provides 782 compounds of formula Iat wherein each Ra is H, p is 1, q is 3 and the values of $R^8$, $R^{4a}$, $R^{4b}$, $R^{4c}$ and $R^{4d}$ are given in Table 1.

Table CXV provides 782 compounds of formula Iau wherein each Ra is H, p is 1, q is 3 and the values of $R^8$, $R^{4a}$, $R^{4b}$, $R^{4c}$ and $R^{4d}$ are given in Table 1.

Table CXVI provides 782 compounds of formula Iav wherein each Ra is H, p is 1, q is 3 and the values of $R^8$, $R^{4a}$, $R^{4b}$, $R^{4c}$ and $R^{4d}$ are given in Table 1.

Table CXVII provides 782 compounds of formula Iaw wherein each Ra is H, p is 1, q is 3 and the values of $R^8$, $R^{4a}$, $R^{4b}$, $R^{4c}$ and $R^{4d}$ are given in Table 1.

Table CXVIII provides 782 compounds of formula Iax wherein each Ra is H, p is 1, q is 3 and the values of $R^8$, $R^{4a}$, $R^{4b}$, $R^{4c}$ and $R^{4d}$ are given in Table 1.

Table CXIX provides 782 compounds of formula Iay wherein each Ra is H, p is 1, q is 3 and the values of $R^8$, $R^{4a}$, $R^{4b}$, $R^{4c}$ and $R^{4d}$ are given in Table 1.

Table CXX provides 782 compounds of formula Iaz wherein each Ra is H, p is 1, q is 3 and the values of $R^8$, $R^{4a}$, $R^{4b}$, $R^{4c}$ and $R^{4d}$ are given in Table 1.

Table CXXI provides 782 compounds of formula Iba wherein each Ra is H, p is 1, q is 3 and the values of $R^8$, $R^{4a}$, $R^{4b}$, $R^{4c}$ and $R^{4d}$ are given in Table 1.

Table CXXII provides 782 compounds of formula Ibb wherein each Ra is H, p is 1, q is 3 and the values of $R^8$, $R^{4a}$, $R^{4b}$, $R^{4c}$ and $R^{4d}$ are given in Table 1.

Table CXXIII provides 782 compounds of formula Ibc wherein each Ra is H, p is 1, q is 3 and the values of $R^8$, $R^{4a}$, $R^{4b}$, $R^{4c}$ and $R^{4d}$ are given in Table 1.

Table CXXIV provides 782 compounds of formula Ibd wherein each Ra is H, p is 1, q is 3 and the values of $R^8$, $R^{4a}$, $R^{4b}$, $R^{4c}$ and $R^{4d}$ are given in Table 1.

Table CXXV provides 782 compounds of formula Ibe wherein each Ra is H, p is 1, q is 3 and the values of $R^8$, $R^{4a}$, $R^{4b}$, $R^{4c}$ and $R^{4d}$ are given in Table 1.

Table CXXVI provides 782 compounds of formula Ibf wherein each Ra is H, p is 1, q is 3 and the values of $R^8$, $R^{4a}$, $R^{4b}$, $R^{4c}$ and $R^{4d}$ are given in Table 1.

Table CXXVII provides 782 compounds of formula Ibg wherein each Ra is H, p is 1, q is 3 and the values of $R^8$, $R^{4a}$, $R^{4b}$, $R^{4c}$ and $R^{4d}$ are given in Table 1.

Table CXXIII provides 782 compounds of formula Ibh wherein each Ra is H, p is 1, q is 3 and the values of $R^8$, $R^{4a}$, $R^{4b}$, $R^{4c}$ and $R^{4d}$ are given in Table 1.

Table CXXIX provides 782 compounds of formula Ibi wherein each Ra is H, p is 1, q is 3 and the values of $R^8$, $R^{4a}$, $R^{4b}$, $R^{4c}$ and $R^{4d}$ are given in Table 1.

Table CXXX provides 782 compounds of formula Ibj wherein each Ra is H, p is 1, q is 3 and the values of $R^8$, $R^{4a}$, $R^{4b}$, $R^{4c}$ and $R^{4d}$ are given in Table 1.

Table CXXXI provides 782 compounds of formula Ibk wherein each Ra is H, p is 1, q is 3 and the values of $R^8$, $R^{4a}$, $R^{4b}$, $R^{4c}$ and $R^{4d}$ are given in Table 1.

Table CVXXII provides 782 compounds of formula Ibl wherein each Ra is H, p is 1, q is 3 and the values of $R^8$, $R^{4a}$, $R^{4b}$, $R^{4c}$ and $R^{4d}$ are given in Table 1.

Table CXXXIII provides 782 compounds of formula Ibm wherein each Ra is H, p is 3 and the values of $R^8$, $R^{4a}$, $R^{4b}$, $R^{4c}$ and $R^{4d}$ are given in Table 1.

Table CXXXIV provides 782 compounds of formula Ibn wherein each Ra is H, p is 3 and the values of $R^8$, $R^{4a}$, $R^{4b}$, $R^{4c}$ and $R^{4d}$ are given in Table 1.

Table CXXXV provides 782 compounds of formula Ibo wherein each Ra is H, p is 1, q is 3 and the values of $R^8$, $R^{4a}$, $R^{4b}$, $R^{4c}$ and $R^{4d}$ are given in Table 1.

Table CXXXVI provides 782 compounds of formula Ibp wherein each Ra is H, p is 3 and the values of $R^8$, $R^{4a}$, $R^{4b}$, $R^{4c}$ and $R^{4d}$ are given in Table 1.

Table CXXXVII provides 782 compounds of formula Ia wherein each Ra is H, p is 2, q is 3 and the values of $R^8$, $R^{4a}$, $R^{4b}$, $R^{4c}$ and $R^{4d}$ are given in Table 1.

Table CXXXVIII provides 782 compounds of formula Ib wherein each Ra is H, p is 3 and the values of $R^8$, $R^{4a}$, $R^{4b}$, $R^{4c}$ and $R^{4d}$ are given in Table 1.

Table CXXXIX provides 782 compounds of formula Ic wherein each Ra is H, p is 2, q is 3 and the values of $R^8$, $R^{4a}$, $R^{4b}$, $R^{4c}$ and $R^{4d}$ are given in Table 1.

Table CXL provides 782 compounds of formula Id wherein each Ra is H, p is 2, q is 3 and the values of $R^8$, $R^{4a}$, $R^{4b}$, $R^{4c}$ and $R^{4d}$ are given in Table 1.

Table CXLI provides 782 compounds of formula Ie wherein each Ra is H, p is 2, q is 3 and the values of $R^8$, $R^{4a}$, $R^{4b}$, $R^{4c}$ and $R^{4d}$ are given in Table 1.

Table CXLII provides 782 compounds of formula If wherein each Ra is H, p is 2, q is 3 and the values of $R^8$, $R^{4a}$, $R^{4b}$, $R^{4c}$ and $R^{4d}$ are given in Table 1.

Table CXLIII provides 782 compounds of formula Ig wherein each Ra is H, p is 2, q is 3 and the values of $R^8$, $R^{4a}$, $R^{4b}$, $R^{4c}$ and $R^{4d}$ are given in Table 1.

Table CXLIV provides 782 compounds of formula Ih wherein each Ra is H, p is 2, q is 3 and the values of $R^8$, $R^{4a}$, $R^{4b}$, $R^{4c}$ and $R^{4d}$ are given in Table 1.

Table CXLV provides 782 compounds of formula Ii wherein each Ra is H, p is 2, q is 3 and the values of $R^8$, $R^{4a}$, $R^{4b}$, $R^{4c}$ and $R^{4d}$ are given in Table 1.

Table CXLVI provides 782 compounds of formula Ij wherein each Ra is H, p is 2, q is 3 and the values of $R^8$, $R^{4a}$, $R^{4b}$, $R^{4c}$ and $R^{4d}$ are given in Table 1.

Table CXLVII provides 782 compounds of formula Ik wherein each Ra is H, p is 2, q is 3 and the values of $R^8$, $R^{4a}$, $R^{4b}$, $R^{4c}$ and $R^{4d}$ are given in Table 1.

Table CXLVIII provides 782 compounds of formula Il wherein each Ra is H, p is 2, q is 3 and the values of $R^8$, $R^{4a}$, $R^{4b}$, $R^{4c}$ and $R^{4d}$ are given in Table 1.

Table CXLIX provides 782 compounds of formula Im wherein each Ra is H, p is 2, q is 3 and the values of $R^8$, $R^{4a}$, $R^{4b}$, $R^{4c}$ and $R^{4d}$ are given in Table 1.

Table CL provides 782 compounds of formula In wherein each Ra is H, p is 2, q is 3 and the values of $R^8$, $R^{4a}$, $R^{4b}$, $R^{4c}$ and $R^{4d}$ are given in Table 1.

Table CLI provides 782 compounds of formula Io wherein each Ra is H, p is 2, q is 3 and the values of $R^8$, $R^{4a}$, $R^{4b}$, $R^{4c}$ and $R^{4d}$ are given in Table 1.

Table CLII provides 782 compounds of formula Ip wherein each Ra is H, p is 2, q is 3 and the values of $R^8$, $R^{4a}$, $R^{4b}$, $R^{4c}$ and $R^{4d}$ are given in Table 1.

Table CLIII provides 782 compounds of formula Iq wherein each Ra is H, p is 2, q is 3 and the values of $R^8$, $R^{4a}$, $R^{4b}$, $R^{4c}$ and $R^{4d}$ are given in Table 1.

Table CLIV provides 782 compounds of formula Ir wherein each Ra is H, p is 2, q is 3 and the values of $R^8$, $R^{4a}$, $R^{4b}$, $R^{4c}$ and $R^{4d}$ are given in Table 1.

Table CLV provides 782 compounds of formula Is wherein each Ra is H, p is 2, q is 3 and the values of $R^8$, $R^{4a}$, $R^{4b}$, $R^{4c}$ and $R^{4d}$ are given in Table 1.

Table CLVI provides 782 compounds of formula It wherein each Ra is H, p is 2, q is 3 and the values of $R^8$, $R^{4a}$, $R^{4b}$, $R^{4c}$ and $R^{4d}$ are given in Table 1.

Table CLVII provides 782 compounds of formula Iu wherein each Ra is H, p is 2, q is 3 and the values of $R^8$, $R^{4a}$, $R^{4b}$, $R^{4c}$ and $R^{4d}$ are given in Table 1.

Table CLVIII provides 782 compounds of formula Iv wherein each Ra is H, p is 2, q is 3 and the values of $R^8$, $R^{4a}$, $R^{4b}$, $R^{4c}$ and $R^{4d}$ are given in Table 1.

Table CLIX provides 782 compounds of formula Iw wherein each Ra is H, p is 2, q is 3 and the values of $R^8$, $R^{4a}$, $R^{4b}$, $R^{4c}$ and $R^{4d}$ are given in Table 1.

Table CLX provides 782 compounds of formula Ix wherein each Ra is H, p is 2, q is 3 and the values of $R^8$, $R^{4a}$, $R^{4b}$, $R^{4c}$ and $R^{4d}$ are given in Table 1.

Table CLXI provides 782 compounds of formula Iy wherein each Ra is H, p is 2, q is 3 and the values of $R^8$, $R^{4a}$, $R^{4b}$, $R^{4c}$ and $R^{4d}$ are given in Table 1.

Table CLXII provides 782 compounds of formula Iz wherein each Ra is H, p is 2, q is 3 and the values of $R^8$, $R^{4a}$, $R^{4b}$, $R^{4c}$ and $R^{4d}$ are given in Table 1.

Table CLXIII provides 782 compounds of formula Iaa wherein each Ra is H, p is 2, q is 3 and the values of $R^8$, $R^{4a}$, $R^{4b}$, $R^{4c}$ and $R^{4d}$ are given in Table 1.

Table CLXIV provides 782 compounds of formula Iab wherein each Ra is H, p is 2, q is 3 and the values of $R^8$, $R^{4a}$, $R^{4b}$, $R^{4c}$ and $R^{4d}$ are given in Table 1.

Table CLXV provides 782 compounds of formula Iac wherein each Ra is H, p is 2, q is 3 and the values of $R^8$, $R^{4a}$, $R^{4b}$, $R^{4c}$ and $R^{4d}$ are given in Table 1.

Table CLXVI provides 782 compounds of formula Iad wherein each Ra is H, p is 2, q is 3 and the values of $R^8$, $R^{4a}$, $R^{4b}$, $R^{4c}$ and $R^{4d}$ are given in Table 1.

Table CLXVII provides 782 compounds of formula Iae wherein each Ra is H, p is 2, q is 3 and the values of $R^8$, $R^{4a}$, $R^{4b}$, $R^{4c}$ and $R^{4d}$ are given in Table 1.

Table CLXIII provides 782 compounds of formula Iaf wherein each Ra is H, p is 2, q is 3 and the values of $R^8$, $R^{4a}$, $R^{4b}$, $R^{4c}$ and $R^{4d}$ are given in Table 1.

Table CLXIX provides 782 compounds of formula Iag wherein each Ra is H, p is 2, q is 3 and the values of $R^8$, $R^{4a}$, $R^{4b}$, $R^{4c}$ and $R^{4d}$ are given in Table 1.

Table CLXX provides 782 compounds of formula Iah wherein each Ra is H, p is 2, q is 3 and the values of $R^8$, $R^{4a}$, $R^{4b}$, $R^{4c}$ and $R^{4d}$ are given in Table 1.

Table CLXXI provides 782 compounds of formula Iai wherein each Ra is H, p is 2, q is 3 and the values of $R^8$, $R^{4a}$, $R^{4b}$, $R^{4c}$ and $R^{4d}$ are given in Table 1.

Table CLXXII provides 782 compounds of formula Iaj wherein each Ra is H, p is 2, q is 3 and the values of $R^8$, $R^{4a}$, $R^{4b}$, $R^{4c}$ and $R^{4d}$ are given in Table 1.

Table CLXXIII provides 782 compounds of formula Iak wherein each Ra is H, p is 2, q is 3 and the values of $R^8$, $R^{4a}$, $R^{4b}$, $R^{4c}$ and $R^{4d}$ are given in Table 1.

Table CLXXIV provides 782 compounds of formula Ial wherein each Ra is H, p is 2, q is 3 and the values of $R^8$, $R^{4a}$, $R^{4b}$, $R^{4c}$ and $R^{4d}$ are given in Table 1.

Table CLXXV provides 782 compounds of formula Iam wherein each Ra is H, p is 2, q is 3 and the values of $R^8$, $R^{4a}$, $R^{4b}$, $R^{4c}$ and $R^{4d}$ are given in Table 1.

Table CLXXVI provides 782 compounds of formula Ian wherein each Ra is H, p is 2, q is 3 and the values of $R^8$, $R^{4a}$, $R^{4b}$, $R^{4c}$ and $R^{4d}$ are given in Table 1.

Table CLXXVII provides 782 compounds of formula Iao wherein each Ra is H, p is 2, q is 3 and the values of $R^8$, $R^{4a}$, $R^{4b}$, $R^{4c}$ and $R^{4d}$ are given in Table 1.

Table CLXXVIII provides 782 compounds of formula Iap wherein each Ra is H, p is 3 and the values of $R^8$, $R^{4a}$, $R^{4b}$, $R^{4c}$ and $R^{4d}$ are given in Table 1.

Table CLXXIX provides 782 compounds of formula Iaq wherein each Ra is H, p is 2, q is 3 and the values of $R^8$, $R^{4a}$, $R^{4b}$, $R^{4c}$ and $R^{4d}$ are given in Table 1.

Table CLXXX provides 782 compounds of formula Iar wherein each Ra is H, p is 3 and the values of $R^8$, $R^{4a}$, $R^{4b}$, $R^{4c}$ and $R^{4d}$ are given in Table 1.

Table CLXXXI provides 782 compounds of formula Ias wherein each Ra is H, p is 2, q is 3 and the values of $R^8$, $R^{4a}$, $R^{4b}$, $R^{4c}$ and $R^{4d}$ are given in Table 1.

Table CLXXXII provides 782 compounds of formula Iat wherein each Ra is H, p is 3 and the values of $R^8$, $R^{4a}$, $R^{4b}$, $R^{4c}$ and $R^{4d}$ are given in Table 1.

Table CLXXXIII provides 782 compounds of formula Iau wherein each Ra is H, p is 2, q is 3 and the values of $R^8$, $R^{4a}$, $R^{4b}$, $R^{4c}$ and $R^{4d}$ are given in Table 1.

Table CLXXXIV provides 782 compounds of formula Iav wherein each Ra is H, p is 2, q is 3 and the values of $R^8$, $R^{4a}$, $R^{4b}$, $R^{4c}$ and $R^{4d}$ are given in Table 1.

Table CLXXXV provides 782 compounds of formula Iaw wherein each Ra is H, p is 2, q is 3 and the values of $R^8$, $R^{4a}$, $R^{4b}$, $R^{4c}$ and $R^{4d}$ are given in Table 1.

Table CLXXXVI provides 782 compounds of formula Iax wherein each Ra is H, p is 2, q is 3 and the values of $R^8$, $R^{4a}$, $R^{4b}$, $R^{4c}$ and $R^{4d}$ are given in Table 1.

Table CLXXXVII provides 782 compounds of formula Iay wherein each Ra is H, p is 2, q is 3 and the values of $R^8$, $R^{4a}$, $R^{4b}$, $R^{4c}$ and $R^{4d}$ are given in Table 1.

Table CLXXXVIII provides 782 compounds of formula Iaz wherein each Ra is H, p is 2, q is 3 and the values of $R^8$, $R^{4a}$, $R^{4b}$, $R^{4c}$ and $R^{4d}$ are given in Table 1.

Table CLXXXIX provides 782 compounds of formula %a wherein each Ra is H, p is 2, q is 3 and the values of $R^8$, $R^{4a}$, $R^{4b}$, $R^{4c}$ and $R^{4d}$ are given in Table 1.

Table CXC provides 782 compounds of formula Ibb wherein each Ra is H, p is 2, q is 3 and the values of $R^8$, $R^{4a}$, $R^{4b}$, $R^{4c}$ and $R^{4d}$ are given in Table 1.

Table CXCI provides 782 compounds of formula Ibc wherein each Ra is H, p is 2, q is 3 and the values of $R^8$, $R^{4a}$, $R^{4b}$, $R^{4c}$ and $R^{4d}$ are given in Table 1.

Table CXCII provides 782 compounds of formula Ibd wherein each Ra is H, p is 2, q is 3 and the values of $R^8$, $R^{4a}$, $R^{4b}$, $R^{4c}$ and $R^{4d}$ are given in Table 1.

Table CXCIII provides 782 compounds of formula Ibe wherein each Ra is H, p is 2, q is 3 and the values of $R^8$, $R^{4a}$, $R^{4b}$, $R^{4c}$ and $R^{4d}$ are given in Table 1.

Table CXCIV provides 782 compounds of formula Ibf wherein each Ra is H, p is 2, q is 3 and the values of $R^8$, $R^{4a}$, $R^{4b}$, $R^{4c}$ and $R^{4d}$ are given in Table 1.

Table CXCV provides 782 compounds of formula Ibg wherein each Ra is H, p is 2, q is 3 and the values of $R^8$, $R^{4a}$, $R^{4b}$, $R^{4c}$ and $R^{4d}$ are given in Table 1.

Table CXCVI provides 782 compounds of formula Ibh wherein each Ra is H, p is 2, q is 3 and the values of $R^8$, $R^{4a}$, $R^{4b}$, $R^{4c}$ and $R^{4d}$ are given in Table 1.

Table CXCVII provides 782 compounds of formula Ibi wherein each Ra is H, p is 2, q is 3 and the values of $R^8$, $R^{4a}$, $R^{4b}$, $R^{4c}$ and $R^{4d}$ are given in Table 1.

Table CXCVIII provides 782 compounds of formula Ibj wherein each Ra is H, p is 2, q is 3 and the values of $R^8$, $R^{4a}$, $R^{4b}$, $R^{4c}$ and $R^{4d}$ are given in Table 1.

Table CXCIX provides 782 compounds of formula Ibk wherein each Ra is H, p is 2, q is 3 and the values of $R^8$, $R^{4a}$, $R^{4b}$, $R^{4c}$ and $R^{4d}$ are given in Table 1.

Table CC provides 782 compounds of formula Ibl wherein each Ra is H, p is 2, q is 3 and the values of $R^8$, $R^{4a}$, $R^{4b}$, $R^{4c}$ and $R^{4d}$ are given in Table 1.

Table CCI provides 782 compounds of formula Ibm wherein each Ra is H, p is 2, q is 3 and the values of $R^8$, $R^{4a}$, $R^{4b}$, $R^{4c}$ and $R^{4d}$ are given in Table 1.

Table CCII provides 782 compounds of formula Ibn wherein each Ra is H, p is 2, q is 3 and the values of $R^8$, $R^{4a}$, $R^{4b}$, $R^{4c}$ and $R^{4d}$ are given in Table 1.

Table CCIII provides 782 compounds of formula Ibo wherein each Ra is H, p is 2, q is 3 and the values of $R^8$, $R^{4a}$, $R^{4b}$, $R^{4c}$ and $R^{4d}$ are given in Table 1.

Table CCIV provides 782 compounds of formula Ibp wherein each Ra is H, p is 2, q is 3 and the values of $R^8$, $R^{4a}$, $R^{4b}$, $R^{4c}$ and $R^{4d}$ are given in Table 1.

Mass spectra data were obtained for selected compounds of Tables I to CCIV using LCMS: LC5: 254 nm–gradient 10% A to 100% B A=H2O+0.01% HCOOH B=CH$_3$CN/CH$_3$OH+0.01% HCOOH positive electrospray 150-1000 m/z.

The data are shown in Table 2.

Table 2

| Compound | LCMS (Ret. Time, min) | MS data |
|---|---|---|
| III-3 |  | 464/466 |
| III-49 | 2'46 | 498/500/502 |
| LXXI-3 | 2'38 | 478/480 |
| LXXI-26 | 2'49 | 496/498 |
| CXXXIX-49 | 2'39 | 526/528/530 |
| CXLI-49 | 2'55 | 560/562/564 |

The compounds of the invention may be made by a variety of methods. For example they may be prepared according to the reactions of Scheme 1.

SCHEME 1

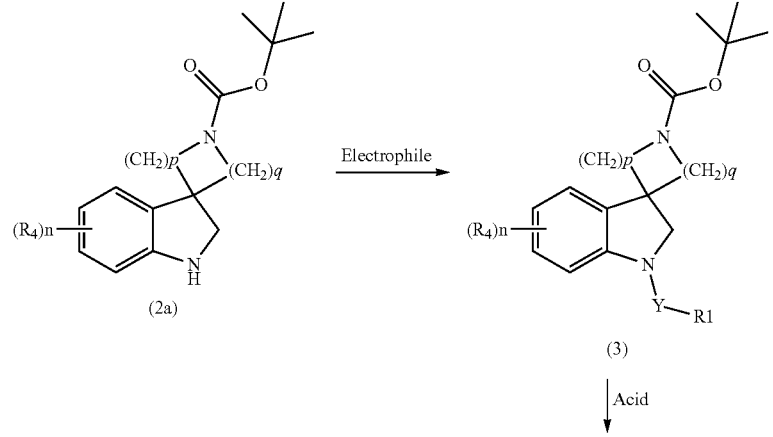

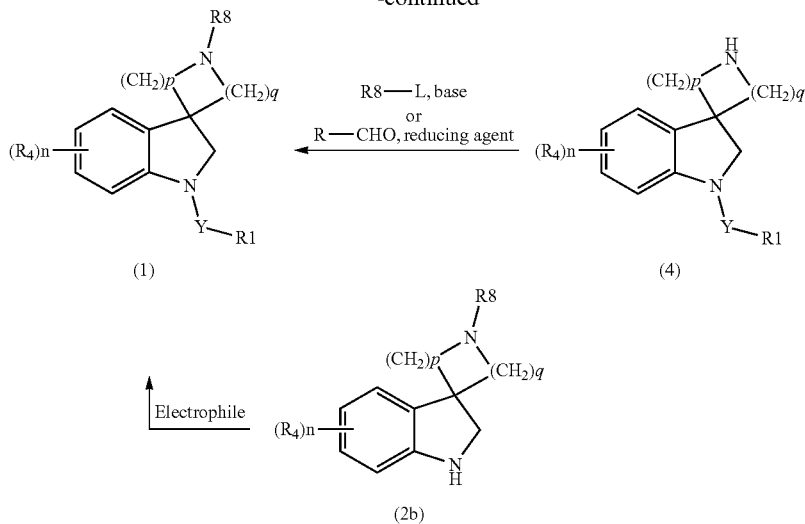

Thus a compound of formula 1 may be synthesised from compounds of formula 4 by reaction with an alkylating agent of the formula R8-L, where L is chloride, bromide, iodide or a sulfonate (e.g. mesylate or tosylate) or similar leaving group at a temperature of between ambient temperature and 100° C., typically ambient temperature, in an organic solvent such as acetonitrile, dimethylformamide, dichloromethane, chloroform or 1,2-dichloroethane in the presence of a tertiary amine base such as triethylamine or diisopropylethylamine and optionally catalysed by halide salts such as sodium iodide, potassium iodide or tetrabutylammonium iodide.

Alternatively, a compound of formula 4 may be reacted with an aldehyde of the formula RCHO at a temperature between ambient temperature and 100° C. in an organic solvent such as tetrahydrofuran or ethanol or mixtures of solvents in the presence of a reducing agent such as borane-pyridine complex, sodium borohydride, sodium (triacetoxy) borohydride, sodium cyanoborohydride or such like, to produce a compound of formula 1 where R8 is $CH_2$—R.

Compounds of formula 1 may also be obtained from compounds of formula 2b by reaction with a suitable electrophilic species. Compounds of formula 1 where Y is a carbonyl group may be formed by the reaction of compounds of formula 4 with a carboxylic acid derivative of formula R1-C(O)—Z where Z is chloride, hydroxy, alkoxy or acyloxy at a temperature between 0° C. and 150° C. optionally in an organic solvent such as dichloromethane, chloroform or 1,2-dichloroethane, optionally in the presence of a tertiary amine base such as triethylamine or diisopropylethylamine and optionally in the presence of a coupling agent such as dicyclohexylcarbodiimide. Compounds of formula 1 where Y is a carbonyl group and R1 is an amino substituent of formula R'—NH— may be formed by the reaction of compounds of formula 2b with an isocyanate of formula R'—N=C=O under similar conditions. Compounds of formula 1 where Y is a group of formula $S(O)_q$ may be formed from compounds of formula 2b by treatment with compounds of formula of R1-S(O)$_q$—Cl under similar conditions. Compounds of formula 1 where Y is a thiocarbonyl group and R1 is an amino substituent of formula R'—NH— may be formed by the reaction of compounds of formula 2b with an isothiocyanate of formula R'—N=C=S under similar conditions.

Alternatively compounds of formula 1 where Y is a thiocarbonyl group and R1 is a carbon substituent may be formed by treatment of compounds of formula 1 where Y is a carbonyl group and R1 is a carbon substituent with a suitable thionating agent such as Lawesson's reagent.

In the above procedures, acid derivatives of the formula R1-C(O)—Z, isocyanates of formula R'—N=C=O, isothiocyanates of formula R'—N=C=S and sulfur electrophiles of formula R1-S(O)$_q$—Cl are either known compounds or may be formed from known compounds by known methods by a person skilled in the art.

A compound of formula 4 may be obtained from a compound of formula 3 by reaction with an acid such as trifluoroacetic acid at ambient temperature in an organic solvent such as dichloromethane, chloroform or 1,2-dichloroethane followed by neutralisation of the reaction mixture with an aqueous solution of an inorganic base such as sodium carbonate, sodium bicarbonate or similar compound.

A compound of formula 3 may be obtained from a compound of formula 2a by reaction with a suitable electrophilic species, as described above.

Compounds of formula 2a and 2b may be synthesised as described in Scheme 2. Thus, compounds of formula 2a may be obtained by reacting compounds of formula 6a with compounds of formula 5 at a temperature of between 0° C. and 100° C. in an organic solvent such as dichloromethane, chloroform or 1,2-dichloroethane in the presence of an acid such as hydrochloric acid or trifluoroacetic acid and optionnally a co-solvent such as water, methanol or ethanol. The intermediates formed are subsequently treated with a reducing agent such as sodium borohydride, sodium (triacetoxy)borohydride, sodium cyanoborohydride, triethylsilane or similar at ambient temperature in organic solvent such as ethanol or chloroform or with a nucleophile R3-M (where M is a metallic species; R3-M is for example a Gringnard reagent).

Similarly, compounds of formula 2b may be synthesised by reacting compounds of formula 6b with compounds of formula 5 using the conditions described above.

Compounds of formula 6a may be obtained from compounds of formula 7a by reaction with a 1-alkoxy substituted phosphonium salt such as methoxymethyl(triphenyl)phosphonium chloride and a base such as potassium tert-butoxide at a temperature of 0° C. to room temperature in tetrahydrofuran.

Similarly, compounds of formula 6b may be synthesised from compounds of formula 7b using the conditions described above.

Compounds of formula 7a and 7b are either known compounds or may be formed from known compounds by known methods by a person skilled in the art.

hydride or borane at a temperature of between 0° C. and 120° C. in an organic solvent such as tetrahydrofuran, diethyl ether, benzene or toluene. A basic procedure is described in *Synth. Commun.* 1992, 22(5), 729-733.

Compounds of formula 8 may be synthesised by cyclising compounds of formula 9 under radical conditions such as

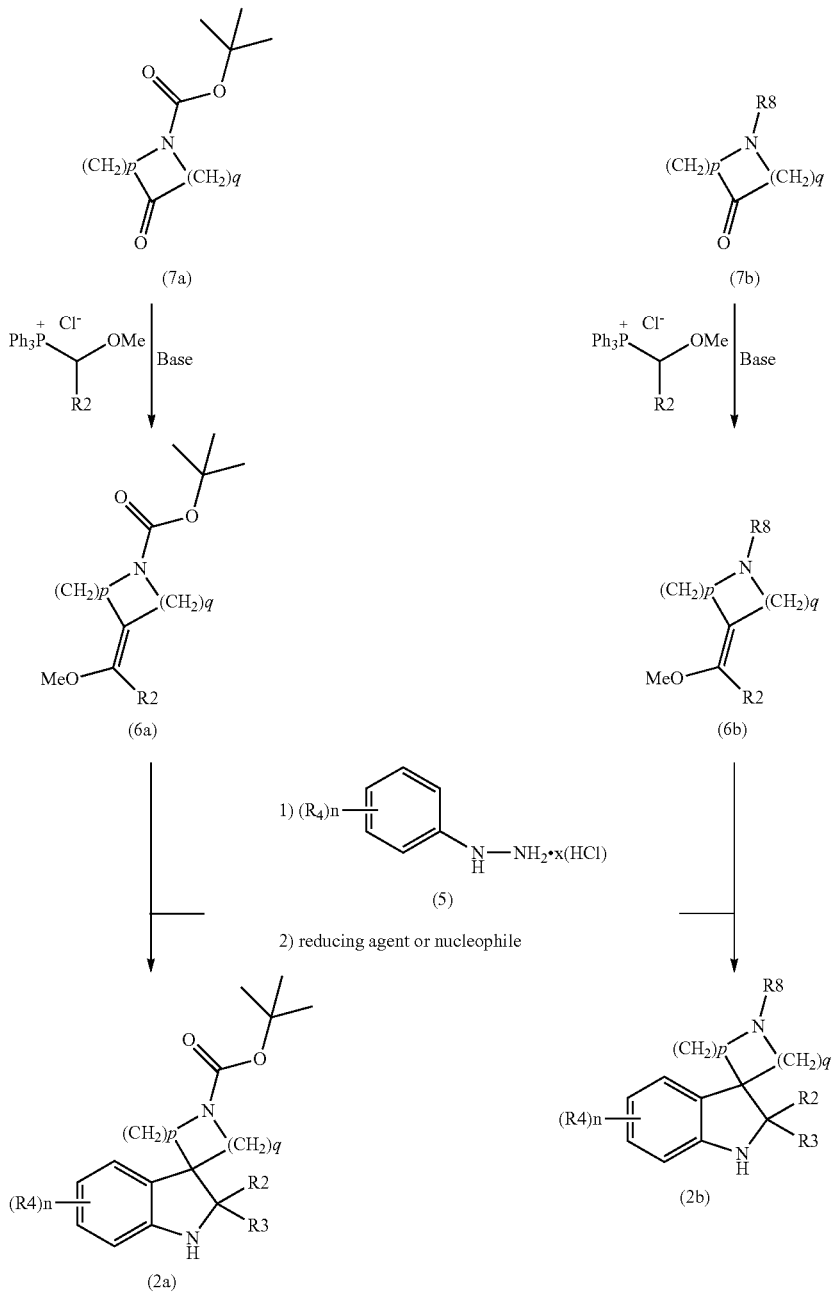

SCHEME 2

A compound of formula 2a, in which p=1 and q=3 may be obtained as shown in Scheme 3.

Thus, a compound of formula 8 may be reduced to a compound of formula 2b in the presence of a reducing agent such as lithium aluminium, bis(2-methoxyethoxy)aluminium tributyltin hydride in the presence of a radical initiator such as 1,1'-azobis(cyclohexanecarbonitrile) in an organic solvent such as benzene or toluene at a temperature of between 60 C and 120° C., followed by removal of the acetyl protecting group using a base such as sodium hydroxide or potassium hydroxide in an organic solvent such as methanol, ethanol or water at a temperature of between 0° C. to 100° C.

Compounds of formula 9 may be synthesised by acylating compounds of formula 11 using known methods by the person skilled in the art.

Alternatively a compound of formula 8 may be obtained by hydrogenation of a compound of formula 10, which may be obtained from a compound of formula 11 by cyclising a compound of formula 10 under Heck conditions in the presence of a catalyst such as palladium(II) acetate, optionally a ligand such as triphenylphosphine or/and an additive such as tetrabutylammonium bromide and a base such as triethylamine in an organic solvent such as tetrahydrofuran, acetonitrile or dimethylformamide at a temperature of between 50° C. to 140° C. A basic procedure is described in WO 01/05790.

Compounds of formula 11 may be synthesised by reacting the known compound of formula 12 (*Chem. Commun.* 1999, 1757-1758) with compounds of formula 13 at temperatures of between 0° C. to 60° C. in an organic solvent such as dichloromethane, benzene or toluene in the presence of a trialkylaluminium reagent such as trimethylaluminium.

Compounds of formula 13 are either known compounds or may be formed from known compounds by known methods by a person skilled in the art.

SCHEME 3

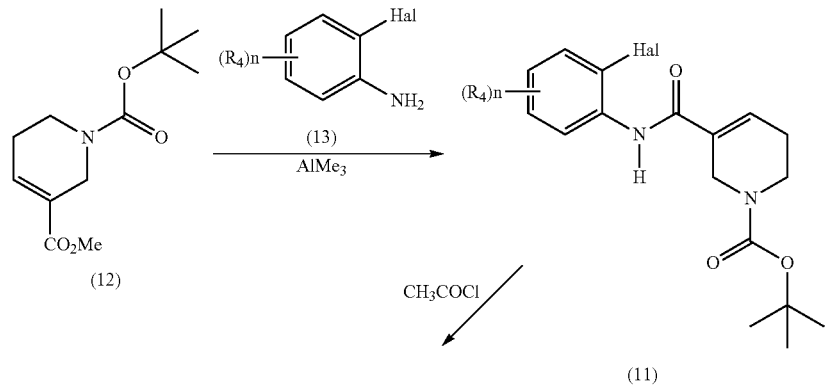

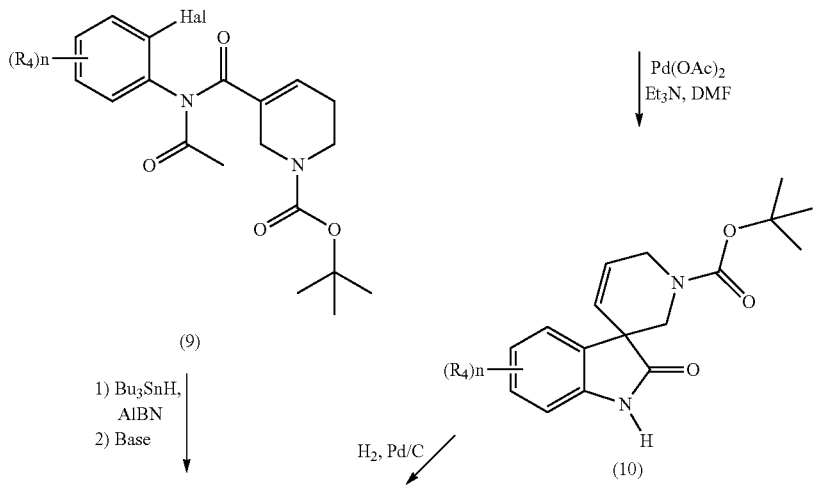

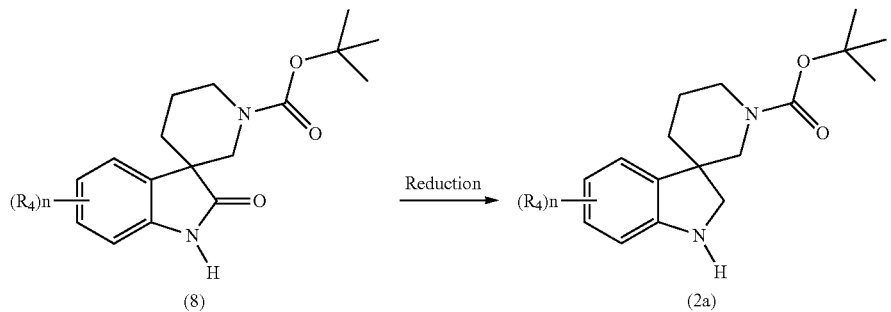

Alternatively a compound of formula 2b, in which p=1 and q=2 may be obtained as shown in Scheme 4.

Thus, compounds of formula 14 may react with a reducing agent such as bis(2-methoxyethoxy)aluminium hydride at a temperature of between 0° C. and 120° C. in an organic solvent such as benzene or toluene to provide compounds of formula 2b, in which p=1 and q=2.

Compounds of formula 14 may be synthesised from compounds of formula 15 by reaction with an alkylating agent of the formula R8-L, where L is chloride, bromide, iodide or a sulfonate (e.g. mesylate or tosylate) or similar leaving group, as described above.

Compounds of formula 15 may be obtained by radical cyclisation of compounds of formula 16 using the method described in *Org. Lett.* 2000, 23, 3599-3601.

Compounds of formula 16 may be synthesised by coupling compounds of formula 18 with the known alcohol 19 (*J. Org. Chem.* 2001, 66, 5545-5551) under Mitsunobu conditions.

Compounds of formula 18 are either known compounds or may be formed from known compounds such as 20 by known methods by a person skilled in the art.

Certain compounds of formula 2a, 2b, 3, 4 and 10 are novel and as such form a further aspect of the invention.

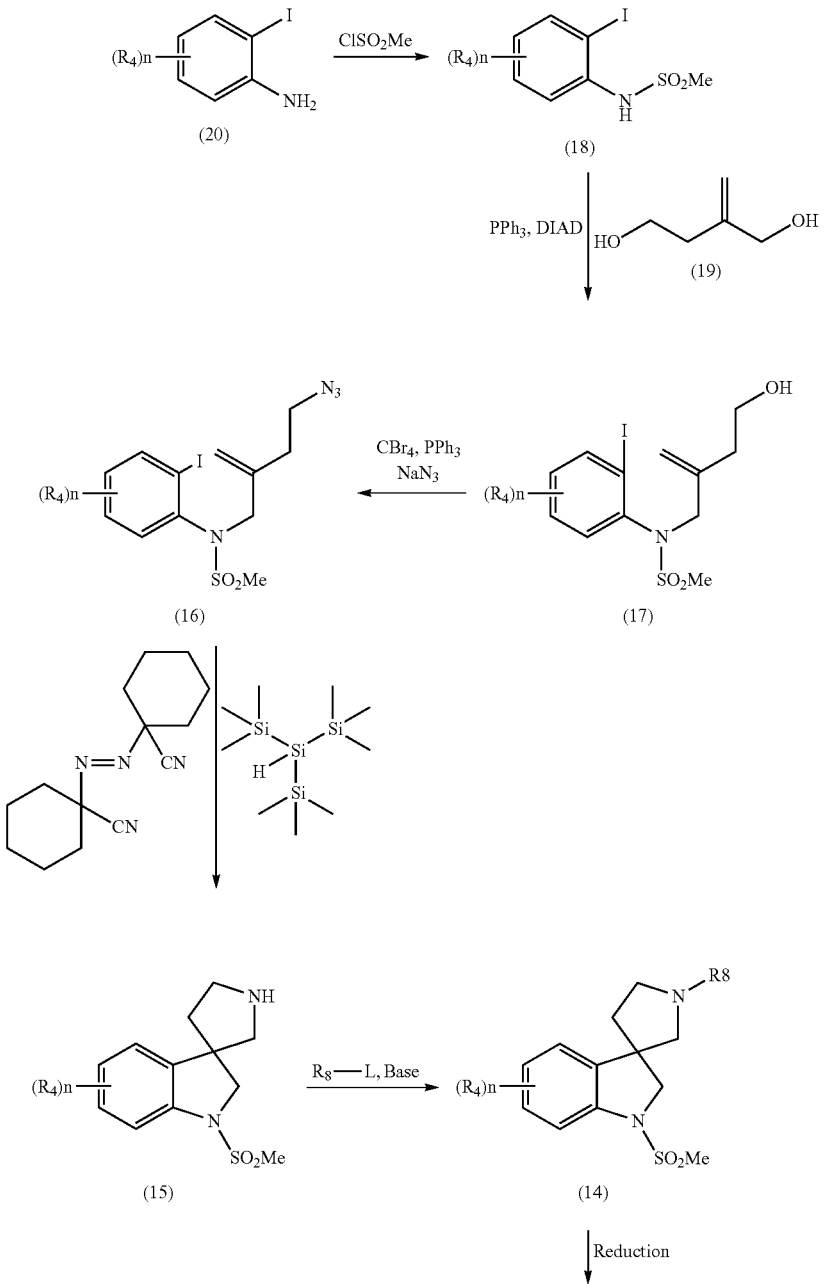

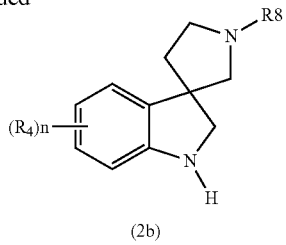

(2b)

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides fells* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus,* and *R. santonensis*) and the *Termitidae* (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following: a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-($E$)-(1R, 3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr; or q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorbenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethyl-benzimidazole-1-sulphonamide, α-[N-(3-chloro-2,6-xylyl)-2-methoxy-acetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)—N-benzyl-N([methyl (methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

EXAMPLE 1

This Example illustrates the preparation of compound CXXXIX-49, 5-chloro-1-(2-chloropyridin-4-yl)carbonyl-1'-[trans-3-(4-chlorophenyl)allyl]spiro[perhydro-azepine-3,3'-piperidine]

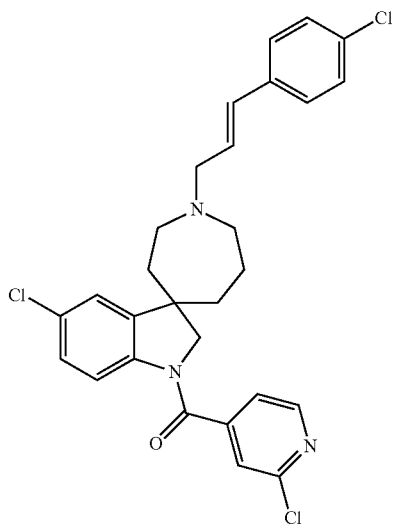 [SMILES: O=C(c1ccnc(Cl)c1)N1CC2(CCCN(C/C=C/c3ccc(Cl)cc3)CC2)c2cc(Cl)ccc21]

Step A: 4-Perhydroazepinone hydrochloride (2.5 g, prepared according to Synth. Commun. 1992, 1249-1258) was suspended in acetonitrile (80 ml); diisopropylethylamine (4.4 ml) and 4-chlorocinnamyl chloride (2.7 g) were successively added at room temperature and the resulting reaction mixture was stirred at room temperature for 20 hours. The solvent was removed in vacuo and the residue purified by silica gel chromatography (eluent cyclohexane:ethyl acetate 6:4) to afford 1-(trans-3-(4-chlorophenyl)allyl)-perhydroazepin-4-one (1.84 g) as a foam. MS (ES+) 264/266 (M+H$^+$).

Step B: To a stirred suspension of methoxymethyltriphenylphosphonium chloride (3.9 g) in tetrahydrofuran (30 ml) at 0° C. unter argon was added portionwise potassium tert-butoxide (1.3 g) over 30 min. 1-(trans-3-(4-chlorophenyl) allyl)-perhydroazepin-4-one (1.5 g) dissolved in a minimum volume of tetrahydrofuran was added to the resulting orange solution and the resulting mixture was stirred at room temperature for 2 hours, quenched by addition of water, extracted twice with ethyl acetate, the organic layers were dried (sodium sulphate) and concentrated in vacuo. Silica gel chromatography (eluent cyclohexane:ethyl acetate 7:3) of the residue afforded 1-[(E)-3-(4-Chloro-phenyl)-allyl]-4-[1-methoxy-meth-(Z)-ylidene]-perhydro-azepine (1.1 g) as an oil (1:1 mixture of isomers). MS (ES+) 292/296 (M+H$^+$).

Step C: A mixture of -[(E)-3-(4-Chloro-phenyl)-allyl]-4-[1-methoxy-meth-(Z)-ylidene]-perhydro-azepine (0.6 g) and 4-chlorophenylhydrazine hydrochloride (0.41 g) in chloroform (20 ml) was treated with trifluoroacetic acid (2.1 ml) and heated at reflux under argon for 18 hours. The reaction mixture was cooled to room temperature, triethylsilane (3.1 ml) was added and the solution refluxed for 2 hours. The reaction mixture was cooled to room temperature, diluted with dichloromethane, neutralised with 30% aqueous ammonium hydroxide, washed with brine, dried (sodium sulphate) and concentrated. The dark residue was purified by silica gel chromatography (cyclohexane:ethyl acetate 1:9) to afford 5-chloro-1'-[trans-3-(4-chlorophenyl)allyl]spiro[perhydro-azepine-3,3'-piperidine] (529 mg). MS (ES+) 387/389 (M+H').

Step D: To a solution of 5-chloro-1'-[trans-3-(4-chlorophenyl)allyl]spiro[perhydro-azepine-3,3'-piperidine] obtained in Step C (250 mg) and triethylamine (0.42 ml) in dichloromethane (10 ml) at 0° C. was added 2-chloro-isonicotinoyl chloride (220 mg) and the resulting solution was kept at room temperature for 18 hours, diluted with dichloromethane, washed with diluted aqueous sodium bicarbonate, dried (sodium sulphate) and concentrated. Silica gel chromatography of the residue (cyclohexane:ethyl acetate 3:7) afforded the title compound as a yellow solid (181 mg); M.p. 86-90° C.; MS (ES+) 526/528/530 (M+H$^+$)

Compound CXLI-49 (M.p. 166-170° C.) was prepared according to procedures analogous to those described in Example 1.

EXAMPLE 2

This Example illustrates the preparation of compound LXXI-3,1-(2-chloropyridin-4-yl)carbonyl-1'-[trans-3-(4-chlorophenyl)allyl]spiro[indoline-3,3'-piperidine]

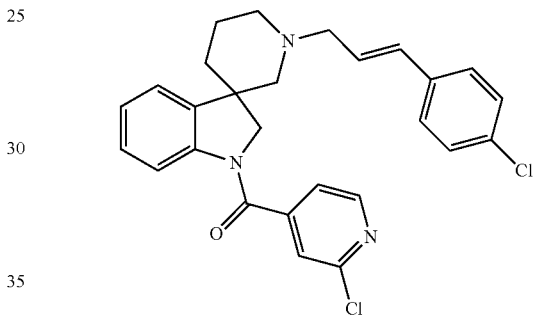

Step A: Trimethylaluminium (2M in heptane, 3 ml) was added dropwise to a solution of 2-bromoaniline (860 mg) in dichloromethane (15 ml). After gas evolution ceased, 5,6-dihydro-2H-pyridine-1,3-dicarboxylic acid 1-tert-butyl ester 3-methyl ester (Chem. Commun. 1999, 1757-1758, 1.2 g) dissolved in dichloromethane (10 ml) was added and the resulting mixture was refluxed for 5 hrs. The solution was cooled to 0° C., quenched by careful addition of saturated aqueous sodium bicarbonate (10 ml) and extracted with dichloromethane. The organic layer was washed with brine, dried (Na$_2$SO$_4$) and concentrated in vacuo. The residue was purified by silica gel chromatography (eluent cyclohexane: ethyl acetate 85:15) to afford 5-(2-bromo-phenylcarbamoyl)-3,6-dihydro-2H-pyridine-1-carboxylic acid tert-butyl ester (1.2 g), which was characterised by its mass and NMR spectra.

Step B: To a stirred solution of the compound obtained in Step A (3.24 g) in dimethylformamide (60 ml) under argon were added successively triethylamine (3 ml), tetrabutyammonium bromide (3.2 g) and palladium(II) acetate (386 mg) and the resulting mixture was heated under reflux for 5 hours, cooled to room temperature, poured into brine and extracted with ethyl acetate. The organic layer was washed with HCl 1N then water, dried over sodium sulfate and concentrated in vacuo. The residue was purified by silica gel chromatography (eluent cyclohexane:ethyl acetate 8:2) to afford spiro[indolin-2-one-3,3'-(1',2',3',4'-tetrahydropyridine]-1'-carboxylic acid tert-butyl ester (1.2 g), which was characterised by its mass and NMR spectra.

Step C: Spiro[indolin-2-one-3,3'-piperidine]-1'-carboxylic acid tert-butyl ester obtained in Step B (1.12 g) was hydrogenated (1 atm.) in 15 ml tetrahydrofuran in the presence of 10% Pd/C (0.6 g) to afford after standard work-up spiro [indolin-2-one-3,3'-piperidine]-1'-carboxylic acid tert-butyl ester (1.06 g), which was characterised by its mass and NMR spectra. MS (ES+) 203 (M—$CO_2$-isoprene+$H^+$), 247 (M-isoprene+$H^+$), 303 (M+$H^+$).

Step D: A solution of spiro[indolin-2-one-3,3'-piperidine]-1'-carboxylic acid tert-butyl ester obtained in Step C (650 mg) in toluene (20 ml) at 70° C. under argon was treated with sodium bis(2-methoxyethoxy)aluminium hydride (Red-Al, 65% in toluene, 1.3 ml) and the reaction mixture was stirred at 75° C. for 2 hours, cooled to room temperature, quenched by addition of ethyl acetate (20 ml), stirred for 15 min. and concentrated in vacuo. The residue was diluted with ethyl acetate, washed with water and brine, dried over sodium sulfate and concentrated in vacuo. The residue was purified by silica gel chromatography (eluent cyclohexane:ethyl acetate 7:3) to afford spiro[indoline-3,3'-piperidine]-1'-carboxylic acid tert-butyl ester (331 mg) as a colorless oil, which was characterised by its mass and NMR spectra. MS (ES+) 233 (M-isoprene+$H^+$), 289 (M+H').

Step E: To a solution of spiro[indoline-3,3'-piperidine]-1'-carboxylic acid tert-butyl ester obtained in Step D (140 mg) and triethylamine (0.28 ml) in dichloromethane (5 ml) at 0° C. was added 2-chloroisonicotinoyl chloride (176 mg). After stirring at room temperature for 1 hour, the solution was diluted with dichloromethane, washed with water, dried (sodium sulfate and concentrated in vacuo. The residue was disoolved in dichloromethane (12.5 ml) and trifluoroacetic acid (1.25 ml) was added. The reaction mixture was stirred at room temperature for 1 hour, diluted with dichloromethane, neutralised with saturated sodium bicarbonate, dried (sodium sulfate) and concentrated in vacuo. The residue was dissolved in acetonitrile (10 ml); diisopropylethylamine (0.13 ml) and 4-chlorocinnamyl chloride (93 mg) were added and the resulting mixture was stirred at room temperature for 12 hours then the solvent was evaporated in vacuo. The residue was purified by silica gel chromatography (eluent cyclohexane:ethyl acetate 6:4) to afford the title product (143 mg), which was characterised by its mass and NMR spectra. MS (ES+) 478/480 (M+$H^+$).

Compound LXXI-26 was prepared according to procedures analogous to those described in Example 2.

EXAMPLE 3

This Example illustrates the preparation of compound III-49, 5-Chloro-1-(2-chloropyridin-4-yl)carbonyl-1'-[trans-3-(4-chlorophenyl)allyl]spiro[indoline-3,3'-pyrrolidine]

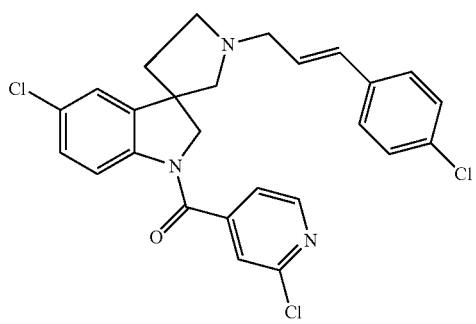 [SMILES: O=C(c1ccnc(Cl)c1)N1CC2(CCN(C/C=C/c3ccc(Cl)cc3)C2)c2cc(Cl)ccc21]

Step A: To a stirred solution of triphenylphosphine (2.75 g) in tetrahydrofuran (60 ml) at −10° C. under argon was added dropwise diisopropylazodicarboxylate (DIAD, 2.1 ml); the resulting suspension was stirred at −10° C. for 15 min then 4-chloro-2-iodo-N-methanesulfonyl-aniline (3.1 g) was added as a solid followed by 2-methylene-butane-1,4-diol (0.95 g) dissolved in a minimum of tetrahydrofuran. The reaction mixture was stirred at room temperature for 6 hours, the solvent was evaporated in vacuo and the residue was purified by silica gel chromatography (eluent ethyl acetate: cyclohexane 4:6) to afford N-(4-Chloro-2-iodo-phenyl)-N-(4-hydroxy-2-methylene-butyl)-methanesulfonamide (3.5 g) contaminated with triphenylphosphine oxide.

Step B: To a stirred solution of N-(4-Chloro-2-iodo-phenyl)-N-(4-hydroxy-2-methylene-butyl)-methanesulfonamide obtained in Step A and triphenylphosphine (3.5 g) in dimethylacetamide (80 ml) at −10° C. under argon was added carbon tetrabromide (4.5 g). The reaction mixture was stirred at −10° C. for 45 min (a precipitate formed). Sodium azide (2 g) was added in one portion and the reaction mixture was stirred at 45° C. for 1 hour, cooled to room temperature, poured into water, extracted with ethyl acetate; the organic layer was washed with brine, dried ($Na_2SO_4$) and concentrated in vacuo. The residue was purified by silica gel chromatography (eluent cyclohexane:ethyl acetate 7:3) to afford N-(4-Chloro-2-iodo-phenyl)-N-(4-azido-2-methylene-butyl)-methanesulfonamide (1.96 g). $^1H$ NMR ($CDCl_3$, 400 MHz) 2.50 (m, 2H), 3.48 (m, 2H), 4.19 (d, J=12.0 Hz, 1H), 4.40 (d, J=12.0 Hz, 1H), 4.90 (s, 1H), 5.01 (s, 1H), 7.29 (d, J=8.5 Hz, 1H), 7.36 (dd, J=0.9H, 8.5 Hz, 1H), 7.92 (d, J=0.9 Hz, 1H).

Step C: A degassed solution of N-(4-Chloro-2-iodo-phenyl)-N-(4-azido-2-methylene-butyl)-methanesulfonamide (1.38 g) in benzene (200 ml) was heated to reflux under argon. Tris(trimethylsilyl)silane (1.32 ml) was added dropwise followed by 1,1'-azobis(cyclohexane carbonitrile) (110 mg). The reaction mixture was stirred at reflux for 20 hours then concentrated in vacuo. The residue was dissolved in ethyl acetate (60 ml), extracted with HC12N (3×60 ml). The aqueous layer was basified with 2N sodium hydroxide (250 ml) then extracted with ethyl acetate (3×150 ml). The combined organic layers were dried over sodium sulfate and the solvent evaporated in vacuo to afford 1-methanesulfonyl-5-chloro-spiro[indoline-3,3'-pyrrolidine] (766 mg) which was used as such for the next step.

Step D: To a solution of 1-methanesulfonyl-5-chloro-spiro [indoline-3,3'-pyrrolidine] (725 mg) in acetonitrile (40 ml) were added diisopropylethylamine (0.66 ml) and 4-chlorocinnamyl chloride (467 mg). The resulting solution was stirred at room temperature for 12 hours, diluted with ethyl acetate, washed with water, brine, dried ($Na_2SO_4$) and concentrated in vacuo. The residue was purified by silica gel chromatography (eluent cyclohexane:ethyl acetate 6:4) to afford 1-methanesulfonyl-5-chloro-1'-[trans-3-(4-chlorophenyl)allyl]spiro[indoline-3,3'-pyrrolidine] (500 mg) which was characterised by its mass and NMR spectra. MS (ES+) 437/439 (M+$H^+$).

Step E: A solution of 1-methanesulfonyl-5-chloro-1'-[trans-3-(4-chlorophenyl)allyl]spiro[indoline-3,3'-pyrrolidine] obtained in Step D (256 mg) in toluene (25 ml) under argon was treated with sodium bis(2-methoxyethoxy)aluminium hydride (Red-Al, 65% in toluene, 0.67 ml) and the reaction mixture was stirred at 100° C. for 1 hour, cooled to room temperature, quenched by addition of ethyl acetate (10 ml), stirred for 15 min and concentrated in vacuo. The residue was purified by silica gel chromatography (eluent ethyl acetate:methanol 95:5) to afford 5-chloro-1'-[trans-3-(4-chlorophenyl)allyl]spiro[indoline-3,3'-pyrrolidine] (157 mg) as a yellow oil, which was characterised by its mass and NMR spectra.

Step F: A solution of 5-chloro-1'-[trans-3-(4-chlorophenyl)allyl]spiro[indoline-3,3'-pyrrolidine] (150 mg) and triethylamine (0.24 ml) in dichloromethane (5 ml) at 0° C. under argon was treated with 2-chloro-isonicotinoyl chloride (147 mg). The resulting solution was stirred at room temperature for 1 hour, poured into saturated aqueous sodium bicarbonate, extracted with ethyl acetate, dried ($Na_2SO_4$) and concentrated in vacuo. Silica gel chromatography of the residue (eluent cyclohexane:ethyl acetate 6:4) afforded the title compound, 1-(2-chloropyridin-4-yl)carbonyl-1'-[trans-3-(4-chlorophenyl)allyl]spiro[indoline-3,3'-pyrrolidine] (95 mg), which was characterised by its mass and NMR spectra. MS (ES+) 498/500 ($M+H^+$).

Compound III-3 was prepared according to procedures analogous to those described in Example 3.

EXAMPLE 4

This Example illustrates the pesticidal/insecticidal properties of compounds of formula (I). Test against were performed as follows:

*Spodoptera littoralis* (Egyptian Cotton Leafworm)

Cotton leaf discs were placed on agar in a 24-well microtiter plate and sprayed with test solutions at an application rate of 200 ppm. After drying, the leaf discs were infested with 5 $L_1$ larvae. The samples were checked for mortality, repellent effect, feeding behaviour, and growth regulation 3 days after treatment (DAT). The following compounds gave at least 80% control of *Spodoptera littoralis*: 111-49 and CXXXIX-49.

*Heliothis virescens* (Tobacco budworm):

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescen*: III-3, III-49, CXXXIX-49 and CXLI-49.

*Plutella xylostella* (Diamond Back Moth):

24-well microtiter plate (MTP) with artificial diet was treated with test solutions at an application rate of 18.2 ppm by pipetting. After drying, the MTP's were infested with larvae (L2)(10-15 per well). After an incubation period of 5 days, samples were checked for larval mortality, antifeedant and growth regulation. The following compounds gave at least 80% control of *Plutella xylostella*: III-49 and CXXXIX-49.

*Aedes aegypti* (Yellow Fever Mosquito):

10-15 *Aedes* larvae (L2) together with a nutrition mixture are placed in 96-well microtiter plates. Test solutions at an application rate of 2 ppm are pipetted into the wells. 2 days later, insects were checked for mortality and growth inhibition. The following compounds gave at least 80% control of *Aedes aegypti*: III-49 and CXLI-49.

The invention claimed is:
1. A compound of formula I'

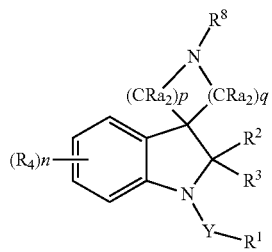

(I')

wherein Y is CO, $R^2$ and $R^3$ are both hydrogen, $R^1$ is hydrogen, $C_{1-6}$ alkyl, $C_{1-6}$ cyanoalkyl, $C_{1-6}$ haloalkyl, $C_{3-7}$ cycloalkyl($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl, $C_{1-6}$ haloalkyl, $C_{1-6}$ alkoxy($C_{1-6}$)alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl), phenyl ($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl ($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino));

each R$^4$ is independently halogen, cyano, $C_{1-8}$ alkyl, $C_{1-8}$ haloalkyl, $C_{1-6}$ cyanoalkyl, $C_{1-6}$ alkoxy($C_{1-6}$)alkyl, $C_{3-7}$ cycloalkyl($C_{1-6}$)alkyl, $C_{5-6}$ cycloalkenyl($C_{1-6}$)alkyl, $C_{3-6}$ alkenyloxy($C_{1-6}$)alkyl, $C_{3-6}$ alkynyloxy($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$)alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$alkylaminocarbonyl($C_{1-6}$)alkyl, di($C_{1-6}$)alkylaminocarbonyl($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl($C_{2-6}$)alkenyl, $C_{1-6}$ alkylaminocarbonyl($C_{2-6}$)alkenyl, di($C_{1-6}$)alkylaminocarbonyl($C_{2-6}$)alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), $C_{2-6}$ alkynyl, trimethylsilyl($C_{2-6}$)alkynyl, aminocarbonyl($C_{2-6}$)alkynyl, $C_{1-6}$ alkylaminocarbonyl($C_{2-6}$)alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$alkyl($C_{3-7}$)-cycloalkyl, $C_{1-3}$alkyl($C_{3-7}$)halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups R$^4$ together with the carbon atoms to which they are attached form a 4, 5, 6 or 7 membered carbocyclic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or R$^{19}$R$^{20}$N where R$^{19}$ and R$^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or R$^{19}$ and R$^{20}$ together with the N atom to which they are attached form a five, six or seven-membered heterocyclic ring which may contain one or two further heteroatoms selected from O, N or S and which may be optionally substituted by one or two $C_{1-6}$ alkyl groups; n is 0, 1, 2 or 3;

each Ra is independently hydrogen, halo, cyano, $C_{1-3}$ alkyl, hydroxy or two Ra groups together with the carbon atom to which they are attached form a carbonyl group;

p is 1 or 2 and q is 2 or 3; provided that when p is 2 then q is not 2;

R$^8$ is $C_{1-10}$ alkyl, $C_{1-10}$ haloalkyl, aryl($C_{1-6}$)alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino), or —C(R$^{51}$)(R$^{52}$)—[CR$^{53}$=CR$^{54}$]z-R$^{55}$ where z is 1 or 2, R$^{51}$ and R$^{52}$ are each independently H, halo or $C_{1-2}$ alkyl, R$^{53}$ and R$^{54}$ are each independently H, halogen, $C_{1-4}$ alkyl or $C_{1-4}$ haloalkyl and R$^{55}$ is aryl (wherein the aryl group may be optionally substituted by one or more substituents independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, CO$_2$H, $C_{1-6}$ alkylcarbonyl, $C_{1-6}$ alkoxycarbonyl, aryl, heteroaryl, R$^{25}$R$^{26}$N or R$^{27}$R$^{28}$NC(O); wherein R$^{25}$, R$^{26}$, R$^{27}$ and R$^{28}$ are, independently, hydrogen or $C_{1-6}$ alkyl) or heteroaryl (wherein the heteroaryl group may be optionally substituted by one or more substituents independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, CO$_2$H, $C_{1-6}$ alkylcarbonyl, $C_{1-6}$ alkoxycarbonyl, aryl, heteroaryl, R$^{25}$R$^{26}$N or R$^{27}$R$^{28}$NC(O); wherein R$^{25}$, R$^{26}$, R$^{27}$ and R$^{28}$ are, independently, hydrogen or $C_{1-6}$ alkyl); or salts or N-oxides thereof provided that when n is 0, p is 1, q is 2, R$^1$ is CH$_3$ and all groups Ra are H then $R^8$ is not H, methyl, benzyl or $CH_2-CH=CH_2$ and when n is 0, $(CRa_2)_p$ is CH-phenyl, $(CRa_2)_q$ is $(CH_2)_2$ and $R^1$ is methyl then $R^8$ is not $COOCH_3$.
2. A compound of formula II
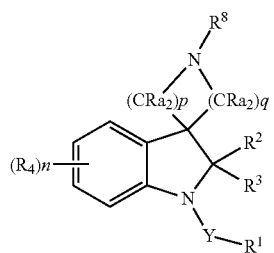
wherein Y, n, p, q, $R^1$, $R^2$, $R^3$, $R^4$ and Ra are as defined in claim 1 and $R^8$ is hydrogen or tert-butoxycarbonyl.
* * * * *